(12) United States Patent
Sehgal et al.

(10) Patent No.: US 7,501,114 B2
(45) Date of Patent: Mar. 10, 2009

(54) EX VIVO AND IN VIVO EXPRESSION OF THE THROMBOMODULIN GENE FOR THE TREATMENT OF CARDIOVASCULAR AND PERIPHERAL VASCULAR DISEASES

(75) Inventors: Lakshman R. Sehgal, Monarch Beach, CA (US); Jonathan Wong, Palo Alto, CA (US)

(73) Assignee: Biovec, LLC, Chicago, IL (US)

( * ) Notice: Subject to any disclaimer, the term of this patent is extended or adjusted under 35 U.S.C. 154(b) by 2 days.

(21) Appl. No.: 11/650,478

(22) Filed: Jan. 8, 2007

(65) Prior Publication Data

US 2007/0184027 A1 Aug. 9, 2007

Related U.S. Application Data

(63) Continuation-in-part of application No. 10/725,013, filed on Dec. 2, 2003, now Pat. No. 7,179,459.

(60) Provisional application No. 60/430,099, filed on Dec. 2, 2002.

(51) Int. Cl.
*A01N 63/00* (2006.01)
*A61K 39/325* (2006.01)
*A61K 31/715* (2006.01)
*C12H 15/86* (2006.01)
*C07H 21/04* (2006.01)

(52) U.S. Cl. ............... 424/93.6; 424/233.1; 514/44; 435/456; 536/23.5; 536/24.1; 536/24.2

(58) Field of Classification Search ............... None
See application file for complete search history.

(56) References Cited

U.S. PATENT DOCUMENTS

| 4,826,811 | A | | 5/1989 | Sehgal et al. | |
| 5,466,668 | A | * | 11/1995 | Glaser et al. | 514/12 |
| 5,827,824 | A | * | 10/1998 | Light et al. | 514/12 |
| 5,863,760 | A | * | 1/1999 | Light et al. | 435/69.1 |
| 5,916,874 | A | * | 6/1999 | Fujiwara et al. | 514/12 |
| 5,981,225 | A | | 11/1999 | Kochanek et al. | |
| 6,290,949 | B1 | | 9/2001 | French et al. | |
| 7,179,459 | B2 | | 2/2007 | Sehgal et al. | |

FOREIGN PATENT DOCUMENTS

WO WO 96/06933 * 3/1996

OTHER PUBLICATIONS

Esmon (Ann. Med. 34: 598-605, 2002).*
Borroni et al (Alzheimer Disease and Associated Disorders 16(3): 150-155, 2002).*
Li et al (J. Vasc. Surg. 32: 804-813, 2000).*
Tohda et al (Arteiosclerosis, Thrombosis, and Vascular Biology;18:1861-1869, 1998).*
Tabuchi et al (Eur. J. Card. Thor. Surg. 26: 995-1000, 2004).*
Miller et al. (FASEB J. 9: 190-199, 1995).*
Crystal (Science 270: 404-410, 1995).*
Verma et al (Nature 389: 239-242, 1997).*
Read et al (Adv. Gen. 53:19-46, 2005).*
Zushi et al, Aspartic acid 349 in the fourth epidermal growth factor-like structure of human thrombomodulin plays a role in its Ca(2+)-mediated binding to protein C. The Journal of Biological Chemistry, (Oct. 25, 1991) vol. 266, No. 30, pp. 19886-1988.*
Tsiang et al, Functional domains of memebrane-bound human thrombomodulin. EGF-like domains four to six and the serine/threonine-rich domain are required for cofactor activity. The Journal of Biological Chemistry, (Mar. 25, 1992) vol. 267, No. 9, pp. 6164-6170.*
Nagashima et al, Alanine-scanning mutagenesis of the epidermal growth factor-like domains of human thrombomodulin identifies critical residues for its cofactor activity. The Journal of Biological Chemistry, (Feb. 5, 1993) vol. 268, No. 4, pp. 2888-2892.*
Lin et al, Modulation of glycosaminoglycan addition in naturally expressed and recombinant human thrombomodlin. The Journal of Biological Chemistry, (Oct. 7, 1994) vol. 269, No. 40, pp. 25021-25030.*
Adler et al, The structure of 19-residue fragment from the C-loop of the fourth epidermal growth factor-like domain of thrombomodulin. The Journal of Biological Chemistry, (Oct. 6, 1995) vol. 270, No. 40, pp. 23366-23372.*
Weiler-Guettler et al, A targeted point mutation in thrombomodulin generates viable mice with a prethrombotic state. The Journal of Clinical Investigation, (May 1, 1998) vol. 101, No. 9, pp. 1983-1991.*
Gerlitz et al, Identification of the predominant glycosaminoglycan-attachment site in soluble recombinant human thrombomodulin: potential regulation of functionality by glycosyltransferase competition for serine474. The Biochemical Journal, (Oct. 1, 1993) vol. 295 (Pt. 1), pp. 131-140.*
Waugh et al (Circulation 102(3): 332-337, 2000).*
Zuckerbraun, Brian S., et al., "Vascular Gene Therapy, A Reality of the 21$^{st}$ Century," Arch. Surg., vol. 137, pp. 854-861 (2002).
Kibbe, Melina R., et al., "Gene Therapy for Restenosis," Circ. Res., vol. 86, pp. 829-833 (2000).
Shears, Larry L., et al., "Efficient Inibition of Intimal Hyperplasia by Adenovirus-Mediated Inducible Nitric Oxide Synthase Gene Transfer to Rats and Pigs In Vivo," J. Am. Coll. Surg., vol. 187, No. 3, pp. 295-306 (1998).
Russell Ross, "The pathogenesis of atherosclerosis: a perspective for the 1990s," Nature, vol. 362, pp. 801-809 (1993).
Sadler, J. Evan, "Thrombomodulin Structure and Function," Tehomb Haemost., vol. 78, pp. 392-395 (1997).
Esmon, Charles T., "Thrombomodulin as a model of molecular mechanisms that modulate protease specificity and function at the vessel surface," Faseb J., vol. 9; pp. 946-955 (1995).

(Continued)

*Primary Examiner*—Richard Schnizer
(74) *Attorney, Agent, or Firm*—Ping Wang; Morris Manning & Martin, LLP

(57) ABSTRACT

The present invention relates to methods and compositions for treatment of cardiovascular and peripheral vascular diseases using ex vivo and in vivo gene delivery technologies. One aspect of the present invention relates to a method for treating a vascular disease by introducing a DNA sequence encoding a TM protein or its variant into a segment of a blood vessel in vivo using a gutless adenovirus vector. Another aspect of the present invention is to provide a method to deliver a gutless adenovirus vector carrying a DNA sequence encoding a TM protein or its variant using a stent.

20 Claims, 7 Drawing Sheets

OTHER PUBLICATIONS

Salomaa, Veikko, et al., "Soluble thrombomodulin as a preidcctor of incident coronary heart disease and symptomless carotid artery atherosclerosis in the Atherosclerosis Risk in Communities (ARIC) Study: a case-cohort study," Lancet, vol. 353, pp. 1729-1734 (1999).

Palmer, R.M.J., et al., "Nitric oxide release accounts for the biological activity of endothelium-derived relaxing factor," Nature, vol. 327, pp. 524-526 (1987).

Kubes, P., et al., "Nitric oxide: An endogenous modulator of leukocyte adhesion," Proc. Natl. Acad. Sci. USA, vol. 88, pp. 4651-4655 (1991).

Steg, P. Gabriel, M.D., et al., "Reduction of Restenosis After Angioplasty in an Atheromatous Rabbit Model by Suicide Gene Therapy," Circulation, vol. 96, pp. 401-411 (1997).

Van Belle, Eric, et al., "Accelerated Endothelialization by Local Delivery of Recombinant Human Vascular Endothlial Growth Factor Reduces In-Stent Intimal Formation," Biochem. and Biophs. Res. Communications, vol. 235, pp. 311-316 (1997).

Salyapongse, A. Neil, M.D., et al., "Gene Therapy and Tissue Engineering," Tissue Engineering, vol. 26, No. 4, pp. 663-676 (1999).

Kon, T., et al., "Bone Morphogenetic Protein-2-Stimulates Differentiation of Cultured Spinal Ligament Cells from Patients with Ossification of the Posterior Longitudinal Ligament," Calcif. Tissue Int., vol. 60; pp. 291-296 (1997).

Kibbe et al. (J. Vasc. Surg. 34: 156-65, 2001).

He et al. (PNAS, 95: 2509-2514), 1998).

Marmur, J., et al., "Strand Separation and Specific Recombination in Deoxyribonucleic Acids: Biological Studies," *PNAS USA*, vol. 46, pp. 453-461 (1960).

Doty, P., et al., "Strand Separation and Specific Recombination in Deoxyribonucleic Acids: Physical Chemical Studies," *PNAS USA*, vol. 46, pp. 461-476 (1960).

Sambrook, J. Fritsch, et al., "Analysis of Genomic DNA by Southern Hybridization," *Molecular Cloning: A Laboratory Manual* (Cold Spring Harbor Lab. Press, Plainview, NY), vol. II, pp. 9.31-9.62 (1989).

Curiel, David T., "Strategies to Adapt Adenoviral Vectors for Targeted Delivery," *Ann NY Acad Sci* 886, pp. 158-171 (1991).

Haj-Ahmand, Yousef, et al., "Development of a Helper-Independent Human Adenovirus Vector and Its Use in the Transfer of the Herpes Simplex Virus Thymidine Kinase Gene," *J. Virol.* vol. 57, No. 1, 267-274 (1986).

Ragot, Thierry, et al., "Efficient adenivirus-mediated transfer of a human minidystrophin gene to skeletal muscle of *mdx* mice," *Nature*, vol. 361, pp. 647-650 (1993).

Howell, John McC., et al., "High-Level Dystrophin Expression after Adenovirus-Mediated Dystophin Minigene Transfer to Skeletal Muscle of Dystrophin Dogs: Prolongation of Expression with Immunosuppression," *Hum Gene Ther.*, vol. 9, pp. 629-634 (1998).

Parks, Robin J., et al., "A helper-dependent adenovirus vector system: Removal of helper virus by Cre-mediated excision of the viral packaging signal," *PNAS*, vol. 93, pp. 13565-13570 (1996).

Lieber, André, et al., "Recombinant Adenoviruses with Large Deletions Generated by Cre-Mediated Excision Exhibit Different Biological Properties Compared with First-Generation Vectors In Vitro and In Vivo," *J. Virol*, vol. 70, pp. 8944-8960 (1996).

Gossen, Manfred, et al., "Tight control of gene expression in mammalian cells by tetracycline-responsive promoters," *PNAS USA*, vol. 89, pp. 5547-5551 (1992).

Gossen, Manfred, et al., "Transcriptional Activation by Tetracyclines in Mammalian Cells," *Science*, vol. 268, pp. 1766-1769 (1995).

Kistner, Andreas, et al., "Doxycycline-mediated quantitative and tissue-specific control of gene expression in transgenic mice," *PNAS USA*, vol. 93, pp. 10933-10938 (1996).

No, David, et al., "Ecdysone-inducible gene expression in mammalian cells and transgenic mice," *PNAS USA*, vol. 93, pp. 3346-3351 (1996).

Wang, Yaolin, et al., "A regulatory system for use in gene transfer," *PNAS USA*, vol. 91, pp. 8180-8184 (1994).

Wang, Yaolin, et al., "Ligand-inducible and liver-specific target gene expression in transgenic mice," *Nat. Biotech.*, vol. 15, pp. 239-243 (1997).

Magari, Shannon R., et al., "Pharmacologic Control of a Humanized Gene Therapy System Implanted into Nude Mice," *J. Clin. Invest.*, vol. 100, No. 11, pp. 2865-2872 (1997).

Ye, Xuehai, et al., "Regulated Delivery of Therapeutic Proteins After in Vivo Somatic Cell Gene Transfer," *Science*, vol. 283, pp. 88-91 (1999).

Suzuki, Koji, et al., "Structure and expression of human thrombomodulin, a thrombin receptor on endothelium acting as a cofactor for protein C activation," *EMBO J.*, vol. 6, No. 7, pp. 1891-1897 (1987).

Dittman, William A., et al., "Human Thrombomodulin: Complete cDNA Sequence and Chromosome Localization of the Gene," *Biochemistry*, vol. 26, pp. 4350-4357 (1987).

Beauchamp, Cindy, et al., "Development of a FLP/frt Syste for Generating Helper-Dependent Adenoviral Vectors," *Molecular Therapy*, vol. 3, No. 5, pp. 809-815 (2001).

Umana, Pablo, et al., "Efficient FLPe recombinase enables scalable production of helper-dependent adenoviral vectors with negligible helper-virus contamination," *Nature Biotechnology*, vol. 19, pp. 582-585 (2001).

* cited by examiner

EX VIVO AND IN VIVO EXPRESSION OF THE THROMBOMODULIN GENE FOR THE TREATMENT OF CARDIOVASCULAR AND PERIPHERAL VASCULAR DISEASES

This application is a continuation-in-part application of U.S. Ser. No. 10/725,013, filed Dec. 2, 2003 (now U.S. Pat. No. 7,179,459, issued Feb. 20, 2007), which claims priority from U.S. Provisional Application Ser. No. 60/430,099, filed Dec. 2, 2002. The entirety of all of the aforementioned applications is incorporated herein by reference.

FIELD

The present invention is directed to methods and compositions for the treatment of cardiovascular and peripheral vascular diseases, and in particular, is directed to methods and compositions for ex vivo and in vivo expression of the thrombomodulin gene using gutless adenovirus vector.

BACKGROUND

Atherosclerosis is one of the chief causes of morbidity and mortality in the United States and many other countries of the world. (Zuckerbraun et al., Arch Surg. 137:854-861 [2002]; Kibbe et al., Circ Res. 86:829-33 [2000]). This process can result in limiting the flow of blood to the heart, kidneys and the peripheral vessels, to name a few. Current approaches to the treatment of lesions in the arteries include coronary artery by-pass graft (CABG) surgery and angioplasty with or without the placement of a stent. The latter may serve as a vehicle for drug delivery, as is currently being tested in clinical trials. A number of pharmacological agents that affect platelet function or provide anticoagulant properties have so far failed to reduce re-occlusion or intimal hyperplasia. (Kibbe et al., Circ Res. 86:829-33 [2000]).

Cardiovascular diseases, however, are the result of complex pathophysiologic processes that involve the expression of many proteins and molecules that can adversely affect the grafted vessel (Shears et al., J. Am Coll Surg., 187(3):295-306 [1998]; Ross et al., Nature, 362:801-9 [1993]). Approximately 15-30% of patients receiving vein grafts for coronary or peripheral vascular disease require follow-up treatment, either in the form of angioplasty or new grafts.

Thrombomodulin (TM) is an integral membrane glycoprotein expressed on the surface of endothelial cells (Sadler et al., Trhomb Haemost., 78:392-95 [1997]). It is a high affinity thrombin receptor that converts thrombin into a protein C activator. Activated protein C then functions as an anticoagulant by inactivating two regulatory proteins of the clotting system, namely factors Va and VI [I]a (Esmon et al., Faseb J., 9:946-55 [1995]). The latter two proteins are essential for the function of two of the coagulation proteases, namely factors IXa and Xa. TM thus plays an active role in blood clot formation in vivo and can function as a direct or indirect anticoagulant.

There are several other proteins or enzymes that have shown to reduce the process of intimal hyperplasia, whose evolution is the cause of late graft failure. For instance, Nitric oxide synthase, an enzyme expressed by endothelial cells has been shown in animal models to inhibit intimal hyperplasia, especially the inducible enzyme (iNOS) (Salmaa et al., Lancet, 353:1729-34 [1999]; Palmer et al., Nature, 327:524-26 [1987]; Kubes et al., PNAS USA., 88:4651-5 [1991]).

Animal studies shown that cytoxic gene transfection utilizing the Herpes Simplex Virus thymydine kinase gene delivered via an adenoviral vector was able to inhibit intimal hyperplasia (Steg et al., Circulation, 96:408-11 [1997]). Vascular endothelial growth factor (VEGF), basic fibroblast growth factor (bFGF) and platelet derived growth factor (PDGF) have all been shown to promote reendothelization and enhance the healing of vascular injury and help limit intimal hyperplasia. (Ban Bellle et al., Biochem Biophs Res Commun., 235:311-16 [1997]; Salyapongse et al., Tissue Engineering 26(4):663-76 [1999]).

A gene therapy approach is currently under clinical investigation. It involves the injection, directly into heart muscles, of an adenoviral vector delivery system containing the gene for the expression of vascular endothelial growth factor (VEGF). This is being tested in patients whose coronary vessels are not amenable to standard grafting procedures. However, some recent adverse clinical events demonstrated that injection of large quantities of adenovirus vectors is associated with significant risks. Accordingly, there still exists a need for a method to effectively introduce therapeutic genes, such as TM, into vascular tissues.

SUMMARY

One aspect of the present invention relates to methods for treating a vascular disease in a mammal. In one embodiment, the method comprises the steps of: evacuating a clot from a blood vessel in the mammal, isolating a segment of the blood vessel around the evacuation site, and infecting the segment of blood vessel in vivo using a gutless adenoviral vector comprising a polynucleotide encoding a thrombomodulin protein or its variant, wherein the thrombomodulin protein or its variant is expressed in a amount sufficient to reduce re-occlusion or intimal hyperplasia in the infected blood vessel, and wherein said gutless adenoviral vector comprises the nucleotide sequence of SEQ ID NO:13 or SEQ ID NO:15.

In another embodiment, the method comprises the step of administering a therapeutically effective amount of a gutless adenovirus vector into a segment of a blood vessel in vivo using a stent, wherein the gutless adenovirus vector comprises the nucleotide sequence of SEQ ID NO:13 or SEQ ID NO:15, and is capable of expressing a thrombomodulin protein or a variant of the thrombomodulin protein.

In another embodiment, the method comprises the step of administering intravenously an effective amount of a gutless adenoviral vector comprising a polynucleotide encoding a thrombomodulin protein or its variant, wherein the gutless adenoviral vector comprises the nucleotide sequence of SEQ ID NO:13 or SEQ ID NO:15.

Another aspect of the present invention pertains to a gutless adenovirus vector comprising a polynucleotide encoding a thrombomodulin protein having the amino acid sequence of SEQ ID NO:2, a regulatory element operably linked to the polynucleotide sequence; and a stuffer comprising the nucleotide sequence of SEQ ID NO:13 or SEQ ID NO:15.

Yet another aspect of the present invention pertains to a pharmaceutical composition for treating a vascular disease, comprising the gutless adenovirus vector described above and a pharmaceutically acceptable carrier.

DETAILED DESCRIPTION

Figure 1:
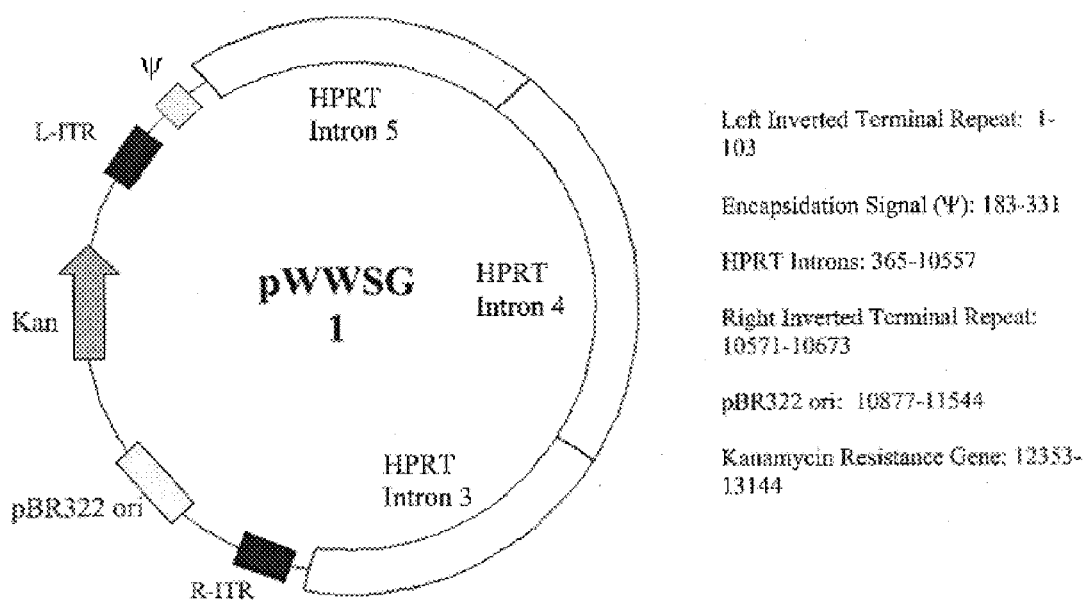
FIG. 1 is a schematic drawing of an embodiment of the backbone shuttle vector pShuttle-ITR-HPRT.

The practice of the present invention will employ, unless otherwise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

The primary object of the present invention is to provide methods for treating vascular diseases using gene delivery technologies. One aspect of the present invention relates to a method for treating a vascular disease by introducing a DNA sequence encoding a TM protein or its variant into a segment of a blood vessel in vitro using a gutless adenovirus vector and grafting the virus-treated vessel in a patient affected by a vascular disease. The virus-mediated TM expression reduces re-occlusion and intimal hyperplasia in the grafted vessel. This ex vivo approach eliminates the need to inject a large quantity of virus into a patient and hence significantly reduces the viral-related toxicity.

In one embodiment, the method is used for a coronary artery bypass. In another embodiment, the method is used for the treatment of peripheral vascular diseases. In yet another embodiment, the method is used for the maintenance of vein access in renal dialysis patients.

Another object of the present invention is to provide a method to deliver a gutless adenovirus vector carrying a DNA sequence encoding a TM protein or its variant using a stent. The viral vector is embedded in the stent and is released only at a treatment site. Since the viral infection is restricted at the treatment site and the surrounding area, only a small amount of the virus is needed and the virus-related toxicity is reduced.

Yet another object of the present invention pertains to a gutless adenovirus carrying a TM gene. In one embodiment, the gutless adenovirus, which contains a regulatory element operably linked to a DNA sequence encoding a TM protein or its variant and a polyA sequence, is produced using a novel shuttle vector containing a pBR322 replication origin, a selection marker, an adenovirus left inverted terminal repeat, an adenovirus encapsidation signal, a stuffer sequence, and an adenovirus left inverted terminal repeat.

In one embodiment, the regulatory element is a constitutive promoter such a CMV promoter and RSV promoter. In another embodiment, the regulatory element is an inducible promoter.

The forth object of the present invention is to provide a pharmaceutical composition which comprises an effective amount of gutless adenovirus carrying a TM gene of the present invention and a pharmaceutically acceptable carrier. Such compositions may be liquids or lyophilized or otherwise dried formulations and may further include diluents of various buffer content, (e.g., Tris-HCl, acetate, phosphate) pH and ionic strength, additives such as albumin and gelatin to prevent absorption to surfaces, detergents (e.g., Tween 20, Tween 80, Pluronic F68, bile acid salts), solubilizing agents (e.g., glycerol, polyethylene glycerol); anti-oxidants (e.g., ascorbic acid, sodium metabisulfite), and preservatives (e.g. Thimerosal, benzyl alcohol, parabens).

In describing the present invention, the following terms will be employed, and are intended to be defined as indicated below.

"Gene transfer" or "gene delivery" refers to methods or systems for reliably introducing a particular nucleotide sequence (e.g., DNA) into targeted cells. The introduced nucleotide sequences may persist in vivo in episomal forms or integrate into the genome of the target cells. Gene transfer provides a unique approach for the treatment of acquired and inherited diseases, and a number of systems have been developed in the art for gene transfer into mammalian cells. See, e.g., U.S. Pat. No. 5,399,346.

As used herein, the term "effective amount" refers to a level of infection which brings about at least partially a desired therapeutic or prophylactic effect in an organ or tissue infected by the method of the present invention. The infection with an effective amount of the vector carrying genetic material of interest can then result in the modification of the cellular activities, e.g., a change in phenotype, in an organ or a tissue that has been infected by the method of the present invention. In a preferred embodiment, the infection with an effective amount of the vector carrying genetic material of interest results in modulation of cellular activity in a significant number of cells of an infected organ or a tissue.

A gene transfer "vector" refers to any agent, such as a plasmid, phage, transposon, cosmid, chromosome, liposome, DNA-viral conjugates, RNA/DNA oligonucleotides, virus, bacteria, etc., which is capable of transferring gene sequences into cells. Thus, the term includes cloning and expression vehicles including "naked" expression vectors, as well as viral and non-viral vectors. A vector may be targeted to specific cells by linking a target molecule to the vector. A targeting molecule is any agent that is specific for a cell or tissue type of interest, including for example, a ligand, antibody, sugar, receptor, or other binding molecule. The invention is also intended to include such other forms of vectors which serve equivalent functions and which become known in the art subsequently hereto.

The term "expression control element" or "regulatory element" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a, DNA regulatory sequence that is sufficient for RNA polymerase recognition, binding and transcription initiation. Additionally, a promoter includes sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, muscle creatine kinase (MCK) promoter, myosin promoter, (α-actin promoter) and the like.

The term "transduction" denotes the delivery of a DNA molecule to a recipient cell either in vivo or in vitro, via a replication-defective viral vector, such as via a recombinant adenovirus.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as the function to direct the expression thereof. Thus, for example, intervening untranslated yet transcribed sequences can be present between a promoter sequence and the coding sequence and the promoter sequence can still be considered "operably linked" to the coding sequence.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *PNAS USA* 46:453 (1960) and Doty et al., *PNAS USA* 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "Tm." The Tm. of a particular nucleic acid duplex under specified conditions is the temperature at which on average half of the base pairs have disassociated. The equation for calculating the Tm. of nucleic acids is well known in the art.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data bands, or in a Southern hybridization experiment under, for example, stringent conditions as defined for that particular system. Suitable conditions include those characterized by a hybridization buffer comprising 0.9M sodium citrate ("SSC") buffer at a temperature of about 37° C. and washing in SSC buffer at a temperature of about 37° C.; and preferably in a hybridization buffer comprising 20% formamide in 0.9M SSC buffer at a temperature of about 42° C. and washing in 0.2×SSC buffer at about 42° C. Stringency conditions can be further varied by modifying the temperature and/or salt content of the buffer, or by modifying the length of the hybridization probe as is known to those of skill in the art. Defining appropriate hybridization conditions is within the skill of the art. See e.g., Sambrook, J. Fritsch, E. J., & Maniatis, T. (1989) *Molecular Cloning: A Laboratory Manual* (Cold Spring Harbor Lab. Press, Plainview, N.Y.).

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The terms "nucleic acid substrate" and nucleic acid template" are used herein interchangeably and refer to a nucleic acid molecule which may comprise single- or double-stranded DNA or RNA.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "native thrombomodulin" refers to both the natural protein and soluble peptides having the same characteristic biological activity of membrane-bound or detergent solubilized (natural) thrombomodulin. These soluble peptides are also referred to as "wild-type" or "non-mutant" analog peptides. Biological activity is the ability to act as a receptor for thrombin, increase the activation of protein C, or other biological activity associated with native thrombomodulin. Oxidation resistant TM analogs are these soluble peptides that in addition to being soluble contain a specific artificially induced mutation in their amino acid sequence.

The term "thrombomodulin variant" is a polypeptide that differs from a native thrombomodulin polypeptide in one or more substitutions, deletions, additions and/or insertions, such that the bioactivity of the native thrombomodulin polypeptide is not substantially diminished or enhanced. In other words, the bioactivity of a thrombomodulin variant may be enhanced or diminished by, less than 50%, and preferably less than 20%, relative to the native protein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the—and/or C-terminal of the mature protein.

Preferably, a thrombomodulin variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the bioactivity, secondary structure and hydropathic nature of the polypeptide.

Thrombomodulin variants preferably exhibit at least about 70%, more preferably at least about 90% and most preferably at least about 95% sequence homology to the original thrombomodulin polypeptide.

A thrombomodulin variant also includes a thrombomodulin polypeptides that is modified from the original thrombomodulin polypeptides by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cysteine, formation of pyroglutamate, formulation, gammacarboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

Adenovirus Vectors:

The genome of an adenovirus can be manipulated such that it encodes and expresses a gene product of interest but is inactivated in terms of its ability to replicate in a normal lyric viral life cycle (Curie D T, Ann N Y Acad Sci 886, 158-171 [1991]). Suitable adenoidal vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium, endothelial cells and muscle cells. Additionally, introduced adenoidal DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoidal genome for foreign DNA is large (up to 8 kilobases) relative to other gene delivery vectors (Haj-Ahmand et al. J. Virol. 57, 267-273 [1986]). Most replication-defective adenoidal vectors currently in use are deleted for all or parts of the viral E1 and E3 genes but retain as much as 80% of the adenoidal genetic material. Adenoidal vectors deleted for all viral coding regions are also described by Kochanek et al. and Chamberlain et al. (U.S. Pat. Nos. 5,985,846 and 6,083,750).

Adenovirus vectors have been successfully tested in a number of animal models (Ragot et al. Nature 361, 647-650 [1993]; Howell et al. Hum Gene Ther 9, 629-634 [1998]). Nonetheless, the toxicity and immunogenicity remain major hurdles to overcome before the adenovirus vectors can be safely used in humans.

Adenoviruses (Ad) are double-stranded DNA viruses with a linear genome of about 36 kb. The adenovirus genome is complex and contains over 50 open reading frames (ORFs). These ORFs are overlapping and genes encoding one protein are often embedded within genes coding for other Ad proteins. Expression of Ad genes is divided into an early and a late phase. The early genes comprise E1a, E1b, E2a, E2b, E3 and E4, which are transcribed prior to replication of the viral genome. The late genes (e.g., L1-5) are transcribed after replication of the viral genome. The products of the late genes are predominantly components of the virion, as well as proteins involved in the assembly of virions.

The so-called "gutless" rAd vectors contain a minimal amount of adenovirus DNA and are incapable of expressing any adenovirus antigens (hence the term "gutless"). The gutless rAd vectors provide the significant advantage of accommodating large inserts of foreign DNA while completely eliminating the problem of expressing adenoviral genes that result in an immunological response to viral proteins when a gutless rAd vector is used in gene therapy. Methods for producing gutless rAd vectors have been described, for example, in U.S. Pat. No. 5,981,225 to Kochanek et al., and U.S. Pat. Nos. 6,063,622 and 6,451,596 to Chamberlain et al; Parks et al., PNAS 93:13565 (1996) and Lieber et al., J. Virol. 70:8944-8960 (1996).

The "inverted terminal repeats (ITRs) of adenovirus" are short elements located at the 5' and 3' termini of the linear adenoviral genome, respectively and are required for replication of the viral DNA. The left ITR is located between 1-130 bp in the Ad genome (also referred to as 0-0.5 mu). The right ITR is located from about 3,7500 bp to the end of the genome (also referred to as 99.5-100 mu). The two ITRs are inverted repeats of each other. For clarity, the left ITR or 5' end is used to define the 5' and 3' ends of the ITRs. The 5' end of the left ITR is located at the extreme 5' end of the linear adenoviral genome; picturing the left ITR as an arrow extending from the 5' end of the genome, the tail of the 5' ITR is located at mu 0 and the head of the left ITR is located at about 0.5 mu (further the tail of the left ITR is referred to as the 5' end of the left ITR and the head of the left ITR is referred to as the 3' end of the left ITR). The tail of the right or 3' ITR is located at mu 100 and the head of the right ITR is located at about mu 99.5; the head of the right ITR is referred to as the 5' end of the right ITR and the tail of the right ITR is referred to as the 3' end of the right ITR. In the linear adenoviral genome, the ITRs face each other with the head of each ITR pointing inward toward the bulk of the genome. When arranged in a "tail to tail orientation" the tails of each ITR (which comprise the 5' end of the left ITR and the 3' end of the right ITR) are located in proximity to one another while the heads of each ITR are separated and face outward.

The "encapsidation signal of adenovirus" or "adenovirus packaging sequence" refers to the v sequence which comprises five (AI-AV) packaging signals and is required for encapsidation of the mature linear genome; the packaging signals are located from about 194 to 358 bp in the Ad genome (about 0.5-1.0 mμ).

One aspect of the present invention relates to a viral backbone shuttle vector for the construction of gutless rAd vectors. In one embodiment, the viral backbone shuttle vector of the present invention contains a left and a right inverted terminal repeats of adenovirus, an encapsidation signal (ψ) of adenovirus, a pBR322 replication origin, a kanamycin resistance gene, and a stuffer sequence, which is the hypoxanthine phosphoribosyltransferase (HPRT) intron fragment with an approximately 10 kb. (SEQ ID NO: 1).

The viral backbone shuttle vector of the present invention contains multiple restriction endonuclease sites for the insertion of a foreign DNA sequence of interest. In one embodiment, the viral backbone shuttle vector contains seven unique cloning sites where the foreign DNA sequence can be inserted by molecular cloning techniques that are well known in the DNA cloning art. The foreign DNA sequence of interest typically comprises cDNA or genomic fragments that are of interest to transfer into mammalian cells. Foreign DNA sequence of interest may include any naturally occurring or synthetic DNA sequence. The foreign DNA may be identical in sequence to naturally-occurring DNA or may be mutated relative to the naturally occurring sequence. The foreign DNA need not be characterized as to sequence or function.

The size of foreign DNA that may be included in the shuttle vector will depend upon the size of the rest of the vector. If necessary, the stuffer sequence may be removed to adapt large size foreign DNA fragment. The total size of foreign DNA may vary from 1 kb to 35 kb. Preferably, the total size of foreign DNA is from 15 kb to 35 kb.

The foreign DNA may encode protein, or contain regulatory sites, including but not limited to, transcription factor binding sites, promoters, enhancers, silencers, ribosome binding sequences, recombination sites, origins of replication, sequences which regulate RNA stability and polyadenylation signals. The promoters used may vary in their nature, origin and properties. The choice of promoter depends in fact on the desired use and on the gene of interest, in particular. Thus, the promoter may be constitutive or regulated, strong or weak, ubiquitous or tissue/cell-specific, or even specific of physiological or pathophysiological states (activity dependent on the state of cell differentiation or the step in the cell cycle). The promoter may be of eukaryotic, prokaryotic, viral, animal, plant, artificial or human, etc., origin. Specific examples of promoters are the promoters of the genes PGK, TK, GH, α-EF1, APO, CMV, RSV etc. or artificial promoters, such as those for p53, E2F or cAMP.

In one embodiment, the viral backbone shuttle vector of the present invention comprises at least 15 contiguous bases of SEQ ID NO: 1, preferably comprises at least 90 contiguous bases of SEQ ID NO: 1, more preferably comprises at least 300 contiguous bases of SEQ ID NO: 1, and most preferably comprises 3000 or more contiguous bases of SEQ ID NO: 1.

One aspect of the present invention relates to a gutless adenoviral vector that carries a DNA sequence encoding a native TM protein or a variant of a TM protein. In one embodiment, the native TM protein is a human TM protein having the amino acid sequence recited in SEQ ID NO:2. In one embodiment, the DNA sequence is controlled by a regulatory element. In on embodiment, the regulatory element is a constitutive promoter such as the CMV promoter or RSV promoter. In another embodiment, the DNA sequence is controlled by a regulatable expression system. Systems to regulate expression of therapeutic genes have been developed and incorporated into the current viral gene delivery vectors. These systems are briefly described below:

Tet-on/off system. The Tet-system is based on two regulatory elements derived from the tetracycline-resistance operon of the *E. coli* Tn 10 transposon: the tet repressor protein (TetR) and the Tet operator DNA sequence (tetO) to which TetR binds. The system consists of two components, a "regulator" and a "reporter" plasmid. The "regulator" plasmid encodes a hybrid protein containing a mutated Tet repression (tetr) fused to the VP 16 activation domain of herpes simplex virus. The "reporter" plasmid contains a tet-responsive element (TRE), which controls the "reporter" gene of choice. The tetr-VP16 fusion protein can only bind to the TRE, therefore activate the transcription of the "reporter" gene, in the presence of tetracycline. The system has been incorporated into a number of viral vectors including retrovirus, adenovirus (Gossen and Bujard, *PNAS USA* 89: 5547-5551, [1992]; Gossen et al., *Science* 268: 1766-1769, [1995]; Kistner et al., *PNAS USA* 93: 10933-10938, [1996]).

Ecdysone system. The Ecdysone system is based on the molting induction system found in *Drosophila*, but modified for inducible expression in mammalian cells. The system uses an analog of the *drosophila* steroid hormone ecdysone, muristerone A, to activate expression of the gene of interest via a heterodimeric nuclear receptor. Expression levels have been reported to exceed 200-fold over basal levels with no effect on mammalian cell physiology (No et al., *PNAS USA* 93: 3346-3351, [1996]).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GAL4 and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., *PNAS USA* 93: 8180-8184, [1994]; Wang et al., *Nat. Biotech* 15: 239-243, [1997]).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been used to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral vectors. Long-term regulatable gene expression has been achieved in both mice and baboons (Magari et al., *J. Clin. Invest.* 100: 2865-2872, [1997]; Ye et al., *Science* 283:88-91, [1999]).

Ex Vivo and In Vivo Thrombomodulin Gene Transfer

The instant invention uses a gutless adenovirus vector to express a native thrombomodulin protein or a variant of the thrombomodulin protein at a vessel graft or angioplasty site to prevent or reduce re-occlusion and intimal hyperplasia. The amino acid sequence of human thrombomodulin (SEQ ID NO: 2) and the DNA sequence encoding human thrombomodulin (SEQ ID NO: 3) have been reported (Suzuki et al. *EMBO J.* 6:1891-1897, [1987]).

In one embodiment, the in vivo expression of thrombomodulin or a thrombomodulin variant is used for the treatment of atherosclerotic cardiovascular disease (CVD). Though venous grafts can be used for bypass surgeries, the veins eventually, become occluded by thrombosis resulting the recurrence of the diseases. In this embodiment, TM gene delivery is used in coronary artery bypass grafting, and vascular graft prostheses to block thrombosis. Specifically, TM gene is introduced into a segment of blood vessel in vitro using a gene transfer vector.

TM gene delivery can be also used for the reduction of no-intima formation, for the prevention of atherosclerosis; for the prevention of myocardial infarction and for the inhibition of fibrinolysis in hemophilic plasma. TM gene transfer at the site of thrombus formation is potent approach to reverse these vascular diseases.

In another embodiment, in vivo TM expression is achieved by embedding a gene transfer vector in a stent which is placed at the treatment site following percutaneous transluminal coronary angioplasty, peripheral artery angioplasty, thrombectomy, or an intravascular stenting procedure.

In another embodiment, the in vivo expression of thrombomodulin, or a thrombomodulin variant is used for the treatment of end stage renal failure (ESRD). ESRD patients often exhibit decreased antithrombotic activity due to low TM levels. In such patients, enhanced in vivo TM gene expression can be potentially very useful.

In another embodiment, the in vivo TM expression is achieved by administering a gene transfer vector to a mammal intravenously (i.v.), intramuscularly (i.m.), intraperitoneally (i.p.) or subcutaneously. For adenoviral and AAV vectors, intravenous administration often lead to viral infection of hepatocytes and transgene expression in the liver.

The present invention is further illustrated by the following examples which should not be construed as limiting. The contents of all references, patents and published patent applications cited throughout this application, as well as the Figures and Tables are incorporated herein by reference.

EXAMPLE 1

Construction of Gutless Viral Backbone Shuttle Vector pShuttle-ITR-HPRT 1.1 Creation of pShuttle-ITR An embodiment of a gutless viral backbone shuttle vector pShuttle-ITR-HPRT is shown in FIG. 1. Sequence portion containing R-ITR, PBR322 ori, Kan, L-ITR, and encapsidation signal was obtained from the pAdEasy® system from STRATEGENE®. At bp 3667 of the original pShuttle sequence, there is a BamHI site just beyond the R-ITR. PCR primers were designed to include the BamHI site and then were to create an EcoRI site at the end of the R-ITR. The R-ITR was PCR replicated and then digested with BamHI and EcoRI to create sticky ends. The viral backbone was then cut with both BamHI and EcoRI. The BamHI cut the backbone at bp 3667 and there was also an EcoRI site inside the MCS at bp 377. The backbone portion of the plasmid was then gel purified and the PCR replicated R-ITR was recloned into position. This essentially puts the L-ITR, encapsidation signal, MCS, and R-ITR all in close proximity to each other.

1.2 Creation of pShuttle-ITR-HPRT

Insertion of the HPRT introns was a two step cloning process. First, the viral backbone pShuttle-ITR was digested with EcoRI and XbaI, both enzyme sites are in the MCS. The HPRT source was also digested with EcoRI and XbaI yielding a 7477 bp fragment that was cloned into the EcoRI/XbaI digested viral backbone. Then the HPRT source was digested with only XbaI yielding a 2715 bp fragment. One of the XbaI sites in this cut is the same XbaI site that was cut from the EcoRI/XbaI double digest in step 1. The viral backbone was cut with only XbaI and the 2715 bp fragment was inserted.

Overall, from the HPRT source, the HPRT stuffer sequence is inserted into the viral backbone in reverse orientation, hence intron 5, then 4, then 3. The 2715 bp fragment was inserted and checked to follow the original source sequence. The new plasmid is designated as pShuttle-ITR-HPRT (SEQ ID NO:1)

EXAMPLE 2

Construction and Preparation of Gutless Viral Shuttle Vector Carrying Human Thrombomodulin or lacZ Gene 2(a) Construction and Preparation of Gutless Viral Shuttle Vector Carrying Human Thrombomodulin Gene 2(a)-1 Creation of pCMV-hTM The insertion of hTM into the gutless adenovirus backbone first required the creation of a CMV-hTM expression cassette. The intermediate vector used was pcDNA3.1/Zeo(+) (Invitrogen). A CMV promoter is available commercially and a CMV promoter was cloned into the multiple cloning sites (MCS) at the XbaI/EcoRV restriction enzyme site locations. The CMV from ps5 was removed using XbaI/EcoRV. pcDNA3.1/Zeo(+) was cleaved inside the MCS using both XbaI and EcoRV as well. The CMV promoter was then ligated. Due to the location of the enzyme sites in the MCS, the CMV promoter (SEQ ID NO:4) was inserted in a backwards orientation relative to the pcDNA3.1/Zeo (+) plasmid. The human TM cDNA (SEQ ID NO:5) was obtained from Dr. Sadler (Dittman et al., *Biochemistry*, 26(14):4350-4357

[1987]) which the sequence was also submitted to ATCC and to GenBank. The human TM gene was removed from the plasmid using EcoRI and inserted into pcDNA3.1/Zeo(+), also in the reverse orientation to pcDNA3.1/Zeo(+) downstream of the inserted CMV promoter.

2(a)-2 Creation of pShuttle-ITR-HPRT-CMV-TM

The expression cassette in pCMV-hTM was removed by digesting with PmeI. The gutless adenovirus backbone pshuttle-ITR-HPRT was linearized using SmaI which cuts the plasmid at bp 381. The CMV-hTM cassette was ligated to the gutless virus in the forwards orientation. Sequence of the expression cassette (from PmeI site to PmeI site) is shown in SEQ ID NO:6. The new plasmid is designated as pShuttle-ITR-HPRT-CMV-TM.

2(a)-3 Creation of pTMadap

The following linker containing a BstEII and SfiI site was inserted into the BstEII and Bsu36I sites of pShuttle-ITR-HPRT-CMV-TM, resulting in the vector pTMadap (SEQ ID NO:7).

```
                                              (SEQ ID NO:8)
5'-gtaacactgg cccaggaggc ctttctggtg acccc-3'

(SEQ ID NO:9)
3'-tgacc gggtcctccg gaaagaccac tggggatt-5'
```

Creation of pTMadap-stuffer1

Based on the published sequence HSU71148 of the human X chromosome region q28 the following PCR primers were synthesized:

```
Forward:
5' TAGTTCCTTCTGCCTGGAATAC 3'    (SEQ ID NO: 10)

Reverse:
5' CAAGTCACAAGGATGGACTACA 3'    (SEQ ID NO: 11)
```

Amplification of a human DNA sample resulted in the amplification of a 18524 bp DNA fragment (stuffer 1, SEQ ID NO: 12). Stuffer 1 was cut with the restriction enzymes BstEII and SfiI and the resulting fragment of approximately 18371 bp was inserted into the BsteII and SfiI sites of pTMadap, resulting in pTMadap-stuffer1.

2(a)-4 Creation of pTMadap-stuffer1-short

To reduce the size of the stuffer1 fragment in pTMadap-stuffer1, pTMadap-stuffer1 was digested with SanDI and BstEII and the resulting DNA ends were modified by a fill-in reaction with Klenow. Re-ligation resulted in the 25207 bp vector pTMadap-stuffer1-short. The sequence of stuffer1-short fragment is shown in SEQ ID NO:13.

2(a)-5 Creation of pTMadap-stuffer1-short-stuffer2

The plasmid p2-2 (SEQ ID NO: 14, obtained from GenBank) was cut with NotI and the resulting fragment of approximately 5954 bp (stuffer 2, SEQ ID NO: 15) was inserted into the NotI site of pTMadap-stuffer1short, resulting in pTMadap-stuffer1-short-stuffer2.

2(a)-6 Removal of PacI Site from pTMadap-stuffer1short-stuffer2

Figure 2:
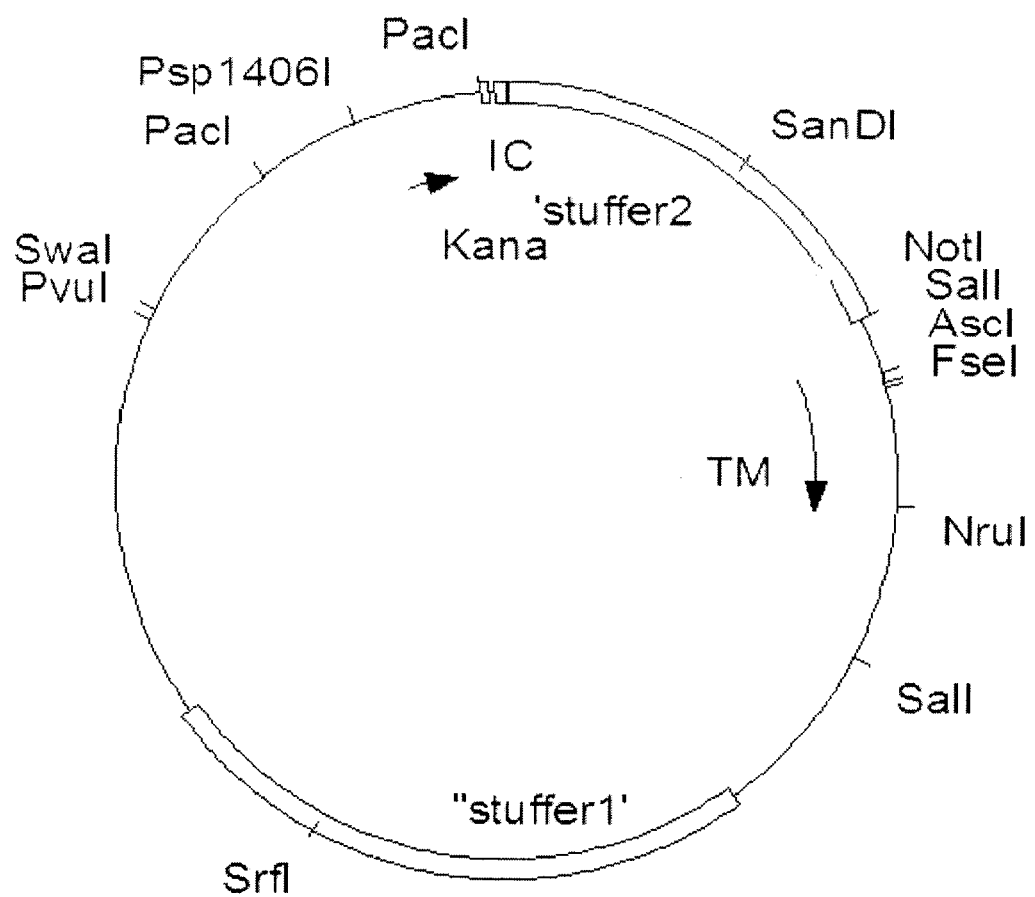
FIG. 2 is a schematic drawing of an embodiment of the full length backbone vector pTM-final.

Plasmid pTMadap-stuffer1-short-stuffer2 was cut with AclI and BsiW1. The resulting 28790 bp fragment was isolated from gel. pShuttle-ITR-HPRT (SEQ ID NO:1) was cut with AclI and Acc65I. The resulting 1966 bp fragment was ligated into the isolated 28790 bp fragment, resulting in the full length backbone vector pTM-final (FIG. 2 and SEQ ID NO: 16).

2(b) Construction and Preparation of Gutless Viral Shuttle Vector Carrying LacZ Gene The insertion of LacZ also required creation of an intermediate vector to create the expression cassette. pcDNA3.1/Zeo (+) was again used. First, a portion of the vector from the end of the MCS, restriction enzyme site ApaI, to the beginning of the SV40 poly A, restriction site NaeI, was removed and the vector relegated to itself. Then the LacZ gene was inserted into the vector MCS using NotI/XbaI. The expression cassette, containing CMV promoter, LacZ gene, and SV40 poly A, was removed using NruI/SalI retraction enzymes and blunt-end cloned into the gutless adenovirus at the SmaI restriction enzyme site.

EXAMPLE 3

Preparation of Gutless Adenovirus Carrying Human Thrombomodulin Gene (Gutless Ad.hTM)

The gutless Ad.hTM was prepared according to the following protocol:

1. Linearize pTM-final by digestion with PacI. The completeness of the digestion is confirmed by electrophoresis using a small aliquot of the digestion product. It's not necessary to gel purify the digested pTM-final for transfection described in step 2).

2. Transfect 293FLP cells grown in a 60 mm dish at about 80% confluence with about 5 μg of PacI-digested pTM-final using lipofectamine. 293FLP cells are 293 cells engineered to express the flp gene product, which recognizes the FRS flanking the encapsidation signal and cleaves out the encapsidation signal thereby not allowing helper-viral DNA to be packaged. (Beauchamp et al., *Molecular Therapy*, 3(5):809-815 [2001]; Umana et al., *Nature Biotechnology*, 19:582-585 [2001]).

3. Twenty-four hours after the transfection, infect the cells with helpervirus H10 in 2% DMEM-F12 at a multiplicity of infection (MOI) of 10.

4. Remove the cells from the plate (preferably with a cell scraper) after the appearance of cytopathic effect (CPE), place the cells in a sterile 15 ml tube, and lyse the cells by three freeze-and-thaw cycles. Precipitate the cell debris by spinning the lysate for 5 minutes at 4000 rpm and harvest the supernatant. The supernatant is designated as P0 (passage number 0) supernatant.

5. Infect 293FLP cells in two T75 flask at 80% confluency with 4 ml of P0 supernatant and with the helpervirus at MOI of 1.

6. Continue passaging virus in the manner described in steps 4 and 5 until passage 6 and confirm that helpervirus is added at an MOI of 1 at each passage.

7. Add the P6 supernatant to 8 T500 flasks containing 293FLP cells at 80% confluency and infect the cells with the helpervirus at a MOI of 1.

8. Following CPE, harvest the cells into 500 ml sterile tubes. Centrifuge the cell suspension at 4500 rpm, 4° C. for 10 minutes.

9. Resuspend the cell pellet in 2% DMEM-F12 (the pellet can be stored at −80° C. at this stage).

10. Freeze-thaw the resuspended cell pellet three times. Spin down the cell debris by centrifugation at 4000 rpm, 4° C. for 10 minutes.

11. Transfer the supernatant, which contains the released virus, to a fresh sterile culture tube and subject the supernatant to a second round of centrifugation to further remove cell debris.

12. Transfer the supernatant to a fresh sterile tube. The virus is ready for CsCl-purification.

13. To purify the virus, ultra-clear SW41 (Beckman) tubes were prepared by soaking in Ultra Pure Water, then 70% ETOH. Cotton swabs (one swab for each tube) were used to completely dry out the tube, and two tubes were used per sample.

14. Preparation of the first gradient: 2.5 mL CsCl—Density 1.25, and 2.5 mL CsCl—Density 1.40. Place the 1.25 density CsCl into the Beckman tubes first. Underlay slowly the high density, 1.40 CsCl using a sterile pasteur pipette, and overlay an equal amount (in mL) of CVL, about 4.25 ml/tube. Samples were centrifuged in a SW41 rotor with speed: 35,000 rpm at 20° C. for 1 hour and with acceleration: 1 and deceleration: 4. The lower opalescent band was collected using 1 or 3 mL syringe with green cap needles.

Preparation of second gradient: CsCl was prepared to density 1.33 g/ml. Two fresh ultra-clear tubes were placed 8 mL of CsCl and overlay the band just recovered after the first spin. (To equilibrate the tubes, measure before the volume of the recovered band and divide equally in the 2 tubes). Samples were centrifuged at the conditions above for 18 hours. The opalescent band was recovered and collected in a sterile eppendorf tube. (From this moment, keep the tube always on ice). Samples were dialyze with dialysis buffer: (1) 10× Dialysis Buffer: 100 mM Tris—pH 7.4, 10 mM $MgCl_2$; (2) 1× Dialysis Buffer (2 Liters): 400 mL Glycerol, 200 mL 10× Dialysis Buffer 140 mL, and Ultra Pure Water. The dialyzed samples were immediately stored at −70° C.

(c) Determination of Virus Titer

BioRad protein estimation kit was used with 1:5 diluting, and placing 1 ml in each disposable cuvette. Standards were set up at 0, 1, 2, 5, 10, and 15 μg/ml. (BSA is fine). Sample cuvettes were prepared using 1-10 μl of sample, depending on estimate of titer. (Sample OD must be within the linear range of the standard line.) OD was taken at 595λ and formula of the line was calculated from standards. The protein concentration of the samples was calculated using this formula. The following formula was used to convert protein concentration to titer: $[12.956+224.15 \, (\mu g/ml)] \times 10^8$.

EXAMPLE 4

Figure 3:
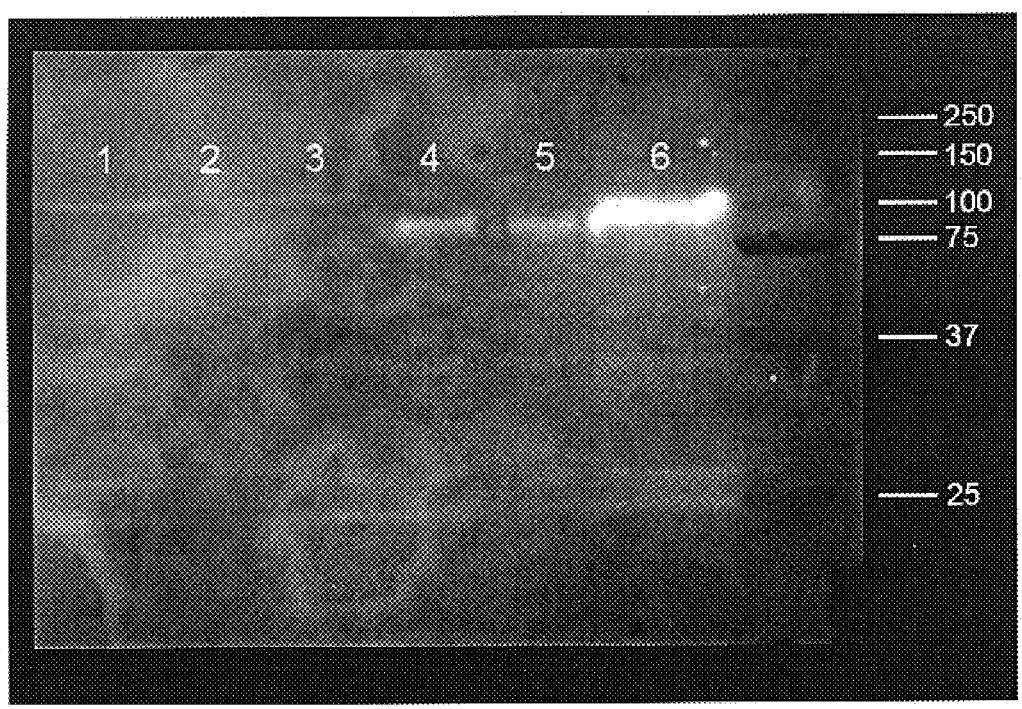
FIG. 3 is a picture of a Western blot showing hTM expression in HEK 293 cells transfected with pTM-final (the full size backbone of gutless Ad.hTM). Lanes 1-3: lysate from control cells; Lanes 4-6, lysate from pTM-final transfected cells.

Expression of Human Thrombomodulin (hTM) In Vitro (A) Expression of hTM in HEK 293 Cells Transfected with pTM-Final HEK 293 cells were cultured in a 6 well cluster and transfected with 1 μg of pTM-final. After 24 hours, the cells were washed with PBS and lysed in 125 μl RIPA buffer with protease inhibitors Protein samples (16 μl) were separated on 7.5% polyacrylamide/SDS gel and transferred to nitrocellulose membrane. Primary antibody TM (c-17) (1:2000, Santa Cruz) and secondary antibody Polyclonal Rabbit Anti-Goat immunoglobulins/HRP (1:4000, DakoCytomation) was used to detect the proteins. As shown in FIG. 3, hTM expression was detectable in cells transfected with pTM-final.

The RIPA buffer was prepared according the following recipe: mixing 100 μl Igepal α-630, 50 mg sodium deoxycholate, 500 μl 20% SDS, 10 mM β-mercapto ethanol, and 1 ml 10× PBS, and add water to a final volume of 10 ml at room temperature. A cocktail of protease inhibitors containing 11.5 μl PMSF (from 34.8 mg/ml in isopropanol, 64 μl Benzamidine (from 15.6 mg/ml stock), 100 μl sodium orthovanadate (100 mM), 5 μl pepstadine (from 1 mg/ml stock), 1 μl leupeptine (from 5 mg/ml stock), and 1 μl aprotin (from 5 mg/ml stock) was added to the RIPA buffer immediately before use.

(B) Expression of hTM in P2 Lysate of 293FLP Cells

Figure 4:
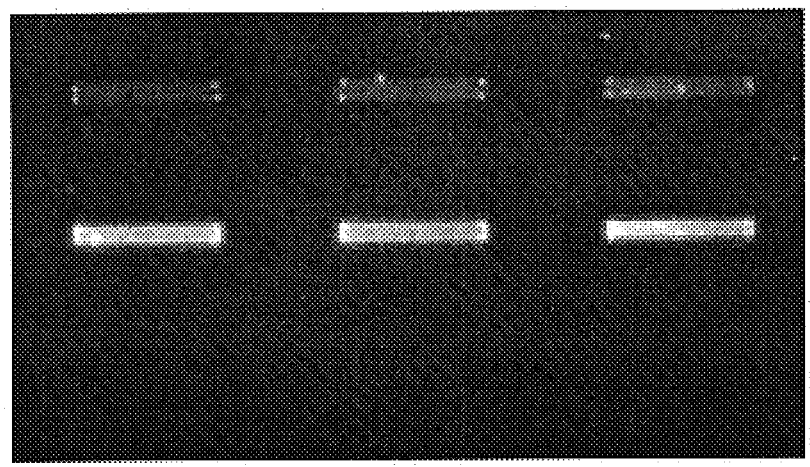
FIG. 4 is a picture of a Western slot blot showing hTM expression in 293FLP cells (passage number 2 (P2) during viral amplification). Row 1, lane 1-3: TM detection using 5 ul cell lysate of P2. Row 2, lane 1-3: TM detection using 30 ul cell lysate of P2. Row 3, lane 1-3: negative control cells.

The P2 lysate was generated as described in Example 3. After CPE was observed, 293FLP cells were detached from the bottom of the culture flask by repeated tapping of the flask. 1 ml of the total of 10 ml of cell suspension was used for the detection of TM expression. The cells in the 1 ml cell suspension were collected by centrifugation for 10 min at 300×g and lysed in 250 μl RIPA buffer. 7 ul of 5× loading buffer was added to 35 μl of the lysed cells and the resulting solution was immersed in boiling water for 3 minutes. 5 and 30 ul of boiled cell lysate were diluted with 250 ul TBS (137 mM sodium chloride, 10 mM Tris, pH is 7.4 at +25° C.) and transferred to a nitrocellulose membrane using a slotblot device (Bio-Dot SF, Biorad). Primary antibody (goat anti-hTM (c-17) 1:2000 dilution, Santa Cruz) and secondary antibody (polyclonal rabbit anti-goat immunoglobulins/HRP, 1:4000 dilution, DakoCytomation)) were used to detect the proteins. As shown in FIG. 4, hTM was detectable in the P2 lysate.

The 5× loading buffer was prepared by mixing 20.0 ml 30% SDS, 11.5 ml 2M sucrose, 6.5 ml 2M Tris-HCL pH 6.8, 2.0 ml beta-mercaptoethanol and bromophenolblue. The RIPA buffer was prepared as described in Example 4(A). A cocktail of protease inhibitors containing 11, 5 μl PMSF (from 34, 8 mg/ml in isopropanol, 64 μl Benzamidine (from 15, 6 mg/ml stock), 100 μl sodium orthovanadate (100 mM), 5 μl pepstadine (from 1 mg/ml stock), 1 μl leupeptine (from 5 mg/ml stock), and 1 μl aprotin (from 5 mg/ml stock) was added to the RIPA buffer immediately before use.

(C) Expression of TM in Virus Infected Vena Cava

Vena cava was excised from rats and cut into six segments of approximately 3 mm long. The segments were incubated for 30 minutes in medium containing gutless luc or TM virus. After incubation, the segments were washed three times and transferred to a 24-well plate containing DMEM. The segments were incubated overnight in an atmosphere of 95% $O_2$ and 5% $CO_2$ with gentle shaking. After 24 hours of incubation the segments were frozen. The frozen sections were thawed in lysis buffer and loaded onto a 7.5% SDS acrylamide gel. After blotting, the blot was probed with an antibody against human TM.

Figure 5:
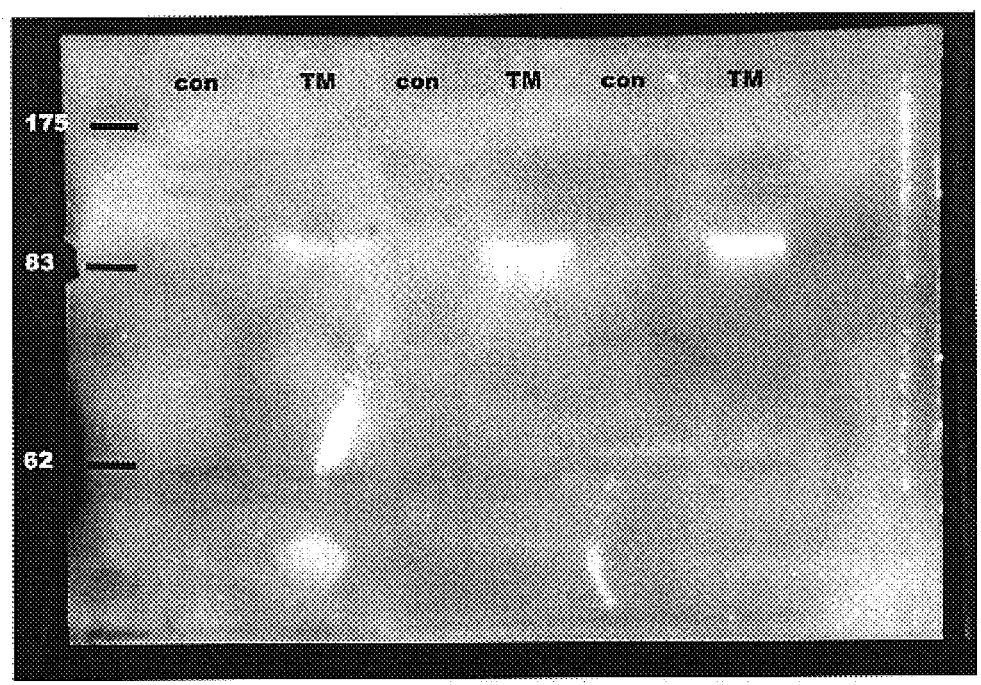
FIG. 5 is a picture of a Western blot showing hTM expression in rat vena cava infected with gutless TM virus.

The Western blot clearly shows that within 24 hours TM expression can be detected (FIG. 5).

As a control, the same HUVEC cells will be infected the gutless adenovirus expressing LacZ. These cells will subsequently be stained with X-gal to look for blue cells. This will demonstrate the viability of the gutless adenovirus backbone itself.

(D) TM Expression in HEK 293 Cells Infected with TM Gutless Virus Passage 1-6

The TM-vector backbone was released by digestion with PacI. 293CRE cells were cultured in a 60 mm dish at 80% confluency. Cells were transfected with 5 μg of PacI digested TM-vector backbone. After 24 hours, 2% DMEM-F12 containing helper virus with a MOI of 10 was added. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=0.

4 ml of P=0 supernatant was added to 2 T75 dish containing 293CRE cells at 80% confluence. Cells were subsequently infected with helpervirus at MOI of 1. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=1. This procedure was repeated until P=6.

Figure 6:
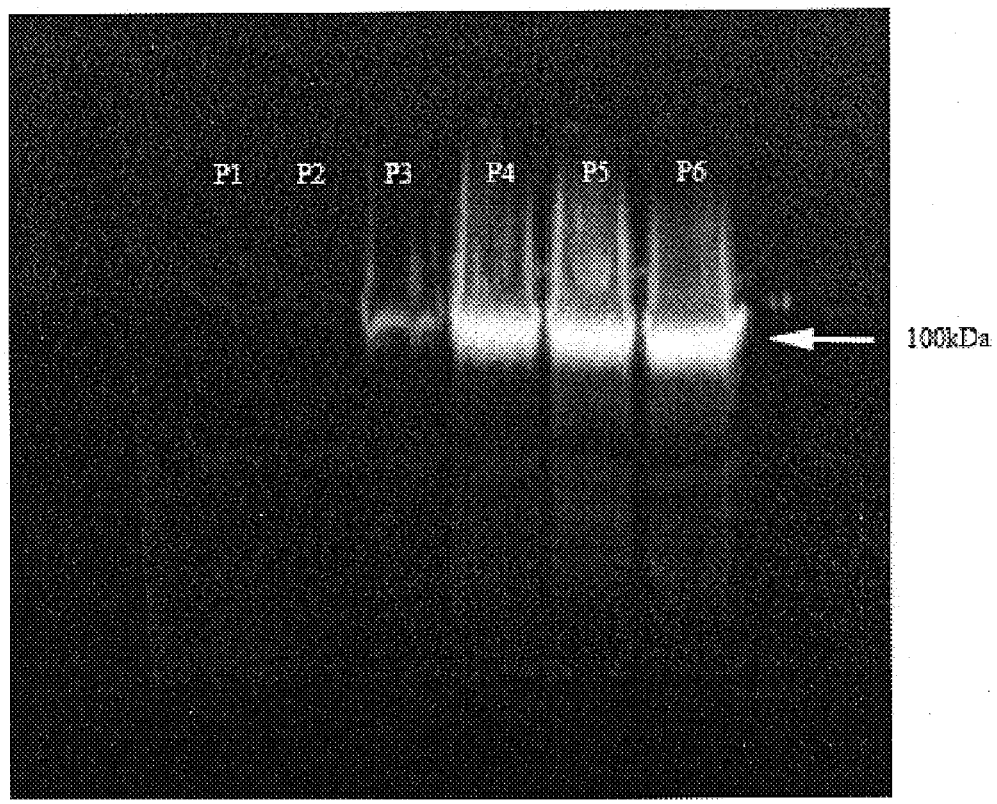
FIG. 6 is a picture of a Western bolt showing TM expression in CRE cells at passage number 1-6 (P1-P6).

HEK 293 cells were cultured in a 6 well cluster and transfected with 200 μl of TM gutless virus of passage 1-6. After 24 hours, the cells were washed with PBS and lysed in 125 μl RIPA buffer. Protein samples (16 μl) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins. As shown in FIG. 6, TM expression is higher in cells infected with virus of higher passage numbers, indicating successful amplification of TM gutless virus in 293CRE cells.

The RIPA buffer (10 ml) was prepared as follows: 100 μl Igepal ca-630, 50 mg sodium deoxycholate, 500 μl 20% SDS, 10 mM β-mercapto ethanol, 1 ml 10×PBS, add water to make up 10 ml. Immediately before use, the following protease inhibitors were added to the RIPA buffer: 115 μl PMSF (from 34.8 mg/ml in isopropanol), 64 μl Benzamidine (from 15.6 mg/ml stock), 100 μl sodium orthovanadate (100 mM), 5 μl pepstatin (from 1 mg/ml stock), 1 μl leupeptin (from 5 mg/ml stock), 1 μl aprotin (from 5 mg/ml stock).

EXAMPLE 5

Composition of the Complete Viral Delivery System (CVDS)

The Complete Viral Delivery System composes of 1:1 mixture of Ham's F12 medium and DMEM, an effective amount of a gutless virus vector carrying a polynucleotide encoding a thrombomodulin protein or a variant of a thrombomodulin protein, and an a cellular oxygen carrier. Preferred oxygen carrier includes: unmodified or chemically modified hemoglobin in the range of 3 g/dl to 10 g/dl and perfluorochemical emulsions. The CVDS may optionally contain 1 mM L-glutamine (Sigma), 1.5 g/L sodium bicarbonate (Sigma), 1× antibiotic-antimycotic (GIBCO® 15240). The CVDM maintains tissue viability during the viral treatment of blood vessel.

EXAMPLE 6

Ex Vivo Treatment of Cardiovascular Disease

A vein segment is harvested from the leg and is stored in Ham's F12 medium. Gutless adenovirus suspended in CVDM is then injected into the isolated vein segment and incubated for 10 to 40 minutes depending on the desired level of transfection. The infection may be performed under pressure to enhance efficiency.

After the incubation, the vein segment is washed several times to eliminate all viral particles that have not entered the endothelial cells of the vein segment, and is then grafted into the desired treatment site. The thorough rinse avoids the spread of the viral vector to other organs of the body following in situ grafting, and any systemic immune response to the viral vector.

EXAMPLE 7

In Vivo Treatment for Peripheral Vascular Disease

In this application, the vein in the leg is treated following evacuation of the clot. A catheter is inserted in the leg vein and both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

EXAMPLE 8

In Vivo Treatment for Renal Disease

In this application, the vein in the kidney is treated following evacuation of the clot. A catheter is inserted in the kidney vein and both the proximal and distal balloons are inflated to isolate the vein segment to be transfected. The segment is evacuated of all blood, rinsed with physiologic saline; it is then filled with the CVDS described above, under pressure. The isolated vein segment is exposed to the CVDS for a period of 10 to 45 minutes, depending upon the desired transfection efficiency.

EXAMPLE 9

In Vivo Treatment with Virus Containing Stent

In this application, a virus-coated stent is placed at a treatment site after angioplasty. The virus is a gutless adenovirus carrying a polynucleotide encoding a thrombomodulin protein or a variant of a thrombomodulin protein. Alternatively, the virus may be embedded in the stent and is releases gradually through a time-releasing mechanism well-known to one skilled in the art.

EXAMPLE 10

In Vivo Expression of TM by Intravenous Infusion of Viral Vectors

Figure 7:
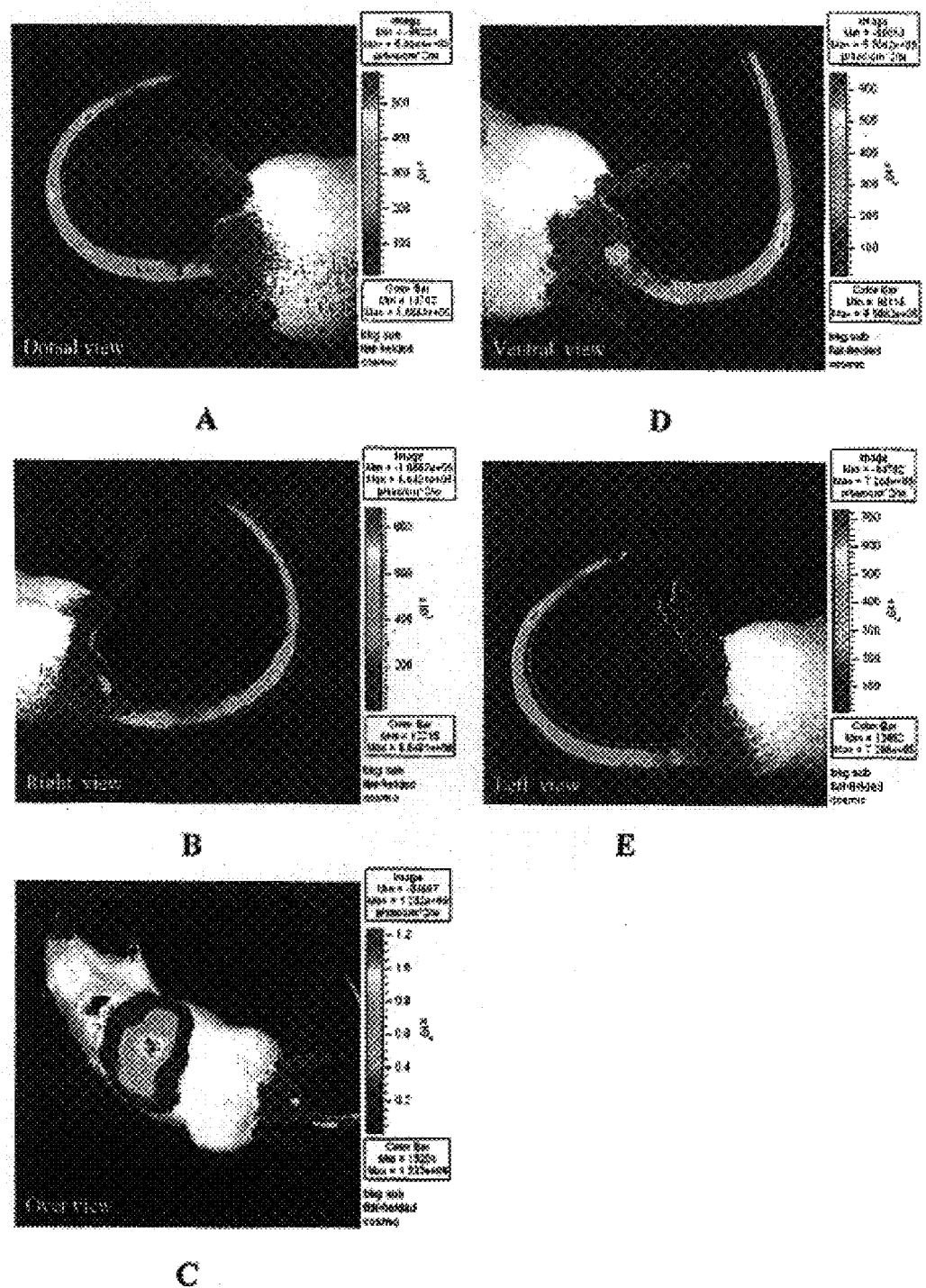
FIG. 7 is a composite of images showing gutless adenovirus-mediated luciferase expression in rat tail vein.

In one experiment, the tail vein of experimental rats was flushed with a solution containing a gutless adenoviral vector carrying a luciferase transgene. As shown in FIG. 7, the expression of luciferase was still very strong in the tail vein eight days after viral infection.

In another experiment, experimental rats were injected intravenously with the gutless TM viruses at doses ranging from $1 \times 10^8$ to $3 \times 10^{11}$ particles/rat. TM expression in liver will be analyzed by the rate of blood coagulation (APTT) and by Western blot of liver biopsy samples.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for inhibiting restenosis or intimal hyperplasia in a mammal, said method comprising the steps of:
    evacuating a clot from a blood vessel in said mammal;
    isolating a segment of the blood vessel around the evacuation site; and
    infecting the segment of blood vessel in vivo using a gutless adenoviral vector comprising a polynucleotide encoding a functional thrombomodulin protein or its variant;
    wherein the functional thrombomodulin protein or its variant is under the control of a regulatory element and is expressed in an amount sufficient to reduce re-occlusion or intimal hyperplasia in the infected blood vessel, and wherein said gutless adenoviral vector comprises the nucleotide sequence of SEQ ID NO:13 or SEQ ID NO:15.

2. The method of claim 1, wherein said gutless adenoviral vector comprises the nucleotide sequence of SEQ ID NO: 13 and SEQ ID NO: 15.

3. The method of claim 1, wherein said gutless adenoviral vector is produced by transfecting 293FLP cells with a linearized plasmid having the nucleotide sequence of SEQ ID NO: 16 followed with infection of a helper virus.

4. The method of claim 1, wherein said thrombomodulin protein has the amino acid sequence of SEQ ID NO: 2.

5. The method of claim 1, wherein said regulatory element is a CMV promoter or a RSV promoter.

6. The method of claim 1, wherein the isolating step further comprises the steps of: inserting a balloon catheter to the site of evacuation; and inflating a proximal balloon and a distal balloons to isolate the vessel segment around the site of evacuation.

7. The method of claim 1, wherein said infecting step further comprises the steps of:
    filling the isolated vessel segment with a complete viral delivery system comprising of 1:1 mixture of Ham's F12 medium and DMEM, an effective amount of the gutless adenovirus vector, and an acellular oxygen carrier; and
    incubating the isolated vessel segment with the complete viral delivery system for a desired period of time.

8. The method of claim 7, wherein said desired period of time is between 15 to 45 minutes.

9. The method of claim 7, wherein said acellular oxygen carrier is selected from the group consisting of unmodified hemoglobin, chemically modified hemoglobin and perfluorochemical emulsions.

10. The method of claim 9, wherein said unmodified hemoglobin or chemically modified hemoglobin is used in the range of 3 g/dl to 10 g/dl.

11. The method of claim 7, wherein the complete viral delivery system further comprises at least one of L-glutamine, sodium bicarbonate, or antibiotic-antimycotic.

12. A method for treating a vascular disease that can benefit from elevated expression of thrombomodulin in a mammal comprising:
    administering a therapeutically effective amount of a gutless adenovirus vector into a segment of a blood vessel around the disease site by placing a stent at said disease site and releasing said gutless adenovirus vectors from said stent,
    wherein said gutless adenovirus vector comprises the nucleotide sequence of SEQ ID NO: 13 or SEQ ID NO: 15, and is capable of expressing a thrombomodulin protein or a variant of the thrombomodulin protein.

13. The method of claim 12, wherein said thrombomodulin protein has an amino acid sequence of SEQ ID NO: 2.

14. A method for treating a thrombovascular disease in a mammal, said method comprising the steps of:
    evacuating a clot from a blood vessel in said mammal;
    isolating a segment of the blood vessel around the evacuation site; and
    administering into the isolated segment an effective amount of a gutless adenoviral vector comprising a polynucleotide encoding a functional thrombomodulin protein,
    wherein said gutless adenoviral vector comprises a regulatory element and the nucleotide sequence of SEQ ID NO: 13 or SEQ ID NO: 15.

15. The method of claim 14, wherein said gutless adenoviral vector is administered into the segment of a blood vessel in said mammal using the stent.

16. The method of claim 14, wherein said gutless adenoviral vector comprises the nucleotide sequence of SEQ ID NO: 13 and SEQ ID NO: 15.

17. The method of claim 14, wherein said gutless adenoviral vector is produced by transfecting 293FLP cells with a linearized plasmid having the nucleotide sequence of SEQ ID NO: 16 followed with infection of a helper virus.

18. The method of claim 14, wherein said thrombomodulin protein has the amino acid sequence of SEQ ID NO: 2.

19. The method of claim 14, wherein said regulatory element is a CMV promoter or a RSV promoter.

20. The method of claim 14, wherein the isolating step further comprises the steps of:
    inserting a balloon catheter into the site of evacuation; and
    inflating a proximal balloon and a distal balloon to isolate the vessel segment around the site of evacuation.

* * * * *

SEQUENCE LISTING

<160> NUMBER OF SEQ ID NOS: 16

<210> SEQ ID NO 1
<211> LENGTH: 13602
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 1

```
catcatcaat aatataccct attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactggtacc gcggccgcct     360
cgagtctaga actagtggat cccccgggct gcaggaattc tgatggctct caaaattcct     420
gcctccttta gggataaaag actttaagac ttttaacaa aaagaaaaa gaaaaaaaa       480
attcctgcct cctggtgtac acacacagaa gggttccctc cccttgaatg tgaccaggat     540
ctgtgaaaat aacgggatag ccgctcctgt gattaggtta tgtggtagac tagagcaaga     600
ttctcctgct ggttttgaag aagtcagctg ccatgttgtg agactgtcat gggctagggc     660
atgagccttt aaatatctgg gagcaacccc tggccagcag ccagtgagaa acgggccct     720
cagtcctaca atcacaagga actaaattct gccaacaacc tgaaggaact tgaagagga    780
tcatgagtcc cttgattcag cttgatgagc ccctgagcag aggatacagc taacttgtac     840
tagggaagta taaaaaacat gcatgggaat gatatatatc aactttaagg ataattgtca     900
tacttctggg aatgaaggga agaaatgggg ctttagttg tattatgatc tttaatttct     960
caaaaaaaat aagatcagaa gcaaatatgg caaaatgtta atactttgt gggtacgtag    1020
gtattcagca tacccttttt tctgagttca aaatatttta taattaaaat gaaatgcagg    1080
ccaggcacag tggctcatgc ctataatacc agcactttgc gaggccgagg tgggaggatg    1140
gcttgaggcc agaccagcct ggccaacatg gcaaaccccc atctctactt aaaaaaaaaa    1200
aaactatata tatatatatg tgtgtgtgtg tgtatatata tatatgtata tatttata    1260
tatgtgtgta tatatatata tgtatatata tttatatatg tgtgtgtata tatatatata    1320
cacacacaca catatataca tacatacata cacacacaca cacacacaat tagccaggca    1380
tggtggcgca cacctgtagt cccagctact tgggaggctg agacatgaga attgcttgaa    1440
cctgggaggc agagtagtta gtgagctgag atcataccac tgcactccag cctggtgaca    1500
gagtgagact ctgtcttaaa aaaataaaa attaaaatta aatgcaaaag gtccaagtga    1560
attgaagagg aaaggggtat caaggaaggt tttgtggagg tgacgtttga gctgggtctt    1620
aaatgactta acatgggat aagaaggag ggaataagga catttcaggt acgagaaata    1680
aggagcaaac agtggaaaca acctaacgtc tgtcaaccag tgaatggata acaaaaatgt    1740
aattcagatg gtatccaact tacgatggtt caacatgaga ttttctgac tttaggatag    1800
atttatcaaa gtagtaaatc catttcaac ttatgatatt ttcaacttca gatgggttta    1860
tcaggacaca gttgaggaac acctgtctat ccatacaatt tggcaataaa aaggaaatga    1920
```

```
gtgcagatat actccacaac atgaatgaac cttgaaaaca ttaagtgaga gaagccagat    1980
acaaaaggcc acatattgta tgattctatt tatacaaaat gtccagaata ggcaaatctt    2040
atagacagca agtaggtaga tgatcagttt gctaggtgct gggggaaggg gaaatgggga    2100
gtgatggcta aggggattgg gtttctttgt ggggcaatga aaatgttta aaattgagcg     2160 tgataatgat tgcacaatgc tgcatatata tataatctat agattatata tatataaaga    2220
gaggctgtta gacagtgata agtgatatat atatatatat acatagagag agagagagag    2280
agagagagag gctgttagtg ataagtgatc aggaaaataa agtattgag gaggaatacg     2340 aagttgacgg tgtgaaaaca tgagatttta tataggatgg ccagggaagg ccttaatgag    2400
aaagtgactt atgagtaaaa acaagggatc ctaaacctta gcatgcatca gaatcactcg    2460
gaaacttgtt aaagcatagc ttgctgggcc tcatcacaga tattttgatt cggtaggttc    2520
ttgtctgata ttaatacttt tggtctaggg aaccacattt tgagaaccac tgagctaaag    2580
gaagtaaagg tttcccttag tttactagct ggtaaaccta ggaaactgct tagcctctcg    2640
gtgctaagat acaaaatact ttagcacata ataacacatg gaaaatagtc tataaattat    2700
aaatattatt ttttatgtac caaatattac ataagacaaa atctaagcaa gatatatata    2760
tatatacata aaatataaga tatatatgta tatattatat atagataaat agagagagag    2820
agttatgttt agaaagaaaa tacttcaaac taaaaaaaga gaggtaggaa gtataccatt    2880
ccattattgg taaaaacaaa ttactaagta gtctttacaa aaaaccaatc tcactccttt    2940
agaacacaag cccaccatta aaactgatgc agaggaattc tctcccctgg cttaccttta    3000
ggatggtgca tactaagtta gaaaagtcat aaatgttata ttaaaagtaa atgtgaactt    3060
acttccacaa tcaagacatt ctagaagaaa aagagaaatg aaaatcagta caatgaataa    3120
aacggtattt ccaattataa gtcaaatcac atcataacaa ccctaaggaa ttatccaaac    3180
tcttgttttt agatgcttta ttatatcaaa ctctccttta aacaagtggc ccatctgctg    3240
ggatttggaa gcctgtaata ctgaaatttt catcataatg gaaattttaa aaacagaatt    3300
tgacccacct gttttttaaaa cactttcatt acttaacaag aggtctaatc ttgggcaagt    3360
cttgaaattt ctctggcctt agtttcccat gtgttaaatg aaacttgaag cagttggtct    3420
cttatagtct cctgactcta acattctaag aattatattt gtacaataac tcaaaaatca    3480
cataatttaa tttaccatat ggactccaaa atatattttc tcattaggct aaacttgatc    3540 tgcatttct ggatgtgtcc atattcttgg actacactaa aacatgatac caatgcttcc     3600
tctcaccata aaccctcact tcgctttcta catttaagaa ttttatagct ggaagagtcc    3660
ttaacagaaa ataccatcta ataattaccc ctcaaaatcg agaaagtcct atctgttctt    3720
atgctagtta taagaatgag gcagcatttc acataatggt tataaacact gccacaagaa    3780
gattcatgat gtgttgttta tctgtagctc tcatcatact ctgtcatata actatagcat    3840
taagatttta atgttctata tattcttcta agacagtgtt taccagagta aggcacaaaa    3900
gatccactgg tttgcaagaa agattagaac ttttaaattt tttacctcac cttgtttaat    3960
ctatattttt gtatgtattt tgtaacatat atattttat taccataaat catatataat     4020
ttaaaatgca tatattaggg gtaaatgctc aggaaacttt ttataaattg ggcatgcaaa    4080
tacaagtttg aagactcact gttctaggta ttaaaagtaa agttataacc aagtaaagct    4140 tccaccttt catgtctcaa agcagtttat tgttggaggt aagatctctt agaagcctaa     4200
acaggtccaa gtacagaatg aagtaaggct agcccataac ttgtggcaag caattcatac    4260
tatttctctc atgctgagct ctcctcagtg aagcagctac tatagacaac tgcagcctat    4320
```

```
tggtagccta ttttacaggc aggaaaaaaa ttactttta ttcaaagtgg aactcaggac    4380
atggggagaa aatgaataca aaaataggg tcaatccaaa ggcacacagc aaatgagtaa    4440
cacagttatg ttttttttccc atttgtatga ggtcccagta aattctaagt aaactgcaaa   4500
tttaataata cactaaaaaa gccatgcaat tgttcaaatg aatcccagca tggtacaagg   4560
agtacagaca ctagagtcta aaaacaaaa gaatgccatt attgagtttt tgaattatat    4620
caagtagtta catctctact taataaatga gaaaacgag gataagaggc catttgataa    4680
aatgaaaata gccaagaagt ggtattagag acttgaatac aggtattcgg gtccaaagtt   4740
catctgctca aatactaact ggggaaaaga gggaaaaata tttatataca tatatatctg   4800
cacacaaaaa tacccccaaa agacaaaatg aggccaggca gggtggctca cacccgtaat   4860
cccggtactt tgggaggctg aggcaggtgg atacctgaga tcaggagttg agatcagcc    4920 tggtcaacat ggtgaaaccc tgtctctact aaagataaaa aaattagcca ggcatggtgg   4980
cgtgcgcctg taatcccagc tacttgggag tctgaggcag gagaatcact tgaactggga   5040
aggggaggtt gcagtgagcc aagatcgtac tactgcactc cagcctgggc agcagagtga   5100
gactccatca caaaaataaa taaataaata aaatacaatg aaacagaaag ttcaaataat   5160
cccataatct taccaccaag aaataacttt cactcgttat acttattgat ttttccataa   5220
taaatgtact ttactgtgac tatcatgaaa agaaagttat tttagaaaca gagaactgtt   5280
tcagatcaaa tctatgtagt agaacagagc cattaggtgg gaaagacgag atcaaactaa   5340
atctcagaag gcctaaaagg ctaggtccat tccagcacta aaaactgacc agacaagtaa   5400
tggcttcaac agcttctaaa tatggacaaa gcatgctgaa agggaaggac aggtctaaca   5460
gtggtatatg aaatgaacag gaggggcaaa gctcatttct cctctgaagt tttccaaaga   5520
tgctgaggag gacattagtt tgacatgacc ctgatatggg acaagataat ttcacagaag   5580
ttttacatgt taaagttttc ttatagatac tcattcaagt aagcaatgaa cactaaaatc   5640
taaagaaaga aaagagcttt agagtcaggt ctgtattcaa attcaagctc taccacttac   5700
tggttctgtg actttgggca agtcttttaa ccttattaag tcttaatttc ctgatttgta   5760 aaatgggat atcgtctccc tcacaggatt gttgtgaaac tttatgaga ttaatgcctt     5820 tatatttggc atagtgtaag taaacaataa ctggcagctt caaaaaaaaa aagcagtagc   5880
attccatcat ttattattgg ttactctcaa aaagtttttc aatgtactag aagataaata   5940
ttcaaatacc ttaatatctc cattattttc aggtaaacag catgctcctg aacaaccaat   6000
gggtcaacaa ataattaaa agggaaatct aaaaacatct tgatattaaa ctacatggaa    6060
gcacaatata ccaaaaccaa tggttcacac taggagaatt ttaaggtaca agaaaactct   6120
ttgagatttc ttaaaataat agtatgtctg aatttattga gtgatttacc agaaactgtt   6180
gtaagagctc tacttgcatt atagcactta atcctcttaa ctctatggct gctattatca   6240 acctcacccct aatcacatat gggacacaga gaggttaagt aacttgccca aggtcagagt   6300
taggaagtac taagccatgc tttgaatcag ttgtcaggct ccggaactca cactttcagc   6360
cactacataa tactgctttg ctatctttta ggaaactatg tgagtctacc tcacatagac   6420
tcacataggt ttgttttttt tttttttta aaggctatct tttccccat caatgttttt     6480 tgaaggatcc caaattagag tcccacagag gcagacagca gtacttgaca atatggacat   6540
ttaaggttaa tgttggattc tactgtcttt ttactacatg acctagggaa cgataattaa   6600
cctagactgc ttccaagggt taaataaccc atttagttat actatgtaaa ttatctctta   6660
gtgattgatt gaaagcacac tgttactaat tgactcggta tgaagtgctt ttttttcttc   6720
```

```
cctttcaaga tacatacctt tccagttaaa gttgagagat catctccacc aattactttt    6780
atgtcccctg ttgactggtc attctagtta aaaaaaaaaa aaactatata tatatatatc    6840
tacacacaca tatgtatatg tatatcctta tgtacacaca caaacttcaa attaaatgag    6900
aactagaaga tttgagaagt tagctagcta atatccatag cattatgata ttctaaatga    6960
tatgaattat aagaattagg tttcctgaaa tgaatgacta gaaaactttc aagtagagat    7020
tagtaaaaat taaaaagtcc taatcggcca ttactgattt tgatgttttta agagtcctaa    7080
aaaatgggtt acatccattt ttaagtgggt agtattataa cagccaccca tcttcaatca    7140
cagtgatttc tgaattgtga gggaagttat tagcatgaca ggtgtctggt tctggccctg    7200
tacgattccc atgagtcaag caaattgtaa gggctggtct atatcacacc caaccccaag    7260
gatatgtccc tcaaaagtct agcccaggcc ccgtcatctt cagcatcatc tgggaaacca    7320
ggtctgatta gtagtccttt aaggaatacc tcttaggctc ccattttact gctatcacag    7380
aatccaataa aacccttaca ggagattcaa tgggaaatgc tcaacaccca ctgtagttgg    7440
tggtgacaat gaccataatt tggctgtgct ggattcagga cagaaaattt gggtgaaaga    7500
gcaggtgaac aaaagagctt cgacttgccc tagcagagag caagccatac cataccacaa    7560
agccacagca attacaacgg tgcagtacca gcacagtaaa tgaacaaagt agagcccaga    7620
aacagaccca gaactatatg aggatttagt atacaataaa gatggtattt cgagtcagta    7680
gggaaaagat gaattattca ataaatgatg tttggccaac tagtaaccca tttgggaaaa    7740
aataaaagta tggtccctac ctcacagcat acacaaaaat aaattccaga cggattaaaa    7800
tctaaatgta aaaaataaag ccataagtgg actggaagaa aatagagaat ttttttttaac    7860
atccgtagaa agggtaaaaa cccaggcatg acatgaacca aaactgaaga ggttctgtaa    7920
caaataccccc cttttatata ttgggctcca acaataagaa cccataggaa aatggagaat    7980
gaacacaaat agacaattta tagaagagaa ggttataagg tgtaaaatta tatctatctg    8040
agaaacaaac actaaaacaa tgtgattcta ctgttctccc acccatactg gcaaaactta    8100
agcctgataa tatgctgagg ggaaataagc actcttgttg gtgagagtat taattggcat    8160
agcttctttt gaaaatgaca tagcaatacc tgttaaaatt gcaaacatgc atgtcactta    8220
atccagtaat cccacttctg ggaatcaatg ctacaaaaac actgacaagt atacaaagat    8280
acattcaaga gtgttcactg ggccgggtgc ggtggcttca tgcctgtaat cccagggagg    8340
cagaggcaag acgatcgctt gaccccagga gttcaaggcc agcccgagaa acacagcaag    8400
accctgtctc tcttttttttt atttaaaaaa taaatgttca ctgtatcagt tgttcacaaa    8460
aacaaaccaa catgtccatt aacagggaac catttaaatt aatcaagttc atctacacaa    8520
tgtaatacca tgcaactatt aaaaagcacc tgataatcca aagcacactg agacagaata    8580
atgctattaa aaacaccaag tagtggaaca ctgtgttgcc tatgacacca tttttattca    8640
acatttaaac aaatttgtaa cagcaattac atgagtagtg acaatggcgt ttatgagact    8700
tttcacttttt atgtgcttct atttttgtta tgcttctata tatacatcca tttattatgg    8760
agtgttactt tcaaaaatca caaatgggcc agtattattt ggtgttgcaa ggtgagcata    8820
tgacttctga tatcaaccct tgcatattac ttctcaattt agggaaatta cagacatccc    8880
ttattctaac taacttaaaa cccagcattt caaacataca gaattgatgg ggaaaaaaaa    8940
gaaagaagaa agaaagaaaa ggcaacaagc ttcagatgac agtgactcac atcaaattat    9000
ttataaaatc tgttaaatag tgccatcttc tggagatacc tggtattaca gtccaactcc    9060
agttgatgtc tttacagaga caagaggaat aaaggaaaaa atattcaaga actgaaaagt    9120
```

```
atggagtcat ggaaaaattg ctgtgatcca aaggctacgg tgataggaca agaaacaaga    9180
gaactccaag cagtaagaca ctgctgttct attagcatcc aaacctccat actcctgttt    9240
gccccaaggc ttttttaaaa aatagagaca ggatctcact attttgctca ggctggtctt    9300
gaactcctgg actcaagcta tcctcctgcc tcggcctcct aaagtgccga gattacaggc    9360
ttgagtcacc atacctggct atttatttt tcttaactct cttgcctggc ctatagccac     9420
catggaagct aataaagaat attaatttaa gagtaatggt atagttcact acattggaat    9480
acaggtataa gtgcctacat tgtacatgaa tggcatacat ggatcaatta ccccacctgg    9540
gtggccaaag gaactgcgcg aacctccctc cttggctgtc tggaacaagc ttcccactag    9600
atccctttac tgagtgcctc cctcatcttt aattatggtt aagtctagga taacaggact    9660
ggcaaaggtg aggggaaagc ttcctccaga gttgctctac cctctcctct accgtcctat    9720
ctcctcactc ctctcagcca aggagtccaa tctgtcctga actcagagcg tcactgtcaa    9780
ctacataaaa ttgccagaga agctctttgg gactacaaac atacccctt aatgtcttta     9840 tttctatttt gtctacctct tcagtctagg tgaaaaaata ggaaggataa tagggaagaa    9900
ctttgtttat gcctacttat ccgccccctag gaattttgaa aacctctagg tagcaataag   9960
aactgcagca tggtatagaa aaagaggagg aaagctgtat agaaatgcat aataaatggg    10020
caggaaaaga actgcttgga acaaacaggg aggttgaact ataaggagag aaagcagaga    10080
ggctaatcaa caaggctggg ttcccaagag ggcatgatga gactattact aaggtaggaa    10140
ttactaaggg ctccatgtcc ccttagtggc ttagtactat gtagcttgct ttctgcagtg    10200
aacttcagac ccttctttta ggatcctaga atggactttt tttttttatc ggaaaacagt    10260
cattctctca acattcaagc aggccccaag tctaccacac tcaatcacat tttctcttca    10320
tatcataatc tctcaaccat tctctgtcct tttaactgtt tttctatacc ctgatcaaat    10380
gccaacaaaa gtgagaatgt tagaatcatg tatttttaga ggtagactgt atctcagata    10440
aaaaaaaagg gcagatattc cattttccaa aatatgtatg cagaaaaaat aagtatgaaa    10500
ggacatatgc tcaggtaaca agttaatttg tttacttgta ttttatgaat tcctaaaac     10560 ctacgtcacc cgccccgttc ccacgccccg cgccacgtca caactccac ccctcatta     10620 tcatattggc ttcaatccaa aataaggtat attattgatg atgttaatta acatgcatgg    10680
atccatatgc ggtgtgaaat accgcacaga tgcgtaagga gaaataccg catcaggcgc     10740 tcttccgctt cctcgctcac tgactcgctg cgctcggtcg ttcggctgcg gcgagcggta    10800
tcagctcact caaaggcggt aatacggtta tccacagaat caggggataa cgcaggaaag    10860
aacatgtgag caaaaggcca gcaaaaggcc aggaaccgta aaaaggccgc gttgctggcg    10920
tttttccata ggctccgccc ccctgacgag catcacaaaa atcgacgctc aagtcagagg    10980
tggcgaaacc cgacaggact ataaagatac caggcgtttc cccctggaag ctccctcgtg    11040
cgctctcctg ttccgaccct gccgcttacc ggatacctgt ccgcctttct cccttcggga    11100
agcgtggcgc tttctcatag ctcacgctgt aggtatctca gttcggtgta ggtcgttcgc    11160
tccaagctgg gctgtgtgca cgaacccccc gttcagcccg accgctgcgc cttatccggt    11220
aactatcgtc ttgagtccaa cccggtaaga cacgacttat cgccactggc agcagccact    11280
ggtaacagga ttagcagagc gaggtatgta ggcggtgcta cagagttctt gaagtggtgg    11340
cctaactacg gctacactag aaggacagta tttggtatct gcgctctgct gaagccagtt    11400
accttcggaa aaagagttgg tagctcttga tccggcaaac aaaccaccgc tggtagcggt    11460
ggtttttttg tttgcaagca gcagattacg cgcagaaaaa aaggatctca agaagatcct    11520
```

```
ttgatcttttt ctacggggtc tgacgctcag tggaacgaaa actcacgtta agggattttg    11580
gtcatgagat tatcaaaaag gatcttcacc tagatccttt taaattaaaa atgaagtttt    11640
aaatcaatct aaagtatata tgagtaaact tggtctgaca gttaccaatg cttaatcagt    11700
gaggcaccta tctcagcgat ctgtctattt cgttcatcca tagttgcctg actcccgtc    11760 gtgtagataa ctacgatacg ggagggctta ccatctggcc ccagtgctgc aatgataccg    11820
cgagacccac gctcaccggc tccagattta tcagcaataa accagccagc cggaagggcc    11880
gagcgcagaa gtggtcctgc aactttatcc gcctccatcc agtctattaa ttgttgccgg    11940
gaagctagag taagtagttc gccagttaat agtttgcgca acgttgttgc cattgctgca    12000
gccatgagat tatcaaaaag gatcttcacc tagatccttt tcacgtagaa agccagtccg    12060
cagaaacggt gctgaccccg gatgaatgtc agctactggg ctatctggac aagggaaaac    12120
gcaagcgcaa agagaaagca ggtagcttgc agtgggctta catggcgata gctagactgg    12180
gcggttttat ggacagcaag cgaaccggaa ttgccagctg gggcgccctc tggtaaggtt    12240
gggaagccct gcaaagtaaa ctggatggct ttcttgccgc caaggatctg atggcgcagg    12300
ggatcaagct ctgatcaaga gacaggatga ggatcgtttc gcatgattga acaagatgga    12360
ttgcacgcag gttctccggc cgcttgggtg gagaggctat tcggctatga ctgggcacaa    12420
cagacaatcg gctgctctga tgccgccgtg ttccggctgt cagcgcaggg gcgcccggtt    12480
ctttttgtca agaccgacct gtccggtgcc ctgaatgaac tgcaagacga ggcagcgcgg    12540
ctatcgtggc tggccacgac gggcgttcct tgcgcagctg tgctcgacgt tgtcactgaa    12600
gcgggaaggg actggctgct attgggcgaa gtgccggggc aggatctcct gtcatctcac    12660
cttgctcctg ccgagaaagt atccatcatg gctgatgcaa tgcggcggct gcatacgctt    12720
gatccggcta cctgcccatt cgaccaccaa gcgaaacatc gcatcgagcg agcacgtact    12780
cggatggaag ccggtcttgt cgatcaggat gatctggacg aagagcatca ggggctcgcg    12840
ccagccgaac tgttcgccag gctcaaggcg agcatgcccg acggcgagga tctcgtcgtg    12900
acccatggcg atgcctgctt gccgaatatc atggtggaaa atggccgctt ttctggattc    12960
atcgactgtg gccggctggg tgtggcggac cgctatcagg acatagcgtt ggctacccgt    13020
gatattgctg aagagcttgg cggcgaatgg gctgaccgct tcctcgtgct ttacggtatc    13080
gccgctcccg attcgcagcg catcgccttc tatcgccttc ttgacgagtt cttctgaatt    13140
ttgttaaaat ttttgttaaa tcagctcatt ttttaaccaa taggccgaaa tcggcaaaat    13200
cccttataaa tcaaaagaat agaccgagat agggttgagt gttgttccag tttggaacaa    13260
gagtccacta ttaaagaacg tggactccaa cgtcaaaggg cgaaaaaccg tctatcaggg    13320
cgatggccca ctacgtgaac catcaccctg atcaagtttt tgggggtcga ggtgccgtaa    13380
agcactaaat cggaacccta aagggagccc ccgatttaga gcttgacggg gaaagccggc    13440
gaacgtggcg agaaaggaag ggaagaaagc gaaaggagcg ggcgctaggg cgctggcaag    13500
tgtagcggtc acgctgcgcg taaccaccac acccgccgcg cttaatgcgc cgctacaggg    13560
cgcgtccatt cgccattcag gatcgaatta attcttaatt aa                      13602
```

<210> SEQ ID NO 2
<211> LENGTH: 575
<212> TYPE: PRT
<213> ORGANISM: Homo sapiens

```
<400> SEQUENCE: 2

Met Leu Gly Val Leu Val Leu Gly Ala Leu Ala Leu Ala Gly Leu Gly
  1               5                  10                  15

Phe Pro Ala Pro Ala Glu Pro Gln Pro Gly Gly Ser Gln Cys Val Glu
             20                  25                  30

His Asp Cys Phe Ala Leu Tyr Pro Gly Pro Ala Thr Phe Leu Asn Ala
         35                  40                  45

Ser Gln Ile Cys Asp Gly Leu Arg Gly His Leu Met Thr Val Arg Ser
     50                  55                  60

Ser Val Ala Ala Asp Val Ile Ser Leu Leu Asn Gly Asp Gly Gly
 65                  70                  75                  80

Val Gly Arg Arg Arg Leu Trp Ile Gly Leu Gln Leu Pro Pro Gly Cys
                 85                  90                  95

Gly Asp Pro Lys Arg Leu Gly Pro Leu Arg Gly Phe Gln Trp Val Thr
             100                 105                 110

Gly Asp Asn Asn Thr Ser Tyr Ser Arg Trp Ala Arg Leu Asp Leu Asn
             115                 120                 125

Gly Ala Pro Leu Cys Gly Pro Leu Cys Val Ala Val Ser Ala Ala Glu
130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
             180                 185                 190

Tyr Gly Thr Pro Phe Ala Ala Arg Gly Ala Asp Phe Gln Ala Leu Pro
            195                 200                 205

Val Gly Ser Ser Ala Ala Val Ala Pro Leu Gly Leu Gln Leu Met Cys
            210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
    290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
        355                 360                 365

Cys Phe Arg Ala Asn Cys Glu Tyr Gln Cys Gln Pro Leu Asn Gln Thr
    370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415
```

```
Cys Asp Pro Asn Thr Gln Ala Ser Cys Glu Cys Pro Glu Gly Tyr Ile
                420                 425                 430

Leu Asp Asp Gly Phe Ile Cys Thr Asp Ile Asp Glu Cys Glu Asn Gly
            435                 440                 445

Gly Phe Cys Ser Gly Val Cys His Asn Leu Pro Gly Thr Phe Glu Cys
        450                 455                 460

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
                485                 490                 495

Pro Ser Pro Thr Pro Gly Ser Thr Leu Thr Pro Ala Val Gly Leu
                500                 505                 510

Val His Ser Gly Leu Leu Ile Gly Ile Ser Ile Ala Ser Leu Cys Leu
            515                 520                 525

Val Val Ala Leu Leu Ala Leu Leu Cys His Leu Arg Lys Lys Gln Gly
        530                 535                 540

Ala Ala Arg Ala Lys Met Glu Tyr Lys Cys Ala Ala Pro Ser Lys Glu
545                 550                 555                 560

Val Val Leu Gln His Val Arg Thr Glu Arg Thr Pro Gln Arg Leu
                565                 570                 575

<210> SEQ ID NO 3
<211> LENGTH: 1725
<212> TYPE: DNA
<213> ORGANISM: Homo sapiens

<400> SEQUENCE: 3
atgcttgggg tcctggtcct tggcgcgctg gccctggccg gctgggggtt ccccgcaccc      60
gcagagccgc agccgggtgg cagccagtgc gtcgagcacg actgcttcgc gctctaccccg    120 ggccccgcga ccttcctcaa tgccagtcag atctgcgacg actgcggggc cacctaatg     180 acagtgcgct cctcggtggc tgccgatgtc atttccttgc tactgaacgg cgacggcggc    240
gttggccgcc ggcgcctctg gatcggcctg cagctgccac ccggctgcgg cgaccccaag    300
cgcctcgggc ccctgcgcgg cttccagtgg gttacgggag acaacaacac cagctatagc    360
aggtgggcac ggctcgacct caatggggct cccctctgcg gcccgttgtg cgtcgctgtc    420
tccgctgctg aggccactgt gcccagcgag ccgatctggg aggagcagca gtgcgaagtg    480
aaggccgatg gcttcctctg cgagttccac ttccagccaa cctgcaggcc actggctgtg    540
gagcccggcg ccgcggctgc cgccgtctcg atcacctacg caccccgtt cgcggcccgc     600 ggagcggact ccaggcgct gccggtgggc agctccgccg cggtggctcc cctcggctta    660
cagctaatgt gcaccgcgcc gcccggagcg gtccaggggc actgggccag ggaggcgccg    720
ggcgcttggg actgcagcgt ggagaacggc ggctgcgagc acgcgtgcaa tgcgatccct    780
ggggctcccc gctgccagtg cccagccggc ccgcccctgc aggcagacgg cgctcctgc    840 accgcatccg cgacgcagtc ctgcaacgac ctctgcgagc acttctgcgt tcccaacccc    900
gaccagccgg gctcctactc gtgcatgtgc gagaccggct accggctggc ggccgaccaa    960
caccggtgcg aggacgtgga tgactgcata ctggagccca gtccgtgtcc gcagcgctgt   1020
gtcaacacac agggtggctt cgagtgccac tgctacccta actacgacct ggtggacggc    1080
gagtgtgtgg agcccgtgga cccgtgcttc agagccaact gcgagtacca gtgccagccc    1140
ctgaaccaaa ctagctacct ctgcgtctgc gccgagggct cgcgcccat tcccacgag     1200 ccgcacaggt gccagatgtt ttgcaaccag actgcctgtc cagccgactg cgaccccaac    1260
```

| | |
|---|---|
| acccaggcta gctgtgagtg ccctgaaggc tacatcctgg acgacggttt catctgcacg | 1320 |
| gacatcgacg agtgcgaaaa cggcggcttc tgctccgggg tgtgccacaa cctccccggt | 1380 |
| accttcgagt gcatctgcgg gcccgactcg gcccttgccc gccacattgg caccgactgt | 1440 |
| gactccggca aggtggacgg tggcgacagc ggctctggcg agccccgcc cagcccgacg | 1500 |
| cccggctcca ccttgactcc tccggccgtg gggctcgtgc attcgggctt gctcataggc | 1560 |
| atctccatcg cgagcctgtg cctggtggtg gcgcttttgg cgctcctctg ccacctgcgc | 1620 |
| aagaagcagg gcgccgccag ggccaagatg gagtacaagt gcgcggcccc ttccaaggag | 1680 |
| gtagtgctgc agcacgtgcg gaccgagcgg acgccgcaga gactc | 1725 |

<210> SEQ ID NO 4
<211> LENGTH: 649
<212> TYPE: DNA
<213> ORGANISM: Homo sapiens
<220> FEATURE:
<221> NAME/KEY: modified_base
<222> LOCATION: (335)
<223> OTHER INFORMATION: a, c, g, t, unknown or other

<400> SEQUENCE: 4

| | |
|---|---|
| tctagacgcg ttgacattga ttattgacta gttattaata gtaatcaatt acggggtcat | 60 |
| tagttcatag cccatgatat catatggagt tccgcgttac ataacttacg gtaaatggcc | 120 |
| cgcctggctg accgcccaac gacccccgcc cattgacgtc aataatgacg tatgttccca | 180 |
| tagtaacgcc aatagggact ttccattgac gtcaatgggt ggagtattta cggtaaactg | 240 |
| cccacttggc agtacatcaa gtgtatcata tgccaagtac gccccctat tgacgtcaat | 300 |
| gacggtaaat ggcccgcctg gcattatgcc cagtncatga ccttatggga ctttcctact | 360 |
| tggcagacat ctacgtatta gtcatcgcta ttaccatggt gatgcggttt tggcagtaca | 420 |
| tcaatgggcg tggatagcgg tttgactcac ggggattttc caagtctcca ccccattgac | 480 |
| gtcaatggga gtttgttttg gcaccaaaat caacgggact ttccaaaatg tcgtaacaac | 540 |
| tccgccccat tgacgcaaat gggcggtagg cgtgtacggt gggaggtcta tataagcaga | 600 |
| gctctctggc taactagaga acccctgctt actggcttat cgagatatc | 649 |

<210> SEQ ID NO 5
<211> LENGTH: 3693
<212> TYPE: DNA
<213> ORGANISM: Homo sapiens

<400> SEQUENCE: 5

| | |
|---|---|
| ggcagcgcgc agcggcaaga agtgtctggg ctgggacgga caggagaggc tgtcgccatc | 60 |
| ggcgtcctgt gccctctgc tccggcacgg ccctgtcgca gtgcccgcgc tttccccggc | 120 |
| gcctgcacgc ggcgcgcctg ggtaacatgc ttgggggtcct ggtccttggc gcgctggccc | 180 |
| tggcgcggcct ggggttcccc gcacccgcag agccgcagcc gggtggcagc cagtgcgtcg | 240 |
| agcacgactg cttcgcgctc tacccggggcc ccgcgacctt cctcaatgcc agtcagatct | 300 |
| gcgacggact gcggggccac ctaatgacag tgcgctcctc ggtggctgcc gatgtcattt | 360 |
| ccttgctact gaacggcgac ggcggcgttg gccgcggcg cctctggatc ggcctgcagc | 420 |
| tgccacccgg ctgcgcgac cccaagcgcc tcggccct gcgcggcttc cagtgggtta | 480 |
| cgggagacaa caacaccagc tatagcaggt gggcacggct cgacctcaat ggggctcccc | 540 |
| tctgcggccc gttgtgcgtc gctgtctccg ctgctgaggc cactgtgccc agcgagccga | 600 |
| tctgggagga gcagcagtgc gaagtgaagg ccgatggctt cctctgcgag ttccactcc | 660 |

-continued

```
cagccacctg caggccactg gctgtggagc ccggcgccgc ggctgccgcc gtctcgatca    720
cctacggcac cccgttcgcg gcccgcggag cggacttcca ggcgctgccg gtgggcagct    780
ccgccgcggt ggctcccctc ggcttacagc taatgtgcac cgcgccgccc ggagcggtcc    840
aggggcactg ggccagggag gcgccgggcg cttgggactg cagcgtggag aacggcggct    900
gcgagcacgc gtgcaatgcg atccctgggg ctccccgctg ccagtgccca gccggcgccg    960
ccctgcaggc agacgggcgc tcctgcaccg catccgcgac gcagtcctgc aacgacctct   1020
gcgagcactt ctgcgttccc aaccccgacc agccgggctc ctactcgtgc atgtgcgaga   1080
ccggctaccg gctggcggcc gaccaacacc ggtgcgagga cgtggatgac tgcatactgg   1140
agcccagtcc gtgtccgcag cgctgtgtca acacacaggg tggcttcgag tgccactgct   1200
accctaacta cgacctggtg gacggcgagt gtgtggagcc cgtggacccg tgcttcagag   1260
ccaactgcga gtaccagtgc cagcccctga ccaaactagc taccctctgc gtctgcgccg   1320
agggcttcgc gcccattccc cacgagccgc acaggtgcca gatgttttgc aaccagactg   1380
cctgtccagc cgactgcgac cccaacaccc aggctagctg tgagtgccct gaaggctaca   1440
tcctggacga cggtttcatc tgcacggaca tcgacgagtg cgaaaacggc ggcttctgct   1500
ccggggtgtg ccacaacctc cccggtacct tcgagtgcat ctgcgggccc gactcggccc   1560
ttgcccgcca cattggcacc gactgtgact ccggcaaggt ggacggtggc gacagcggct   1620
ctggcgagcc ccgcccagc ccgacgcccg gctccacctt gactcctccg gccgtggggc   1680
tcgtgcattc gggcttgctc ataggcatct ccatcgcgag cctgtgcctg gtggtggcgc   1740
ttttggcgct cctctgccac ctgcgcaaga agcagggcgc cgccagggcc aagatggagt   1800
acaagtgcgc ggccccttcc aaggaggtag tgctgcagca cgtgcggacc gagcggacgc   1860
cgcagagact ctgagcggcc tccgtccagg agcctggctc cgtccaggag cctgtgcctc   1920
ctcaccccca gctttgctac caaagcacct tagctggcat tacagctgga gaagaccctc   1980
cccgcacccc ccaagctgtt ttcttctatt ccatggctaa ctggcgaggg ggtgattaga   2040
gggaggagaa tgagcctcgg cctcttccgt gacgtcactg gaccactggg caatgatggc   2100
aattttgtaa cgaagacaca gactgcgatt tgtcccaggt cctcactacc gggcgcagga   2160
gggtgagcgt tattggtcgg cagccttctg ggcagacctt gacctcgtgg gctagggatg   2220
actaaaatat ttatttttt taagtattta ggttttgtt tgtttccttt gttcttacct    2280
gtatgtctcc agtatccact ttgcacagct ctccggtctc tctctctcta caaactccca   2340
cttgtcatgt gacaggtaaa ctatcttggt gaattttttt ttcctagccc tctcacattt   2400
atgaagcaag ccccacttat tccccattct tcctagtttt ctcctcccag gaactgggcc   2460
aactcacctg agtcacccta cctgtgcctg accctacttc ttttgctctt agctgtctgc   2520
tcagacagaa cccctacatg aaacagaaac aaaacactaa aaataaaaa tggccatttg   2580 cttttttcacc agatttgcta atttatcctg aaatttcaga ttcccagagc aaaataattt   2640
taaacaaagg ttgagatgta aaaggtatta aattgatgtt gctggactgt catagaaatt   2700
acacccaaag aggtatttat ctttactttt aaacagtgag cctgaatttt gttgctgttt   2760
tgatttgtac tgaaaatgg taattgttgc taatcttctt atgcaatttc cttttttgtt   2820
attattactt attttgaca gtgttgaaaa tgttcagaag gttgctctag attgagagaa   2880
gagacaaaca cctcccagga gacagttcaa gaaagcttca aactgcatga ttcatgccaa   2940
ttagcaattg actgtcactg ttccttgtca ctggtagacc aaaataaaac cagctctact   3000
ggtcttgtgg aattgggagc ttgggaatgg atcctggagg atgcccaatt agggcctagc   3060
```

| | |
|---|---:|
| cttaatcagg tcctcagaga atttctacca tttcagagag gccttttgga atgtggcccc | 3120 |
| tgaacaagaa ttggaagctg ccctgcccat gggagctggt tagaaatgca gaatcctagg | 3180 |
| ctccaccccca tccagttcat gagaatctat atttaacaag atctgcaggg ggtgtgtctg | 3240 |
| ctcagtaatt tgaggacaac cattccagac tgcttccaat tttctggaat acatgaaata | 3300 |
| tagatcagtt ataagtagca ggccaagtca ggcccttatt ttcaagaaac tgaggaattt | 3360 |
| tctttgtgta gctttgctct ttggtagaaa aggctaggta cacagctcta gacactgcca | 3420 |
| cacagggtct gcaaggtctt tggttcagct aagctaggaa tgaaatcctg cttcagtgta | 3480 |
| tggaaataaa tgtatcatag aaatgtaact tttgtaaagc aaaggttttc ctcttctatt | 3540 |
| ttgtaaactc aaaatatttg tacatagtta tttatttatt ggagataatc tagaacacag | 3600 |
| gcaaaatcct tgcttatgac atcacttgta caaaataaac aataacaat gtgaaaaaaa | 3660 |
| aaaaaaaaaa aaaaaaaaa aaaaaaaaaa aaa | 3693 |

<210> SEQ ID NO 6
<211> LENGTH: 4457
<212> TYPE: DNA
<213> ORGANISM: Homo sapiens
<220> FEATURE:
<221> NAME/KEY: modified_base
<222> LOCATION: (349)
<223> OTHER INFORMATION: a, c, g, t, unknown or other

<400> SEQUENCE: 6

| | |
|---|---:|
| gtttaaacgg gccctctaga cgcgttgaca ttgattattg actagttatt aatagtaatc | 60 |
| aattacgggg tcattagttc atagcccatg atatcatatg gagttccgcg ttacataact | 120 |
| tacggtaaat ggcccgcctg gctgaccgcc caacgacccc cgcccattga cgtcaataat | 180 |
| gacgtatgtt cccatagtaa cgccaatagg gactttccat tgacgtcaat gggtggagta | 240 |
| tttacggtaa actgcccact tggcagtaca tcaagtgtat catatgccaa gtacgccccc | 300 |
| ctattgacgt caatgacggt aaatggcccg cctggcatta tgcccagtnc atgaccttat | 360 |
| gggactttcc tacttggcag acatctacgt attagtcatc gctattacca tggtgatgcg | 420 |
| gttttggcag tacatcaatg ggcgtggata gcggtttgac tcacggggat tttccaagtc | 480 |
| tccaccccat tgacgtcaat gggagtttgt tttggcacca aaatcaacgg gactttccaa | 540 |
| aatgtcgtaa caactccgcc ccattgacgc aaatgggcgg taggcgtgta cggtgggagg | 600 |
| tctatataag cagagctctc tggctaacta gagaacccct gcttactggc ttatcgagat | 660 |
| atctgcagaa ttcatctgtc gactgctacc ggcagcgcgc agcggcaaga agtgtctggg | 720 |
| ctgggacgga caggagaggc tgtcgccatc ggcgtcctgt gccctctgc tccggcacgg | 780 |
| ccctgtcgca gtgcccgcgc tttccccggc gcctgcacgc ggcgcgcctg ggtaacatgc | 840 |
| ttggggtcct ggtccttggc gcgctggccc tggccggcct ggggttcccc gcacccgcag | 900 |
| agccgcagcc gggtggcagc cagtgcgtcg agcacgactg cttcgcgctc taccccggcc | 960 |
| ccgcgacctt cctcaatgcc agtcagatct gcgacggact gcggggccac ctaatgacag | 1020 |
| tgcgctcctc ggtggctgcc gatgtcattt ccttgctact gaacggcgac ggcggcgttg | 1080 |
| gccgccggcg cctctggatc ggcctgcagc tgccacccgg ctgcggcgac cccaagcgcc | 1140 |
| tcgggccct cgcggcttc cagtgggtta cgggagacaa caacaccagc tatagcaggt | 1200 |
| gggcacggct cgacctcaat ggggctcccc tctgcggccc gttgtgcgtc gctgtctccg | 1260 |
| ctgctgaggc cactgtgccc agcgagccga tctgggagga gcagcagtgc gaagtgaagg | 1320 |
| ccgatggctt cctctgcgag ttccacttcc cagccacctg caggccactg gctgtggagc | 1380 |

```
ccggcgccgc ggctgccgcc gtctcgatca cctacggcac cccgttcgcg gcccgcggag    1440
cggacttcca ggcgctgccg gtgggcagct ccgccgcggt ggctcccctc ggcttacagc    1500
taatgtgcac cgcgccgccc ggagcggtcc aggggcactg gccagggag gcgccgggcg    1560 cttgggactg cagcgtggag aacggcggct gcgagcacgc gtgcaatgcg atccctgggg    1620
ctccccgctg ccagtgccca gccggcgccc cctgcaggc agacgggcgc tcctgcaccg    1680
catccgcgac gcagtcctgc aacgacctct gcgagcactt ctgcgttccc aaccccgacc    1740
agccgggctc ctactcgtgc atgtgcgaga ccggctaccg gctggcggcc gaccaacacc    1800
ggtgcgagga cgtggatgac tgcatactgg agcccagtcc gtgtccgcag cgctgtgtca    1860
acacacaggg tggcttcgag tgccactgct accctaacta cgacctggtg gacggcgagt    1920
gtgtggagcc cgtggacccg tgcttcagag ccaactgcga gtaccagtgc agcccctga    1980 accaaactag ctacctctgc gtctgcgccg agggcttcgc gcccattccc cacgagccgc    2040
acaggtgcca gatgttttgc aaccagactg cctgtccagc cgactgcgac cccaacaccc    2100
aggctagctg tgagtgccct gaaggctaca tcctggacga cggtttcatc tgcacggaca    2160
tcgacgagtg cgaaaacggc ggcttctgct ccggggtgtg ccacaacctc cccggtacct    2220
tcgagtgcat ctgcgggccc gactcggccc ttgcccgcca cattggcacc gactgtgact    2280
ccggcaaggt ggacggtggc gacagcggct ctggcgagcc cccgcccagc ccgacgcccg    2340
gctccacctt gactcctccg gccgtggggc tcgtgcattc gggcttgctc ataggcatct    2400
ccatcgcgag cctgtgcctg gtggtggcgc ttttggcgct cctctgccac ctgcgcaaga    2460
agcagggcgc cgccagggcc aagatggagt acaagtgcgc ggccccttcc aaggaggtag    2520
tgctgcagca cgtgcggacc gagcggacgc cgcagagact ctgagcggcc tccgtccagg    2580
agcctggctc cgtccaggag cctgtgcctc ctcaccccca gctttgctac caaagcacct    2640
tagctggcat tacagctgga gaagaccctc cccgcacccc ccaagctgtt ttcttctatt    2700
ccatggctaa ctggcgaggg ggtgattaga gggaggagaa tgagcctcgg cctcttccgt    2760
gacgtcactg gaccactggg caatgatggc aatttttgtaa cgaagacaca gactgcgatt    2820
tgtcccaggt cctcactacc gggcgcagga gggtgagcgt tattggtcgg cagccttctg    2880
ggcagacctt gacctcgtgg gctagggatg actaaaatat ttatttttttt taagtattta    2940 ggttttttgtt tgtttccttt gttcttacct gtatgtctcc agtatccact ttgcacagct    3000
ctccggtctc tctctctcta caaactccca cttgtcatgt gacagtaaa ctatcttggt    3060 gaattttttt ttcctagccc tctcacattt atgaagcaag ccccacttat tccccattct    3120
tcctagtttt ctcctcccag gaactgggcc aactcacctg agtcacccta cctgtgcctg    3180
accctacttc ttttgctctt agctgtctgc tcagacagaa cccctacatg aaacagaaac    3240
aaaaacacta aaaataaaaa tggccatttg cttttttcacc agatttgcta atttatcctg    3300
aaatttcaga ttcccagagc aaaataattt taaacaaagg ttgagatgta aaaggtatta    3360
aattgatgtt gctggactgt catagaaatt acacccaaag aggtatttat ctttactttt    3420
aaacagtgag cctgaatttt gttgctgttt tgatttgtac tgaaaaatgg taattgttgc    3480
taatcttctt atgcaatttc ctttttttgtt attattactt attttttgaca gtgttgaaaa    3540 tgttcagaag gttgctctag attgagagaa gagacaaaca cctcccagga gacagttcaa    3600
gaaagcttca aactgcatga ttcatgccaa ttagcaattg actgtcactg ttccttgtca    3660
ctggtagacc aaaataaaac cagctctact ggtcttgtgg aattgggagc ttgggaatgg    3720
atcctggagg atgcccaatt agggcctagc cttaatcagg tcctcagaga atttctacca    3780
```

-continued

```
tttcagagag gccttttgga atgtggcccc tgaacaagaa ttggaagctg ccctgcccat    3840
gggagctggt tagaaatgca gaatcctagg ctccacccca tccagttcat gagaatctat    3900
atttaacaag atctgcaggg ggtgtgtctg ctcagtaatt tgaggacaac cattccagac    3960
tgcttccaat tttctggaat acatgaaata tagatcagtt ataagtagca ggccaagtca    4020
ggcccttatt tcaagaaac tgaggaattt tctttgtgta gctttgctct ttggtagaaa    4080
aggctaggta cacagctcta gacactgcca cacagggtct gcaaggtctt tggttcagct    4140
aagctaggaa tgaaatcctg cttcagtgta tggaaataaa tgtatcatag aaatgtaact    4200
tttgtaagac aaaggttttc ctcttctatt ttgtaaactc aaaatatttg tacatagtta    4260
tttatttatt ggagataatc tagaacacag gcaaaatcct tgcttatgac atcacttgta    4320
caaaataaac aaataacaat gtgaaaaaaa aaaaaaaaa aaaaaaaaa aaaaaaaaa      4380 aaaggtagca gtcgacagat gaattccacc acactggact agtggatccg agctcggtac    4440
caagcttaag tttaaac                                                    4457
```

<210> SEQ ID NO 7
<211> LENGTH: 17534
<212> TYPE: DNA
<213> ORGANISM: Artificial Sequence
<220> FEATURE:
<221> NAME/KEY: modified_base
<222> LOCATION: (730)
<223> OTHER INFORMATION: a, c, g, t, unknown or other
<220> FEATURE:
<223> OTHER INFORMATION: Description of Artificial Sequence: Synthetic plasmid

<400> SEQUENCE: 7

```
catcatcaat aatataccttt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactggtacc gcggccgcct     360
cgagtctaga actagtggat cccccaaacg ggccctctag acgcgttgac attgattatt     420
gactagttat taatagtaat caattacggg gtcattagtt catagcccat gatatcatat     480
ggagttccgc gttacataac ttacggtaaa tggcccgcct ggctgaccgc ccaacgaccc     540
ccgcccattg acgtcaataa tgacgtatgt tcccatagta acgccaatag ggactttcca     600
ttgacgtcaa tgggtggagt atttacggta aactgcccac ttggcagtac atcaagtgta     660
tcatatgcca agtacgcccc cctattgacg tcaatgacgg taaatggccc gcctggcatt     720
atgcccagtn catgacctta tgggactttc ctacttggca gacatctacg tattagtcat     780
cgctattacc atggtgatgc ggttttggca gtacatcaat gggcgtggat agcggtttga     840
ctcacgggga ttttccaagt ctccacccca ttgacgtcaa tgggagtttg ttttggcacc     900
aaaatcaacg ggactttcca aaatgtcgta caactccgc cccattgacg caaatgggcg     960
gtaggcgtgt acggtgggag gtctatataa gcagagctct ctggctaact agagaaccccc    1020 tgcttactgg cttatcgaga tatctgcaga attcatctgt cgactgctac cggcagcgcg    1080
cagcggcaag aagtgtctgg gctgggacgg acaggagagg ctgtcgccat cggcgtcctg    1140
tgcccctctg ctccggcacg gccctgtcgc agtgcccgcg cttccccgg cgcctgcacg    1200 cggcgcgcct gggtaacatg cttggggtcc tggtccttgg cgcgctggcc ctggccggcc    1260
```

```
tggggttccc cgcacccgca gagccgcagc cgggtggcag ccagtgcgtc gagcacgact   1320
gcttcgcgct ctacccgggc cccgcgacct tcctcaatgc cagtcagatc tgcgacggac   1380
tgcggggcca cctaatgaca gtgcgctcct cggtggctgc cgatgtcatt tccttgctac   1440
tgaacggcga cggcggcgtt ggccgccggc gcctctggat cggcctgcag ctgccacccg   1500
gctgcggcga ccccaagcgc ctcgggcccc tgcgcggctt ccagtggggtt acggagacaa   1560 acaacaccag ctatagcagg tgggcacggc tcgacctcaa tggggctccc ctctgcggcc   1620
cgttgtgcgt cgctgtctcc gctgctgagg ccactgtgcc cagcgagccg atctgggagg   1680
agcagcagtg cgaagtgaag gccgatggct tcctctgcga gttccacttc ccagccacct   1740
gcaggccact ggctgtggag cccggcgccg cggctgccgc cgtctcgatc acctacggca   1800
ccccgttcgc ggcccgcgga gcggacttcc aggcgctgcc ggtgggcagc tccgccgcgg   1860
tggctcccct cggcttacag ctaatgtgca ccgcgccgcc cggagcggtc caggggcact   1920
gggccaggga ggcgccgggc gcttgggact gcagcgtgga gaacggcggc tgcgagcacg   1980
cgtgcaatgc gatccctggg gctccccgct gccagtgccc agccggcgcc gccctgcagg   2040
cagacgggcg ctcctgcacc gcatccgcga cgcagtcctg caacgacctc tgcgagcact   2100
tctgcgttcc caaccccgac cagccgggct cctactcgtg catgtgcgag accggctacc   2160
ggctggcggc cgaccaacac cggtgcgagg acgtggatga ctgcatactg gagcccagtc   2220
cgtgtccgca gcgctgtgtc aacacacagg gtggcttcga gtgccactgc tacccctaact   2280 acgacctggt ggacggcgag tgtgtggagc ccgtggaccc gtgcttcaga gccaactgcg   2340
agtaccagtg ccagcccctg aaccaaacta gctacctctg cgtctgcgcc gagggcttcg   2400
cgcccattcc ccacgagccg cacaggtgcc agatgttttg caaccagact gcctgtccag   2460
ccgactgcga ccccaacacc caggctagct gtgagtgccc tgaaggctac atcctggacg   2520
acggtttcat ctgcacggac atcgacgagt gcgaaaacgg cggcttctgc tccggggtgt   2580
gccacaacct ccccggtacc ttcgagtgca tctgcgggcc cgactcggcc cttgcccgcc   2640
acattggcac cgactgtgac tccggcaagg tggacggtgg cgacagcggc tctggcgagc   2700
ccccgcccag cccgacgccc ggctccacct tgactcctcc ggccgtgggg ctcgtgcatt   2760
cgggcttgct cataggcatc tccatcgcga gcctgtgcct ggtggtggcg cttttggcgc   2820
tcctctgcca cctgcgcaag aagcagggcg ccgccagggc caagatggag tacaagtgcg   2880
cggccccttc caaggaggta gtgctgcagc acgtgcggac cgagcggacg ccgcagagac   2940
tctgagcggc ctccgtccag gagcctggct ccgtccagga gcctgtgcct cctcaccccc   3000
agctttgcta ccaaagcacc ttagctggca ttacagctgg agaagaccct ccccgcaccc   3060
cccaagctgt tttcttctat tccatggcta actggcgagg gggtgattag agggaggaga   3120
atgagcctcg gcctcttccg tgacgtcact ggaccactgg gcaatgatgg caattttgta   3180
acgaagacac agactgcgat ttgtcccagg tcctcactac cggggcgcagg agggtgagcg   3240 ttattggtcg gcagccttct gggcagacct tgacctcgtg ggctagggat gactaaaata   3300
tttatttttt ttaagtattt aggttttttgt ttgtttcctt tgttcttacc tgtatgtctc   3360
cagtatccac tttgcacagc tctccggtct ctctctctct acaaactccc acttgtcatg   3420
tgacaggtaa actatcttgg tgaattttt tttcctagcc ctctcacatt tatgaagcaa   3480
gccccactta ttccccattc ttcctagttt tctcctccca ggaactgggc caactcacct   3540
gagtcaccct acctgtgcct gaccctactt cttttgctct tagctgtctg ctcagacaga   3600 accccctacat gaaacagaaa caaaaacact aaaaataaaa atggccattt gcttttttcac   3660
```

```
cagatttgct aatttatcct gaaatttcag attcccagag caaataatt ttaaacaaag   3720 gttgagatgt aaaaggtatt aaattgatgt tgctggactg tcatagaaat tacacccaaa   3780
gaggtattta tctttacttt taaacagtga gcctgaattt tgttgctgtt ttgatttgta   3840
ctgaaaaatg gtaattgttg ctaatcttct tatgcaattt cctttttgt tattattact    3900 tatttttgac agtgttgaaa atgttcagaa ggttgctcta gattgagaga agagacaaac   3960
acctcccagg agacagttca agaaagcttc aaactgcatg attcatgcca attagcaatt   4020
gactgtcact gttccttgtc actggtagac caaaataaaa ccagctctac tggtcttgtg   4080
gaattgggag cttgggaatg gatcctggag gatgcccaat tagggcctag ccttaatcag   4140
gtcctcagag aatttctacc atttcagaga ggccttttgg aatgtggccc ctgaacaaga   4200
attggaagct gccctgccca tgggagctgg ttagaaatgc agaatcctag gctccacccc   4260
atccagttca tgagaatcta tatttaacaa gatctgcagg gggtgtgtct gctcagtaat   4320
ttgaggacaa ccattccaga ctgcttccaa ttttctggaa tacatgaaat atagatcagt   4380
tataagtagc aggccaagtc aggccccttat tttcaagaaa ctgaggaatt ttcttttgtgt  4440 agctttgctc tttggtagaa aaggctaggt acacagctct agacactgcc acacagggtc   4500
tgcaaggtct ttggttcagc taagctagga atgaaatcct gcttcagtgt atggaaataa   4560
atgtatcata gaaatgtaac ttttgtaaga caaaggtttt cctcttctat tttgtaaact   4620
caaaatattt gtacatagtt atttatttat tggagataat ctagaacaca ggcaaaatcc   4680
ttgcttatga catcacttgt acaaaataaa caaataacaa tgtgaaaaaa aaaaaaaaa   4740 aaaaaaaaa aaaaaaaaa aaaaggtagc agtcgacaga tgaattccac cacactggac    4800
tagtggatcc gagctcggta ccaagcttaa gtttgggctg caggaattct gatggctctc   4860
aaaattcctg cctcctttag ggataaaaga ctttaagact ttttaacaaa aagaaaaag    4920 aaaaaaaaaa ttcctgcctc ctggtgtaca cacacagaag ggttccctcc ccttgaatgt   4980
gaccaggatc tgtgaaaata acgggatagc cgctcctgtg attaggttat gtggtagact   5040
agagcaagat tctcctgctg gttttgaaga agtcagctgc catgttgtga gactgtcatg   5100
ggctagggca tgagcctta aatatctggg agcaaccct ggccagcagc cagtgagaaa     5160
acgggccctc agtcctacaa tcacaaggaa ctaaattctg ccaacaacct gaaggaactt   5220
tgaagaggat catgagtccc ttgattcagc ttgatgagcc cctgagcaga ggatacagct   5280
aacttgtact agggaagtat aaaaaacatg catgggaatg atatatatca actttaagga   5340
taattgtcat acttctggga atgaagggaa agaaatgggg ctttagttgt attatgatct   5400
ttaatttctc aaaaaaaata agatcagaag caaatatggc aaaatgttaa tacttttgtg   5460
ggtacgtagg tattcagcat acccttttt ctgagttcaa aatatttat aattaaaatg     5520 aaatgcaggc caggcacagt ggctcatgcc tataatacca gcactttgcg aggccgaggt   5580
gggaggatgg cttgaggcca gaccagcctg gccaacatgg caaaccccca tctctactta   5640
aaaaaaaaaa aactatatat atatatatgt gtgtgtgtgt gtatatatat atatgtatat   5700
atatttatat atgtgtgtat atatatatat gtatatatat ttatatatgt gtgtgtatat   5760
atatatatac acacacacac atatatacat acatacatac acacacacac acacacaatt   5820
agccaggcat ggtggcgcac acctgtagtc ccagctactt gggaggctga gacatgagaa   5880
ttgcttgaac ctgggaggca gagtagttag tgagctgaga tcataccact gcactccagc   5940
ctggtgacag agtgagactc tgtcttaaaa aaaataaaaa ttaaaattaa atgcaaaagg   6000
tccaagtgaa ttgaagagga aagggtatc aaggaaggtt ttgtggaggt gacgtttgag    6060
```

```
ctgggtctta aatgacttaa acatgggata agaagggagg gaataaggac atttcaggta    6120
cgagaaataa ggagcaaaca gtggaaacaa cctaacgtct gtcaaccagt gaatggataa    6180
caaaaatgta attcagatgg tatccaactt acgatggttc aacatgagat ttttctgact    6240
ttaggataga tttatcaaag tagtaaatcc attttcaact tatgatattt tcaacttcag    6300
atgggtttat caggacacag ttgaggaaca cctgtctatc catacaattt ggcaataaaa    6360
aggaaatgag tgcagatata ctccacaaca tgaatgaacc ttgaaaacat taagtgagag    6420
aagccagata caaaggcca catattgtat gattctattt atacaaaatg tccagaatag    6480
gcaaatctta tagacagcaa gtaggtagat gatcagtttg ctaggtgctg ggggaagggg    6540
aaatggggag tgatggctaa ggggattggg tttctttgtg gggcaatgaa aatgttttaa    6600
aattgagcgt gataatgatt gcacaatgct gcatatatat ataatctata gattatatat    6660
atataaagag aggctgttag acagtgataa gtgatatata tatatatata catagagaga    6720
gagagagaga gagagagagg ctgttagtga taagtgatca ggaaaataaa agtattgagg    6780
aggaatacga agttgacggt gtgaaaacat gagatttat ataggatggc cagggaaggc     6840
cttaatgaga aagtgactta tgagtaaaaa caagggatcc taaaccttag catgcatcag    6900
aatcactcgg aaacttgtta aagcatagct tgctgggcct catcacagat attttgattc    6960
ggtaggttct tgtctgatat taatactttt ggtctaggga accacatttt gagaaccact    7020
gagctaaagg aagtaaaggt ttcccttagt ttactagctg gtaacactgg cccaggaggc    7080 cttttctggtg acccctaagg aattatccaa actcttgttt ttagatgctt tattatatca    7140
aactctcctt taaacaagtg gcccatctgc tgggatttgg aagcctgtaa tactgaaatt    7200
ttcatcataa tggaaatttt aaaaacagaa tttgacccac ctgttttaa aacactttca     7260 ttacttaaca agaggtctaa tcttgggcaa gtcttgaaat ttctctggcc ttagtttccc    7320
atgtgttaaa tgaaacttga agcagttggt ctcttatagt ctcctgactc taacattcta    7380
agaattatat ttgtacaata actcaaaaat cacataattt aatttaccat atggactcca    7440
aaatatattt tctcattagg ctaaacttga tctgcatttt ctggatgtgt ccatattctt    7500
ggactacact aaaacatgat accaatgctt cctctcacca taaaccctca cttcgctttc    7560
tacatttaag aattttatag ctggaagagt ccttaacaga aaataccatc taataattac    7620
ccctcaaaat cgagaaagtc ctatctgttc ttatgctagt tataagaatg aggcagcatt    7680
tcacataatg gttataaaca ctgccacaag aagattcatg atgtgttgtt tatctgtagc    7740
tctcatcata ctctgtcata taactatagc attaagattt taatgttcta tatattcttc    7800
taagacagtg tttaccagag taaggcacaa aagatccact ggtttgcaag aaagattaga    7860
acttttaaat tttttacctc accttgttta atctatattt ttgtatgtat tttgtaacat    7920
atatattatt attaccataa atcatatata atttaaaatg catatattag gggtaaatgc    7980
tcaggaaact tttataaaat tgggcatgca aatacaagtt tgaagactca ctgttctagg    8040
tattaaaagt aaagttataa ccaagtaaag cttccacctt ttcatgtctc aaagcagttt    8100
attgttggag gtaagatctc ttagaagcct aaacaggtcc aagtacagaa tgaagtaagg    8160
ctagcccata acttgtggca agcaattcat actatttctc tcatgctgag ctctcctcag    8220
tgaagcagct actatagaca actgcagcct attggtagcc tattttacag gcaggaaaaa    8280
aattactttt tattcaaagt ggaactcagg acatggggag aaaatgaata caaaaaatag    8340
ggtcaatcca aaggcacaca gcaaatgagt aacacagtta tgttttttc ccatttgtat     8400 gaggtcccag taaattctaa gtaaactgca aatttaataa tacactaaaa aagccatgca    8460
```

```
attgttcaaa tgaatcccag catggtacaa ggagtacaga cactagagtc taaaaaacaa    8520
aagaatgcca ttattgagtt tttgaattat atcaagtagt tacatctcta cttaataaat    8580
gagaaaaacg aggataagag gccatttgat aaaatgaaaa tagccaagaa gtggtattag    8640
agacttgaat acaggtattc gggtccaaag ttcatctgct caaatactaa ctggggaaaa    8700
gagggaaaaa tatttatata catatatatc tgcacacaaa ataccccca aaagacaaaa    8760 tgaggccagg cagggtggct cacacccgta atcccggtac tttgggaggc tgaggcaggt    8820
ggatacctga gatcaggagt tggagatcag cctggtcaac atggtgaaac cctgtctcta    8880
ctaaagataa aaaattagc caggcatggt ggcgtgcgcc tgtaatccca gctacttggg    8940
agtctgaggc aggagaatca cttgaactgg aaggggagg ttgcagtgag ccaagatcgt    9000
actactgcac tccagcctgg gcagcagagt gagactccat cacaaaaata aataaataaa    9060
taaaatacaa tgaaacagaa agttcaaata atcccataat cttaccacca agaaataact    9120
ttcactcgtt atacttattg attttttccat aataaatgta ctttactgtg actatcatga    9180
aaagaaagtt atttttagaaa cagagaactg tttcagatca aatctatgta gtagaacaga    9240
gccattaggt gggaaagacg agatcaaact aaatctcaga aggcctaaaa ggctaggtcc    9300
attccagcac taaaaactga ccagacaagt aatggcttca acagcttcta aatatggaca    9360
aagcatgctg aaagggaagg acaggtctaa cagtgggtata tgaaatgaac aggagggggca    9420 aagctcattt ctcctctgaa gttttccaaa gatgctgagg aggacattag tttgacatga    9480
ccctgatatg ggacaagata atttcacaga agttttacat gttaaagttt tcttatagat    9540
actcattcaa gtaagcaatg aacactaaaa tctaaagaaa gaaaagagct ttagagtcag    9600
gtctgtattc aaattcaagc tctaccactt actggttctg tgactttggg caagtctttt    9660
aaccttatta agtcttaatt tcctgatttg taaaatgggg atatcgtctc cctcacagga    9720
ttgttgtgaa acttttatga gattaatgcc tttatatttg gcatagtgta agtaaacaat    9780
aactggcagc ttcaaaaaaa aaaagcagta gcattccatc atttattatt ggttactctc    9840
aaaaagtttt tcaatgtact agaagataaa tattcaaata ccttaatatc tccattattt    9900
tcaggtaaac agcatgctcc tgaacaacca atgggtcaac aaataaatta aaagggaaat    9960
ctaaaaacat cttgatatta aactacatgg aagcacaata taccaaaacc aatggttcac    10020
actaggagaa ttttaaggta caagaaaact ctttgagatt tcttaaaata atagtatgtc    10080
tgaatttatt gagtgattta ccagaaactg ttgtaagagc tctacttgca ttatagcact    10140
taatcctctt aactctatgg ctgctattat caacctcacc ctaatcacat atgggacaca    10200
gagaggttaa gtaacttgcc caaggtcaga gttaggaagt actaagccat gctttgaatc    10260
agttgtcagg ctccggaact cacactttca gccactacat aatactgctt tgctatcttt    10320
taggaaacta tgtgagtcta cctcacatag actcacatag gtttgttttt tttttttttt    10380
taaaggctat cttttccccc atcaatgttt tttgaaggat cccaaattag agtcccacag    10440
aggcagacag cagtacttga caatatggac atttaaggtt aatgttggat tctactgtct    10500
ttttactaca tgacctaggg aacgataatt aacctagact gcttccaagg gttaaataac    10560
ccatttagtt atactatgta aattatctct tagtgattga ttgaaagcac actgttacta    10620
attgactcgg tatgaagtgc ttttttttcct tcccttcaa gatacatacc tttccagtta    10680
aagttgagag atcatctcca ccaattactt ttatgtcccc tgttgactgg tcattctagt    10740
taaaaaaaaa aaaaactata tatatatata tctacacaca catatgtata tgtatatcct    10800
tatgtacaca cacaaacttc aaattaaatg agaactagaa gatttgagaa gttagctagc    10860
```

```
taatatccat agcattatga tattctaaat gatatgaatt ataagaatta ggtttcctga    10920
aatgaatgac tagaaaactt tcaagtagag attagtaaaa attaaaaagt cctaatcggc    10980
cattactgat tgatgtttt taagagtcct aaaaaatggg ttacatccat ttttaagtgg     11040
gtagtattat aacagccacc catcttcaat cacagtgatt tctgaattgt gagggaagtt    11100
attagcatga caggtgtctg gttctggccc tgtacgattc ccatgagtca agcaaattgt    11160
aagggctggt ctatatcaca cccaacccca aggatatgtc cctcaaaagt ctagcccagg    11220
ccccgtcatc ttcagcatca tctgggaaac caggtctgat tagtagtcct ttaaggaata    11280
cctcttaggc tcccatttta ctgctatcac agaatccaat aaaaccctta caggagattc    11340
aatgggaaat gctcaacacc cactgtagtt ggtggtgaca atgaccataa tttggctgtg    11400
ctggattcag acagaaaat ttgggtgaaa gagcaggtga acaaagagc ttcgacttgc      11460 cctagcagag agcaagccat accataccac aaagccacag caattacaac ggtgcagtac    11520
cagcacagta aatgaacaaa gtagagccca gaaacagacc cagaactata tgaggattta    11580
gtatacaata aagatggtat ttcgagtcag tagggaaaag atgaattatt caataaatga    11640
tgtttggcca actagtaacc catttgggaa aaaataaaag tatggtccct acctcacagc    11700
atacacaaaa ataaattcca gacggattaa aatctaaatg taaaaaataa agccataagt    11760
ggactggaag aaaatagaga attttttta acatccgtag aaagggtaaa acccaggca     11820 tgacatgaac caaaactgaa gaggttctgt aacaaatacc ccctttata tattgggctc     11880 caacaataag aacccatagg aaaatggaga atgaacacaa atagacaatt tatagaagag    11940
aaggttataa ggtgtaaaat tatatctatc tgagaaacaa acactaaaac aatgtgattc    12000
tactgttctc ccacccatac tggcaaaact taagcctgat aatatgctga ggggaaataa    12060
gcactcttgt tggtgagagt attaattggc atagcttctt ttgaaaatga catagcaata    12120
cctgttaaaa ttgcaaacat gcatgtcact taatccagta atcccacttc tgggaatcaa    12180
tgctacaaaa acactgacaa gtatacaaag atacattcaa gagtgttcac tgggccgggt    12240
gcggtggctt catgcctgta atcccaggga ggcagaggca agacgatcgc ttgaccccag    12300
gagttcaagg ccagcccgag aaacacagca agaccctgtc tctcttttt ttatttaaaa    12360 aataaatgtt cactgtatca gttgttcaca aaaacaaacc aacatgtcca ttaacaggga    12420
accatttaaa ttaatcaagt tcatctacac aatgtaatac catgcaacta ttaaaaagca    12480
cctgataatc caaagcacac tgagacagaa taatgctatt aaaaacacca agtagtggaa    12540
cactgtgttg cctatgacac catttttatt caacatttaa acaaatttgt aacagcaatt    12600
acatgagtag tgacaatggc gtttatgaga cttttcactt ttatgtgctt ctattttgt     12660 tatgcttcta tatatacatc catttattat ggagtgttac tttcaaaaat cacaaatggg    12720
ccagtattat ttggtgttgc aaggtgagca tatgacttct gatatcaacc tttgcatatt    12780
acttctcaat ttagggaaat tacagacatc ccttattcta actaacttaa aacccagcat    12840
ttcaaacata cagaattgat ggggaaaaaa aagaagaag aaagaaagaa aaggcaacaa    12900
gcttcagatg acagtgactc acatcaaatt atttataaaa tctgttaaat agtgccatct    12960
tctggagata cctggtatta cagtccaact ccagttgatg tctttacaga gacaagagga    13020 ataaggaaa aaatattcaa gaactgaaaa gtatggagtc atggaaaaat tgctgtgatc    13080
caaaggctac ggtgatagga caagaaacaa gagaactcca agcagtaaga cactgctgtt    13140
ctattagcat ccaaacctcc atactcctgt tgccccaag cttttttaa aaaatagaga    13200 caggatctca ctattttgct caggctggtc ttgaactcct ggactcaagc tatcctcctg    13260
```

```
cctcggcctc ctaaagtgcc gagattacag gcttgagtca ccatacctgg ctatttattt   13320
tttcttaact ctccttgcctg gcctatagcc accatggaag ctaataaaga atattaattt   13380
aagagtaatg gtatagttca ctacattgga atacaggtat aagtgcctac attgtacatg   13440
aatggcatac atggatcaat taccccacct gggtggccaa aggaactgcg cgaacctccc   13500
tccttggctg tctggaacaa gcttcccact agatcccttt actgagtgcc tccctcatct   13560
ttaattatgg ttaagtctag gataacagga ctggcaaagg tgaggggaaa gcttcctcca   13620
gagttgctct accctctcct ctaccgtcct atctcctcac tcctctcagc caaggagtcc   13680
aatctgtcct gaactcagag cgtcactgtc aactacataa aattgccaga gaagctcttt   13740
gggactacaa acacataccc ttaatgtctt tatttctatt ttgtctacct cttcagtcta   13800
ggtgaaaaaa taggaaggat aatagggaag aactttgttt atgcctactt atccgcccct   13860
aggaattttg aaaacctcta ggtagcaata agaactgcag catggtatag aaaaagagga   13920
ggaaagctgt atagaaatgc ataataaatg gcaggaaaaa gaactgcttg gaacaaacag   13980
ggaggttgaa ctataaggag agaaagcaga gaggctaatc aacaaggctg ggttcccaag   14040
agggcatgat gagactatta ctaaggtagg aattactaag ggctccatgt cccccttagtg  14100 gcttagtact atgtagcttg ctttctgcag tgaacttcag acccttcttt taggatccta   14160
gaatggactt ttttttttta tcggaaaaca gtcattctct caacattcaa gcaggcccca   14220
agtctaccac actcaatcac attttctctt catatcataa tctctcaacc attctctgtc   14280
cttttaactg ttttttctata ccctgatcaa atgccaacaa aagtgagaat gttagaatca   14340 tgtatttta gaggtagact gtatctcaga taaaaaaaa gggcagatat tccattttcc   14400
aaaatatgta tgcagaaaaa ataagtatga aaggacatat gctcaggtaa caagttaatt   14460
tgtttacttg tattttatga attccctaaa acctacgtca cccgcccgt tcccacgccc    14520 cgcgccacgt cacaaactcc acccctcat tatcatattg gcttcaatcc aaaataaggt   14580
atattattga tgatgttaat taacatgcat ggatccatat gcggtgtgaa ataccgcaca   14640
gatgcgtaag gagaaaatac cgcatcaggc gctcttccgc ttcctcgctc actgactcgc   14700
tgcgctcggt cgttcggctg cggcgagcgg tatcagctca ctcaaaggcg gtaatacggt   14760
tatccacaga atcaggggat aacgcaggaa agaacatgtg agcaaaaggc cagcaaaagg   14820
ccaggaaccg taaaaaggcc gcgttgctgg cgttttttcca taggctccgc cccctgacg   14880 agcatcacaa aaatcgacgc tcaagtcaga ggtggcgaaa cccgacagga ctataaagat   14940
accaggcgtt ccccctggaa gctccctcg tgcgctctcc tgttccgacc ctgccgctta   15000
ccggatacct gtccgccttt ctcccttcgg gaagcgtggc gctttctcat agctcacgct   15060
gtaggtatct cagttcggtg taggtcgttc gctccaagct gggctgtgtg cacgaacccc   15120
ccgttcagcc cgaccgctgc gccttatccg gtaactatcg tcttgagtcc aacccggtaa   15180
gacacgactt atcgccactg gcagcagcca ctggtaacag gattagcaga gcgaggtatg   15240
taggcggtgc tacagagttc ttgaagtggt ggcctaacta cggctacact agaaggacag   15300
tatttggtat ctgcgctctg ctgaagccag ttaccttcgg aaaaagagtt ggtagctctt   15360
gatccggcaa acaaaccacc gctggtagcg gtggttttttt tgtttgcaag cagcagatta   15420
cgcgcagaaa aaaaggatct caagaagatc ctttgatctt ttctacgggg tctgacgctc   15480
agtggaacga aaactcacgt taagggattt tggtcatgag attatcaaaa aggatcttca   15540
cctagatcct tttaaattaa aaatgaagtt ttaaatcaat ctaaagtata tatgagtaaa   15600
cttggtctga cagttaccaa tgcttaatca gtgaggcacc tatctcagcg atctgtctat   15660
```

```
ttcgttcatc catagttgcc tgactccccg tcgtgtagat aactacgata cgggagggct    15720
taccatctgg ccccagtgct gcaatgatac cgcgagaccc acgctcaccg gctccagatt    15780
tatcagcaat aaaccagcca gccggaaggg ccgagcgcag aagtggtcct gcaactttat    15840
ccgcctccat ccagtctatt aattgttgcc gggaagctag agtaagtagt tcgccagtta    15900
atagtttgcg caacgttgtt gccattgctg cagccatgag attatcaaaa aggatcttca    15960
cctagatcct tttcacgtag aaagccagtc cgcagaaacg gtgctgaccc cggatgaatg    16020
tcagctactg ggctatctgg acaagggaaa acgcaagcgc aaagagaaag caggtagctt    16080
gcagtgggct tacatggcga tagctagact gggcggtttt atggacagca agcgaaccgg    16140
aattgccagc tggggcgccc tctggtaagg ttgggaagcc ctgcaaagta aactggatgg    16200
ctttcttgcc gccaaggatc tgatggcgca ggggatcaag ctctgatcaa gagacaggat    16260
gaggatcgtt tcgcatgatt gaacaagatg gattgcacgc aggttctccg gccgcttggg    16320
tggagaggct attcggctat gactgggcac aacagacaat cggctgctct gatgccgccg    16380
tgttccggct gtcagcgcag gggcgcccgg ttcttttgt caagaccgac ctgtccggtg    16440
ccctgaatga actgcaagac gaggcagcgc ggctatcgtg gctggccacg acgggcgttc    16500
cttgcgcagc tgtgctcgac gttgtcactg aagcgggaag ggactggctg ctattgggcg    16560
aagtgccggg gcaggatctc ctgtcatctc accttgctcc tgccgagaaa gtatccatca    16620
tggctgatgc aatgcggcgg ctgcatacgc ttgatccggc tacctgccca ttcgaccacc    16680
aagcgaaaca tcgcatcgag cgagcacgta ctcggatgga agccggtctt gtcgatcagg    16740
atgatctgga cgaagagcat caggggctcg cgccagccga actgttcgcc aggctcaagg    16800
cgagcatgcc cgacggcgag gatctcgtcg tgacccatgg cgatgcctgc ttgccgaata    16860
tcatggtgga aaatggccgc ttttctggat tcatcgactg tggccggctg ggtgtggcgg    16920
accgctatca ggacatagcg ttggctaccc gtgatattgc tgaagagctt ggcggcgaat    16980
gggctgaccg cttcctcgtg ctttacggta tcgccgctcc cgattcgcag cgcatcgcct    17040
tctatcgcct tcttgacgag ttcttctgaa ttttgttaaa attttttgtta aatcagctca    17100 ttttttaacc aataggccga aatcggcaaa atcccttata aatcaaaaga atagaccgag    17160
atagggttga gtgttgttcc agtttggaac aagagtccac tattaaagaa cgtggactcc    17220
aacgtcaaag ggcgaaaaac cgtctatcag ggcgatggcc cactacgtga accatcaccc    17280
taatcaagtt ttttggggtc gaggtgccgt aaagcactaa atcggaaccc taaagggagc    17340
ccccgattta gagcttgacg ggaaagccg gcgaacgtgg cgagaaagga agggaagaaa    17400
gcgaaaggag cgggcgctag ggcgctggca agtgtagcgg tcacgctgcg cgtaaccacc    17460
acacccgccg cgcttaatgc gccgctacag ggcgcgtcca ttcgccattc aggatcgaat    17520
taattcttaa ttaa                                                     17534
```

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtaacactgg cccaggaggc ctttctggtg acccc                              35

```
<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgaccgggtc ctccggaaag accactgggg att                               33

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tagttccttc tgcctggaat ac                                           22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caagtcacaa ggatggacta ca                                           22

<210> SEQ ID NO 12
<211> LENGTH: 18524
<212> TYPE: DNA
<213> ORGANISM: Homo sapiens

<400> SEQUENCE: 12
tagttccttc tgcctggaat acttcctcat ctcacttgct ttcctgcctg gcagcttcct   60
acttgccctc tggaaccagc tctagggtca ccacatctct gcttctgagt gcctcctcag  120
acacagtctg tatttcctct tccaagctct catcacaaac attgtgctgt attatatgtt  180
tctgtgtggt cttccttcta tgaggaagcc ttggaaagca ggagacttat tttagtcttc  240
tttatgtttc ttttattccc aacacattat gtctgcccca tagacttttt caataaatga  300
ttattgagtt agtgactcct tttacatgct gacaaatgtg gctcttatta ctccccattt  360
cagtatcaca tatttgtaaa agtgaatcct tcttaatcgt tttacttttc tcctagtaaa  420
ttcctcatct atgcctgtct gctgctgttc tctgtgctgc tggcccttcg tttggatggc  480
atcatacagt ggagttactg ggctgtcttt gctccaatat ggctgtggaa gttaatggtc  540
attgttggag cctcagttgg aactggagtc tgggcacgaa atcctcaata tcggtaatac  600
tgctttatac aacccattgg tctctagcat gagggagcaa tatcttgact tttctcactt  660
ttgatgaagt aaggaccatt ttattttcta cctatctggg gtcttagaac tatagtataa  720
gctaacagat ctcttctgtg tttttgaaaa tttagtcttt ggtatgtatt ttcttacaaa  780
agcagtgcca tttgggggta agttgccagc cagctcacag atgcctatat aatccaaaat  840
gcacccaaaa tacagaactg gtatgccata ctagactaag cagcatgaaa ccaccctgtt  900
tttaggaaaa gacactcata ttatgtttgg tcatgaaaga tctttctcca atacagtttt  960
```

```
ggaactggggg ctcccctttgt cccacccctcc tagtcccaga gctttaggac tattagcagt    1020 gtagggggagg tggcttgacc aggagaccat gagtccctga gacagcagct ggggaatgag    1080
gaaagtcaaa gattggatgc cgagaaggaa agcagagcct ttgggggcag gggagagggg    1140 tacccttttac cgtttccaac tcttgccctc cctgctcttg gatgcctccg ctggcccaaa    1200
ttcctgggag ttgctcacgc cagcatgcaa cctgcttgtt gctgggacct gcgagagtct    1260
ttcccttctc tgccacagag actgtaacta cataaaggga aaaggggga cttaagactg    1320 ggaggctatt atgaacctcc actgggaaaa tgaggagtac aggaattccc agaaggcagc    1380
tgctcatgtg ggaaaagtgt aaagttgaaa ctaccgcacc ttttttttt tttttttttt    1440 tttttttttt ttgagacaga gtttcgctct tgttgcccag gctggagtgc aatggtgtga    1500
tctcggccca ctgcagcctc cacatcccgg gttcaagtga ttctcctgcc tcggcctcct    1560
gagtagctgg gattacaggc acctgccacc atgcccagct aatttttttgt attttttagta    1620 gagatagggt ttcaccatgc caggctagtt ttgaactcct gacatcaggt gatccacccg    1680
ccttggcctc ctgaagtgct gggattacag gtgtgagcca ccacgtccgg ccactacatc    1740
aactttttaa attttttgttt actaaatatg aaaatgattc agattgtgta aattacatat    1800
cacatacatg tctaagaact gtaaaacagt tacacagaga gccttggcag gtgagggaca    1860
ttcatgtata gctgtttcag agttcttaga tttttttga aagattgatg acctgtgtgg    1920
ctgtatgtgt tttattttttt tatgagatat tttcagatat ctaatattaa ttgcttctca    1980
aagaatgcaa agttaaataa acatttaggt tctactaatt gatatttaga atatattcaa    2040
acttctcttt gttggtctta tttaagatgt tttgagcaag gaaaggaatt gtgtatgtgg    2100
ggttgaatgt aaggaatgta caggcgtggt cattctcatg ttaacattaa ccagtggaac    2160
atggttgggt cctacaggaa taacctctga tagcatttc tctatgatct aacttccggt    2220
gtatttgtca cccacaatac atgtatatca taaatgttca tctgtattt gaataaacat    2280 tgtaggcctt tcagatgcat tatagagcct tttcctgatt agcggcctta ccattgctca    2340
attgtagatc tgttaaggtt attgtgcatg atacttagct aattaaactg attttgttttg    2400 agaacagttt taactcttgt tcttctttct ctttcatgtg caggtgttaa tttatcttaa    2460
tggaatagaa aggaaaatga aaatcattta tacgttttat ttgcatttaa aaatagcacc    2520
taacaatagt tactactatc ttgaaatata actggcactt gttcatagaa ctagagttat    2580
ttttataata ttgtgtgaag ggtggtttac atggtttctt gaaaaatgag gatcatgaga    2640
cttaaggggt atttgcctgg ttttagcagc agaagcaaat cagcttgaat aatcttggaa    2700
gtaactcttg ttgttgaatt taaagatgtg aacagaagtg tttatgtaca ttgtcaggga    2760
aataagaact ggctattact tttgagaata tccttatacg gttaaaacat taaattctgg    2820
tttggttgta atgttcattt tgtattatgt agtagttctt cgatgtttca gagattgcct    2880
accaaagctt aggtttaagt tagctttcta cctgatttcc ctttgctttt gtcaaatttt    2940
caagtaaaat tcaaagtata aatataagtt ggtatttgcc ctgaactgct tgcttatagt    3000
ggagattctg aactgagggt gttttcttct tctctcccctt ttttagagca gaaggagaaa    3060
cgtgtgtgga gtttaaagcc atgttgattg cagtgggcat ccacttgctc ttgttgatgt    3120
ttgaagttct ggtctgtgac agaatcgaga gaggaagcca tttctggctc ctggtcttca    3180
tgccgctgtt ctttgttttcc ccggtgtctg ttgcagcttg cgtttggggc tttcgacatg    3240
acaggtcact agaggtgaga tttcatatat ttaagaatgt tttccacttt gggaggtcaa    3300
ggcaggtgga tcacttgagg tcaggagttt gagaccagcc tggccaacat ggtgaaaccc    3360
```

```
catctctact aataatacaa aaattagccg ggtgtggtgg catgcgccag taatcccagc   3420
ttctccggag gctgaggcgg gagaatctct tgaacccagg aggcggaggt tgcagtgagc   3480
caagattgaa ccattgcact ccagcctggg tgacagaatg aaactccgtc ttaaaaaaaa   3540
aaaaaaagaa tgttttcaaa agtaaaatat tttgctcagt tattcagatg tcaatttctt   3600 acccttttgtt aggaagagct tgatcattac caactctaca tcatgagaca acaaggcaac   3660
aaaagatgat ggaaataaca attttctttt cttcacttag aacactagct tttcacccag   3720
gacatcagcc ttctcccagc ttcacatcct gtatcaatca gacagaaaca gaactgatag   3780
gttagataca gatatatgta taaagagagt taaggaactg gctcacatta ctgtggggct   3840
ggcaagtctg aaatctccag ggcaggtgaa caggctggag acctaggagg agttgacact   3900
gcagtcctgg cacagaattt tttcctctcc aggaaaccac agttttttgct tttaaggcct   3960 tcacctgatt gcatgaggcc cacccatgct atggagggta gtctccttta ttcaaagtca   4020
gtaccttcac tgcaacagca agcttagtgt ttgattaaat aactgggtac tatagcccag   4080
ccaagttgac actcaaaact gaccatctcc ccacctcaga ccccatgatt tagcacctcc   4140
cctgctgtct ggttagctta tcctgatgtg cccctgtgtt tgtttattca ttcaataaac   4200
atttatcaag tatttactag atgccaagcc ctttttccct aagcatagag gatatgcaga   4260
tgaataaaat accaggacta gtaataatag taatgaaagt aattgcagat aacgtttatt   4320
gagcacttac tgtgtgccag gcattgtgcg aggcacatta catgtggtag ttttcttact   4380
aactaactct gtgaggtagg tccagagaag ataagtcatt tgttcatggc cacatgtgaa   4440
ggggcaggac caggattccg tttgagtcag cccgactcta aagcccgggc acataactac   4500
ataactgcat agaagctgag ggcccaaagc tgaatactga tgggttgagg ggagaactag   4560
aggctgtaga tgcctggttt tgagccgtgt ggatgaagag tgaagggaga agactgcagt   4620
tggcttagga agtaaacata gcagctgtag ggtgggtcag gcatataagc ctagacccca   4680
ggtatgggcg tgaggggaag gtatgtagac agagggacgg tgatggagca aggccctgtg   4740
ggactcaggg agaatgggac ctagagcacc aggaagggtt tggccttgaa caaggggagc   4800
tattccctga ttttcatgct ggtggaaagg ccacagcatg ggtatagtgg taggtaggag   4860
tgagccgtgg agggagagta tctgatggtc cactttcacc ctccctacaa ttcccagttt   4920
atatcaggga cttgagcatc catggatttt ggtatccaca gggggtcctg gaaccaatcc   4980
cccacagata ctgagggaca actatacaag gactaggact gcattgggcc tgaattacag   5040
aaagtaagtc tttcatatat tcacactcta ggcattcctg cccttggaag aaacaacata   5100
ccaggagctg agctccctcc tcctgtgatg caagaacagt acctatgttg gtgaggggt   5160 ggtctggagt aggctcatac agagatggga aggaggagtt gagggtctgc caggaagccc   5220
tgtgttggga gggaagggat ggcattttg ggacacattg aagcctagag gcaggaaaca   5280
ctccatcagc tgagtggact gtggcgattc agatccgacg ggagcacaag gtggaaggga   5340
aggaactgtg ggagttgaga agagagggag cctctacaga gggattgggg caaatagggg   5400
ccacgtcctc agcccacaga gcatgtgctg aagtgcccca ggcacccag tgcactcaca   5460 gggcaccagg ggatagtgga cattttgagg aaaacagtaa tacctgacat tgttgggac   5520 accatacaaa ctactagctt gaaatagttt acaggtttat ttttaggcca cactgcattc   5580
ctttcagtga cgtcgtatct ttaagaagct gggttttcag cagttgctgt gaaaacaaaa   5640
aaggctaatg ctgtgtgaaa atccgggtga agaacaggta acgagtggga gcaccttgtc   5700
tgattccaag gcgtgggaaa tggtgagcta cctgacaggc acacgcatcc cactgggaat   5760
```

```
tagttttggt tatttaagaa taatattaac attttctttt agatttatat gaattatttt   5820
ttctagtggc tacttagaaa tacttactaa gttagatgta attacttaaa tcagtgcaac   5880
tgttggcatt cccagccaca ttagggattt cttttggcct agaggtctat ggaggaatta   5940
ctaaattccc catgtaccta tgtactgaga acttttggga agctctgggc ctggtcccag   6000
atttcaattt tgtgggcaag aatgtacttt accagagtga ggagcagcct gcagggcgtt   6060
tgggctggag gcgggaggtt agtaaggggt tgctgaagtg gtaggcggat ggtgccgaag   6120
aaggcctcac taggcagtca tcatcaggat aggaagtggg cacgggattc aggagaaatc   6180
tggactttac agtggacagg atgtggtgac tgaacgtgac agtgtgggaa aaagaatgca   6240
gggtgattcc cgggctcatg gcttgagaaa tgagaccact gttgtgcctc caagtgacat   6300
gggaggctat agaaagtgac atgggaggct atagaaagtg acatgggagg ccatagaaag   6360
tgacatggga ggccatagaa agtgacatgg gaggccatag aaagtgacaa gggaggccat   6420
agaaagtgac atgggaggcc atagtgacat gggaggccat agaaagtgac atgggaggct   6480
atagaaagtg acatgggagg ccatagaaag tgacatggga ggccatagaa agtgacatgg   6540
gaggccatag tgacatggga ggccatagaa agtgacatgg gaggctatag aaagaggaga   6600
tacaaggttc taagtgcagg cgataatgat ctctatttgg gactggcttc atttgaggtg   6660
cctttaggag agccgagtgg cctatgcaca gctgggtctg ctatgcagca ggaaggctaa   6720
gttggagaca gatgtgagaa ctaaccatga aggaggtaat aatgcagacc aagggtctgg   6780
ttgaaatttc ttctccccca gtccagggtg cagcggtga gtgaaaatat gtgtgtttgt   6840
gtgtctgtct tcctagtcgg gagagaagac tgagtttgtg gctctgcgga gcatcaccat   6900
ttaaggaggg ggaaaaggag acagaaggaa ttaccagaac actccagagg gctccaagac   6960
tgtatggtgg gatctagatg gccaggagga ggggagcaaa aaggaaagag tcatccacag   7020
tatcagtagg atgccagttg aagtgttttt gctgcctccc ggttatcggt gactttgatg   7080
aaagctgtct tctggtggtc atggggtgg aggccagatc acaaggaagc tgggaatggt   7140
agatgagata gtaggggctt gcatattcat tactgtctcg cagagagaaa cctgaggcta   7200
agagggggtct tggatcaaag gatggggtgg gtttatctgg tttcggggct tttgttttta   7260
atgagaagga gtcatttctg tgctgctagg agggatcaat ggaataggtg gggttaaaga   7320
tacagtacgg aatctacagt tgatggcttg atgtgacaag gtcctcaagg agcctgaaag   7380
gaaggggtgg ggtccaaggg caaaaccgag gtatgagaag aaggatgcac aaggatggtt   7440
tcgagtagac agtattgttg gtagggacat gaaggaagtt tagtggtcta ttgcagctag   7500
cctgtgttcc cagtgaacct ggaaacaagg ttctcatctg tgctcaggcc tcaggccaga   7560
aagggcaagg cagcagaggg gcaaggcagc aggctgagcc ccatttcccc ttgccataat   7620
actgctgtgc ccctctggta ccgaaaatca ggagtttcca gtgcaatata atattataca   7680
agttacactg tattataatg tgtattgtct tttagtgtgt taaccaaatt actgcagtat   7740
taaatgcaaa ttatactttg tttaactgat tcttctcttc attttagtt agaaatcctg   7800
tgttctgtca acattctcca gtttatattc attgccttaa gactgacaa gatcatccac   7860
tggccctggc ttgtatgtaa cttttaaaat ccttaaataa acttcttttt tattataaaa   7920
gtaattcata ttcactgtac aaagcttgga aaagacggac aagcagaagt aatagcctaa   7980
tagtcaccca taatcccacc atggggagat aacatggtta gtgttttat gtctgtgttt   8040
tatacaaaca gtttggatat aactgtgtgc accattttgt atcctgattt ttttgtttta   8100
atgttgtatc ataaacattt tatcatgtta ataaaaggtc tttataaaca tgacttctaa   8160
```

-continued

```
agtttaattg atacaaaata ttcttcaagt gcatgtatca gaccatcctc ttatttctaa      8220
aatatggtat ttccattgtt gccagtgttg aatgatttta aatcatactg cagtatatat      8280
gtttatgcat taaaatttt gccttttgtt ttttggttgt tttcttagga aatagtccag       8340
aaatagtgtt actgagctag aggttgggaa ctatttgaga ttcctatata cgtatactgc      8400
actgccaact tgcttttcca aaagccatac ctggccaggc gcagtggctt acacttacag      8460
tcccagcact ttgggaggcc gaggtgagct gatcacttga gctcaggagt tcgagaccaa      8520
cctgtgcaat gtagcaagac cctgtctcaa aagaaaaaaa aaaaagcca tacccattta      8580 cactcttgct ggtggtggca tctatgtcat gcttctaaac tgtgacttca gttactgggc      8640
atttggttga aattaactgt gaataaatgg gtagatggat gcagagatag aaagataagt      8700
ggcaaggtag aaattagaga acacagtata gattccacta ttaaatgcat ggaaaaaaga      8760
tggagactaa aggcagaaga gttccattgc cactgggagg taaggtcatg ctagtgtttt      8820
tgttcggttt tattttctct gttgtttgat gtataatttt gcatacaata tattttatgt      8880
attaaatata gctacccta aaaagtgaaa agtatagtaa agaattggga gcagagaaga       8940
aatgaaggga acctaagtat actccatatt taaagatggg aataatcact ctgcccaaa      9000 gtctttgata aacattcat aataaaaaat attcagtcac tcatcctaca acttcacagt       9060
gctgtatctg gagaatggtc attgggttca aaactgtttc tgttgtgacg tgaaggaaac      9120
atatctaaac aagaccaaat ttttttcgtat aagatactgt cagggaaaaa aaagattagt     9180
aattttgaga gctttccaca aatgagaaga aagattttt ctgcccttca tcctctgtag       9240
atcccagttg atgaagcagt ctgagtacat gtttcccata gtgagcaaga gaaacaagg      9300 aagcctattg agatctaaca ttccacccat gaagggaact tcagtaaaaa ggagaatctc      9360
atcacagaat ggggaacggg gaagaaaggc tgtgcataga ctctgcagag aaacctacaa      9420
tcaagaactg gtcaggagaa gtaaaattcg tatgccaact caaatcatag atctaaaaga     9480
aaatgtaaaa ctatagatct gttaggaaat aacataggac agaatctttg gggtttgcaa     9540
ttaggcagag agtacttaga aatggcactg ttaatatggt ccatacgaga gagaaatcat     9600
aaatttggac ttcctcaaaa ttaaaatgaa atgaagacag gccacagact gggagaaaat     9660
atttgcaaag cacacatcaa aacactgact tgcacccaga acatacagag aactcttaaa     9720
aactcaaaac tgcaaaaaga aacacctaaa aattggcaaa agagttgaca atttgcgaag     9780
gggatataca catggcgaaa aagcacagga aaagatgctc aacgccatta caggttaggg     9840
aagacaaact acaaccagga tgagggcccg aaacacatgg cttcagaatg gtgaaactca     9900
gcaacactga cgaggccacg tgcctgggag gatgcagagg aactgggaca ctccagtgtt     9960
actggcggga aggcaggtgg tacgggcact gtagaaaatg gtttggccat ctctgatgca    10020
gttaaaagcg cacttcccgt gggacttggc tgccccactc ctgggtataa gatttacccc    10080
cagagaagtg aaagcgcgca gccttgtaga aacccacaca ccagtgtttg tagcagtctt    10140
gtttgcattt tggatagcgg ccttgtttgg ttttcacaaa ccaccctcag cggacagtca    10200
gataaactgt aggcatccat acaatggaat accactcaga tctgagaggg aacgacctgt    10260
ggatacaggg agggaacaac ttggatgaat ctcattagag acattatgtg gatggcggga    10320
agccagtctc aacaggttac ttgtctcgcg atgccatcta cataaagttc cagcagagac    10380
aaaagtacag tgagagaaca gatcagtgtt tgccggggct aatggtgggg acggtgtgat    10440
agtgaaggga cagcacggag agttttgcag ggtgacagac ctcttctgca tcctgccaac    10500
ggctgtgtga atctacttgt gtgaagactc agggaactca caccaaagga agacggtcac    10560
```

-continued

```
ttttcctact gtatgataga taattaataa aaagggagaa cggaggagtg tcgtcccagg    10620
aggcagggca ggagggcgaa gacgtgtcac aggggagcct ggccaagtgg cgcccccgga    10680
actcgtcctc tgggcttgtg tgtggatgag acaaggtcta cctggtacga cagggacata    10740
ctgggaatgc gcccttgccg tggaggcggg gacccggcag cgctacgtat ccagcatcaa    10800
cctgtatcca gcatcaaccc gccaagttca ctaacttggt aggggtgagg ttagggatcc    10860
ttaggagccc aggcagccag actttctggg agcccattc ccatttgtgt tgccaaagta    10920
cccccagcag gttgtgggaa tgttgcctgt gaagagagtc tgttggggtg agatcttgtg    10980
tgtgtgcaca gggtgacagt tgtgtcccat tccccgggaa gctgtgatgg cagcagaacc    11040
tagaggagcc tgagagagtg tgggagagtg ggcctctgga agagtagagg ctgcggagcc    11100
aggtgcaggg ctgtctgtca cccaaaggaa gagggactga tgactcactg agcgtgtgtg    11160
tcccctggtg gcagcaggcc ccatagtgaa cataccatac cttttctgtc ctgagcgatg    11220
ctcccagcag tcctgggaga tggaacggtc cttattcggc tcacaggaag gaccgcctta    11280
actggacaga cacagcaagg tgctaaagat gccttccatc agaggccagg ttggaagctc    11340
taaagagact tctcttgctg ttctctcacc cacccccagg ttgtgtgtgt cccgctgtgg    11400
attctcatgt cctttctgtg cctggtggtc ctctactaca ttgtgtggtc cgtcttgttc    11460
ttgcgctcta tggatgtgat tgcggacagc gcaggacaca cataaccatg gccctgagct    11520
ggatgaccat cgtcgtgccc cttcttacat ttgaggtaag cgttccacgg gaagcctctt    11580
cagcccctga agcttgcgct tcccctgaca ggattctgca ccctagaaa ggcagcctct    11640
gtccctcgag ctcacagtga gcccactcca ggagagggga gagaacacag ccatctccga    11700
gagggagctt cggtgaaagg agagcatcct tcctttctct tgggggcagc acgtggggct    11760
ggcagggaga agagtgcacc tttttagcca tggtgcctct gtatggctcc agtttccact    11820
ctggggaaag cagagtggga tgtcagattt gtgtattgga gtcacgtgga gaattctaga    11880
atgggagctg ttgactcctt agaacaaaca cccggaggag tttgccataa aactgctggc    11940
actgggaact tttcaagtgg ataggctatt gccgagctct gaagagggac ataaaagctc    12000
atttcgagct ttccccaggg ataggtggtt tcctgccttt ttctggcggt gctgatgttc    12060
cctcttgtgg gagctcacgc ggggtgggg tggtggggag gaactgccta atgaagtctg    12120
gcttccgcct ctgcccattt tcggtgctgg catcaaccgg gactatgtct cttctttag    12180
attctgctgg ttcacaaact ggatggccac aacgccttct cctgcatccc gatctttgtc    12240
cccctttggc tctcgttgat cacgctgatg gcaaccacat ttggacagaa gggaggaaac    12300
cactgtatgt actcagcatt tcagaagtcc ttggtgtgtg tctggggggg gaccagggg    12360
tggggggtgg cggatagaag tctaggaagg gatgagtccc cgagggcccc aatttagaag    12420
cttgtgtggg aaagtgaggg ctgaggaaat tctgggacct tctaagggaa gggcatgccg    12480
taactctggt gttctgctgg cctgcaccgg gacttttctc gcagtgcacg ctgccatttg    12540
aggtagaacc agacacggca ggcaacctct cagagatccc gttccctcct ctgcaaaatg    12600
gggatcaaga cagattcttc ccaggcccgg gagggtttga tggaaaatcc acatctccca    12660
cccaaacctg ggattcatcc taggtccctg ttggccgctc tgcctccccc atatccttgc    12720
tgccatcacc cgagtcttgc ctgtcttgcc ttgctaacac tctattcccc tccacctgct    12780
tgctgaggca gacacttcca aaacgatctc tgcagagggt gccttcctgg caaggctgtg    12840
ggctccatgg cacggaagcc cagagcattg cccttcggaa agccagtggg tttgggggca    12900
gggcctcact gcagcccagc agcccgggct gtgcttgctg tttgtgcctc tgcccccta    12960
```

-continued

```
cccgcacccg ggagcaggga gggcttgcac cgagctgaca ctccagtagc ctacagagag   13020
gagtagtggg actgggaaag tggctttaag gtggctccat gagttcaggc cccctcctgg   13080
ccaacccgtg catgactacc gccctcacgg attccagagg gtgacagaaa tcttgttctt   13140
gggtggcact gtcatccatg agtttatcct ggctggagaa gattagcgga agacaccgta   13200
gtctgcgcac cacagatatt ttgagactca ctggagcagt agttctcaaa tttgggcatc   13260
cagcagaatc ccaaaagggc caggaaaagg ggaccgctgg agcccaccct agcccgactc   13320
agtttctgga ggtctgggct ggggcccgag aatggcatcc ctaactaggc cccgtggacg   13380
ctgtccctgc cggtccggga accccactcc aagcaccaca gagctagcat ttgcacttct   13440
tccccatttt gggtactcaa gccctgttca ggctttgtga ctcaggagtc tggataaagt   13500
atgttatgac attgtaggag tgaaacttct tgttacggaa agaaagttaa caggaaggtc   13560
agttgagcct cgtgtgtgaa ataaaaaatt cttatttttc agggtggttt ggtatccgca   13620
aagatttctg tcagtttctg cttgaaatct tcccatttct acgagaatat ggaaacattt   13680
cctatgatct ccatcacgaa gataatgaag aaaccgaaga gaccccagtt ccggagcccc   13740
ctaaaatcgc acccatgttt cgaaagaagg ccagggtggt cattacccag agccctggga   13800
agtatgtgct cccacctccc aaattaaata tcgaaatgcc agattagatg ccacttccgg   13860
ggacagagct taagtggact gggacgcact ctctccgcct tcctctgccc cctcgttcac   13920
cccgcagacc agaaccagta ctggagctgg gtctccaggt acgtccatct catgccttgt   13980
ttgcatccag cgcctatcag ccactcacca cgacgggacg cggaagtggc aggtgacggg   14040
ggtgtgtgcc agcagatgcg gatgccagga agagtgtgag aacagggtg ggattaccgt   14100 ctgtctggga ggggctccag gtaccctct tccccgtcag acccactggg agatggctgc   14160
ttgccaggcc cccagaagga acatctgtct atacggtgct gaaatcccaa tcaaaagtat   14220
tgtttagaaa tgtatttctc cacagggctg acctcctgca gctcgctgag cactcccagg   14280
tcctcagcac tcccaggtcg tggctggggc agtcagtagg aactgtaact atgtctctga   14340
tgcaccacgt gtttagacac agcacagtcc ttttttctgt tcctactgtg gaagtagttt   14400
ctctttgggc atgctgacag cagttttttca tagcctcacg gatgagccct ttctacggga   14460
gtgactccat gcttgtatac agagtattta tacaaatgtt ttagcatctt catatgcgt   14520 gttaacccct agttctgtac agcatattct gttcaagtat ttttttacaa gcttgtgctg   14580
taggcacatg ccttctgctg cagaagtgga cgcccgtggc acactccccc ccccccccg   14640 tggggtgcca cgccttcatg ggacattgcc acttctgccc tggaactcgt gcaggtacgt   14700
agtagctgct actgccacaa cggcaacacc aagcaagaga tggtccatgc ttttctgacg   14760
ttctcagaat agtggctagc ttcaaacctg acaagcgctg cttgaagccg gaacactaga   14820
gaatgttgct gagagcagaa acggccacgc gggtcacgac tatgcgtggg aaagtctcaa   14880
gcttccctcc tgccagcaac aagaaggctt tggagtaggc atgatgtttt cacgtgtgcg   14940
tgccgtttct ccaagcactg caggttccac cgtgtgtcag aggctgcaag tttaacatcc   15000
tcctgcctga aaacaaatag gtcctttgct gaaaagaggg taaaaaaga ctttgatct   15060 tctcagccag gagaagaggg tggtgttttc acgcgggcaa ctgctcgccg gcctacatgg   15120
ggttaattca agtctgctgc gagcacgact ccgcccttgg cactggcctc cagcaagccc   15180
tgttctcttt ggggtacagg ggaacgggat ggtttagact ttcctgctca gtgtgtaaaa   15240
aatgtagcta aagccactat ttttgctctc cttaagctgt tcaataaacc ggttcctcat   15300
tttacacgtg catgatgtgt atcttctttg ctggatgggc caggaaactg gagtggtcct   15360
```

```
ctcagccagc ctcagaggaa agaaatctct agctggcaca ggcagccagt gagtgaggct   15420
ggcggctgca ggggcacagc ctttagaatg agtccttcag tgcacaggtc ccagggtata   15480
cggggtagtg ggaggaagga ggggacgcct cgcagatgcc actgttggct gggctacacc   15540
ttgccacact tgttactgct taggaggctt tctggagtgt tccttgggtg ctacgacaat   15600
ctgcagcaga cactgtcctt tcaccgctcc tggtcctcgt ttgctcccca gtgatgtcaa   15660
cagctgagga ctgctcacgc tgcaacaaaa ggctctgcag tcgctgtcta gcttgcccta   15720
gtcgtctcta gagttctgcc tgaactgaaa ctcaagtggg gttcagctca tgacttgtgg   15780
caattgacca ggaaattcac cagttgctgt ggctggaagg attttcagtc ctgtggggttg   15840
taaccagagg ccacaggtgg attctgcctt aggctcatga gatttccgac ttgctgttga   15900
agaaaatgcc ttgtgaagtg acaacagtag ctctgaccca actgccggtg cctcgctagt   15960
tcctatacgt cccactggat cctcacagcc ccgggaagca ggtgctacta ctcttatccc   16020
cgggaggaga cagaggccga gagaggttaa gtgacgtgcc caagtcacac agctcggcag   16080
cggccgggtt gagcatcagc agtctgtttg cagacccctc actgtcaccc cctgagccag   16140
tgcgccttgg gccctgcggt caggatgtct caagcgtgga ggcatcaccg gttcgtggca   16200
gtctctggaa ggtcactgag ctctgtgccc agaatcgagt cggggagtc tgtgcagagg   16260
tggccctgtg tgtggggaca gtgtgtgaca cagacactgc tttggatgga cacctctccc   16320
gtgacctcct agcatccaat cccaaaggaa caactgttgc agagatggac cgctggacac   16380
aaacccacgt gcgtttctct ggagacactg gccaaggaaa acaaaacatg ctcgaaggcc   16440
aacagctgca tgccccaccg cgatgtgacc gcagacaccc ggggtgtaga agggtctctg   16500
cctggtgggg ggacacgtgc aggccgagga gaggcaggaa ggaggctgcc tccgactccc   16560
cactggactg catggcgacg gcgtgtggtg gggcagtcag ctaagccatt tgcctaaggg   16620
gctgtcgggc atctgcgtgc tggggaccga cagtgtgggt gtgttaggag gatctgtatg   16680
gagcacattg ctgcctctgg ctaggacagg gtggaaaggg tggcgtggct acagcctgac   16740
ccatgggcac cgtcctaccc tttgttctgt gcttccgagt gtcagtcatg tgctggggtc   16800
tgtgggccca tgactcagac ggtgagctct gaccttcctg agccagggct ttgctgtagt   16860
tgtgcctggc tcaggagctc taggacaagg ggaccgctcc aggtctgcat ctacggtgtg   16920
gcagggcccc tcggcactct tgtgcactag tgtcatcttt cccattgaaa tgactgtgag   16980
gaccagaatg tgcacatgca gatgggcagc tacttgtctg ccttggccct ttattacaca   17040
acttgctggg ggtggagatg ccaccccccg gcagtcagag cccctttatg atgtcatggg   17100
gctggttaca tgactgccaa ggggtgctgc tggccacact gcactagcaa gtttgccaga   17160
tggaggacaa gcgatcattg agtatggctc gctgtgaaga aagaaattcg agaggacagg   17220
atcatggctt ggaaagggtg cctttccctc cccagttgca gtcagagacc taccttcacc   17280
cagcagatcc ttcccctgcc tgggacgacc cggggtccac tgggagccct aacttgaggc   17340
tgctgacaga agaaatcgct ttccaacctc tggccgagga agcttcgttc agaaggccgc   17400
accctgacgg tgacgtcccg ccccaggag aagataatct cctctccctc cccttttccac   17460
agaaactgtg gagactggtc agcagcaacc agttttcgtc catctggtgg gatgacagtg   17520
gggcttgtag agtgatcaat caaaaactct ttgaaaagga gattctcaaa agggacgtcg   17580
cacacaaagt gttgccaca acttcgataa agagcttctt ccgccagcta aacttgtatg   17640
gcttccgaaa acgcgtcaa tgcactttca ggaccttcac ccgcattttc tccgcaaaaa   17700
ggctggtctc catcttgaat aaggtaatga acgacaagcc tctggagggg ttaagtcggt   17760
```

-continued

| | |
|---|---|
| gggctctggg gcctggtcgg gtggaagtcc caggactgcc tcctgggaag tgggcgacct | 17820 |
| caggcagggt gtggggccat cgctgtgggc ctgtgtcccc ctctgggtgg aggtgacatg | 17880 |
| aactaagagt gaatgtgggg agagggctga ggatggtgcg ggcccctctc gagtgtgtaa | 17940 |
| aatatcacag gtgccaagta gccgtatctg cgtgtcgtcc tccccgggc cagccatgtc | 18000 |
| atctggtggt tgctgtgtcc ccctgactcc acagcacatt accctgtgag gtgagcaggc | 18060 |
| caggggagtc tggtatttgt accactgtca ccctagctgg tgtctggaga ggtgctcaag | 18120 |
| tggaagcact gaagggcgcc tggcgcagga ggtgcagatg ctcctgctgc ccttggtagg | 18180 |
| tgggcccctg gtgtggaaga gccagtaccc agggcctcca acccagccgg ggtgcattct | 18240 |
| gttgccagct gacactgcat gggggaggcc cagaatcttc ttccctcctg gtctgcaact | 18300 |
| tcaaagaccc tttccgccgg ccatggacac cctaatctgc cattttgagg cttttttccaa | 18360 |
| gacggaaagg cccgccacaa cttggtaaac cttgacgatg tgaacgcgag tccccagctt | 18420 |
| cctttgggga ctgggacctt ttccagaaag gcctcctggg ccagtagagt tctcttgcac | 18480 |
| aggggcgtag atggttggta gttgtagtcc atccttgtga cttg | 18524 |

```
<210> SEQ ID NO 13
<211> LENGTH: 7695
<212> TYPE: DNA
<213> ORGANISM: Homo sapiens

<400> SEQUENCE: 13
```

| | |
|---|---|
| ggcccaggag gccttctctgg aaaaggtccc agtccccaaa ggaagctggg gactcgcgtt | 60 |
| cacatcgtca aggtttacca agttgtggcg ggcctttccg tcttggaaaa agcctcaaaa | 120 |
| tgcagatta gggtgtccat ggccggcgga aagggtcttt gaagttgcag accaggaggg | 180 |
| aagaagattc tgggcctccc ccatgcagtg tcagctggca acagaatgca ccccggctgg | 240 |
| gttggaggcc ctgggtactg gctcttccac accaggggcc cacctaccaa gggcagcagg | 300 |
| agcatctgca cctcctgcgc caggcgccct tcagtgcttc cacttgagca cctctccaga | 360 |
| caccagctag ggtgacagtg gtacaaatac cagactcccc tggcctgctc acctcacagg | 420 |
| gtaatgtgct gtggagtcag ggggacacag caaccaccag atgacatggc tggccccggg | 480 |
| gaggacgaca cgcagatacg gctacttggc acctgtgata ttttacacac tcgagagggg | 540 |
| cccgcaccat cctcagccct ctccccacat tcactcttag ttcatgtcac ctccacccag | 600 |
| aggggggacac aggcccacag cgatggcccc acaccctgcc tgaggtcgcc cacttcccag | 660 |
| gaggcagtcc tgggacttcc acccgaccag gcccagagc ccaccgactt aacccctcca | 720 |
| gaggcttgtc gttcattacc ttattcaaga tggagaccag ccttttttgcg gagaaaatgc | 780 |
| gggtgaaggt cctgaaagtg cattgacgcc gttttcggaa gccatacaag tttagctggc | 840 |
| ggaagaagct ctttatcgaa gttgtggcaa acactttgtg tgcgacgtcc cttttgagaa | 900 |
| tctcctttc aaagagtttt tgattgatca ctctacaagc cccactgtca tcccaccaga | 960 |
| tggacgaaaa ctggttgctg ctgaccagtc tccacagttt ctgtggaaag gggagggaga | 1020 |
| ggagattatc ttctccctgg ggcgggacgt caccgtcagg gtgcggcctt ctgaacgaag | 1080 |
| cttcctcggc cagaggttgg aaagcgattt cttctgtcag cagcctcaag ttagggctcc | 1140 |
| cagtggaccc cgggtcgtcc caggcagggg aaggatctgc tgggtgaagg taggtctctg | 1200 |
| actgcaactg gggagggaaa ggcaccctt ccaagccatg atcctgtcct ctcgaatttc | 1260 |
| tttcttcaca gcgagccata tcaatgatc gcttgtcctc catctggcaa acttgctagt | 1320 |
| gcagtgtggc cagcagcacc ccttggcagt catgtaacca gccccatgac atcataaagg | 1380 |

```
ggctctgact gccgggggt ggcatctcca cccccagcaa gttgtgtaat aaagggccaa    1440
ggcagacaag tagctgccca tctgcatgtg cacattctgg tcctcacagt catttcaatg    1500
ggaaagatga cactagtgca caagagtgcc gaggggccct gccacaccgt agatgcagac    1560
ctggagcggt ccccttgtcc tagagctcct gagccaggca caactacagc aaagccctgg    1620
ctcaggaagg tcagagctca ccgtctgagt catgggccca cagacccag cacatgactg     1680 acactcggaa gcacagaaca aagggtagga cggtgcccat gggtcaggct gtagccacgc    1740 cacccttttcc accctgtcct agccagaggc agcaatgtgc tccatacaga tcctcctaac   1800
acacccacac tgtcggtccc cagcacgcag atgcccgaca gcccttagg caaatggctt     1860 agctgactgc cccaccacac gccgtcgcca tgcagtccag tggggagtcg gaggcagcct    1920
ccttcctgcc tctcctcggc ctgcacgtgt cccccacca gcagagacc cttctacacc      1980 ccgggtgtct gcggtcacat cgcggtgggg catgcagctg ttggccttcg agcatgtttt    2040
gttttccttg gccagtgtct ccagagaaac gcacgtgggg ttgtgtccag cggtccatct    2100
ctgcaacagt tgttcctttg ggattggatg ctaggaggtc acgggagagg tgtccatcca    2160
aagcagtgtc tgtgtcacac actgtcccca cacacagggc cacctctgca cagactcccc    2220
cgactcgatt ctgggcacag agctcagtga ccttccagag actgccacga accggtgatg    2280
cctccacgct tgagacatcc tgaccgcagg gcccaaggcg cactggctca gggggtgaca    2340
gtgaggggtc tgcaaacaga ctgctgatgc tcaacccggc cgctgccgag ctgtgtgact    2400
tgggcacgtc acttaacctc tctcggcctc tgtctcctcc cggggataag agtagtagca    2460
cctgcttccc ggggctgtga ggatccagtg ggacgtatag gaactagcga ggcaccggca    2520
gttgggtcag agctactgtt gtcacttcac aaggcatttt cttcaacagc aagtcggaaa    2580
tctcatgagc ctaaggcaga atccacctgt ggcctctggt tacaacccac aggactgaaa    2640
atccttccag ccacagcaac tggtgaattt cctggtcaat tgccacaagt catgagctga    2700
accccacttg agtttcagtt caggcagaac tctagagacg actagggcaa gctagacagc    2760
gactgcagag ccttttgttg cagcgtgagc agtcctcagc tgttgacatc actggggagc    2820
aaacgaggac caggagcggt gaaaggacag tgtctgctgc agattgtcgt agcacccaag    2880
gaacactcca gaaagcctcc taagcagtaa caagtgtggc aaggtgtagc ccagccaaca    2940
gtggcatctg cgaggcgtcc cctccttcct cccactaccc cgtataccct gggacctgtg    3000
cactgaagga ctcattctaa aggctgtgcc cctgcagccg ccagcctcac tcactggctg    3060
cctgtgccag ctagagattt cttcctctg aggctggctg agaggaccac tccagttccc    3120
tggcccatcc agcaaagaag atacacatca tgcacgtgta aaatgaggaa ccggtttatt    3180
gaacagctta aggagagcaa aaatagtggc tttagctaca tttttacac actgagcagg    3240 aaagtctaaa ccatcccgtt cccctgtacc ccaaagagaa cagggcttgc tggaggccag    3300
tgccaagggc ggagtcgtgc tcgcagcaga cttgaattaa ccccatgtag gccggcgagc    3360
agttgcccgc gtgaaaacac caccctcttc tcctggctga aagatcaaa gctctttttt    3420 tacccctcttt tcagcaaagg acctatttgt tttcaggcag gaggatgtta aacttgcagc    3480
ctctgacaca cggtggaacc tgcagtgctt ggagaaacgg cacgcacacg tgaaaacatc    3540
atgcctactc caaagccttc ttgttgctgg caggagggaa gcttgagact ttcccacgca    3600
tagtcgtgac ccgcgtggcc gtttctgctc tcagcaacat tctctagtgt tccggcttca    3660
agcagcgctt gtcaggtttg aagctagcca ctattctgag aacgtcagaa aagcatggac    3720
catctcttgc ttggtgttgc cgttgtggca gtagcagcta ctacgtacct gcacgagttc    3780
```

```
cagggcagaa gtggcaatgt cccatgaagg cgtggcaccc cacgggggggg gggggggagt    3840 gtgccacggg cgtccacttc tgcagcagaa ggcatgtgcc tacagcacaa gcttgtaaaa    3900
aaatacttga acagaatatg ctgtacagaa ctagggggtta acaccgcata tgaagatgct    3960
aaaacatttg tataaatact ctgtatacaa gcatggagtc actcccgtag aaagggctca    4020
tccgtgaggc tatgaaaaac tgctgtcagc atgcccaaag agaaactact tccacagtag    4080
gaacagaaaa aaggactgtg ctgtgtctaa acacgtggtg catcagagac atagttacag    4140
ttcctactga ctgccccagc cacgacctgg gagtgctgag gacctgggag tgctcagcga    4200
gctgcaggag gtcagccctg tggagaaata catttctaaa caatactttt gattgggatt    4260
tcagcaccgt atagacagat gttccttctg ggggcctggc aagcagccat ctcccagtgg    4320
gtctgacggg gaagaggggt acctggagcc cctcccagac agacggtaat cccaccccctg    4380 ttctcacact cttcctggca tccgcatctg ctggcacaca cccccgtcac ctgccacttc    4440
cgcgtcccgt cgtggtgagt ggctgatagg cgctggatgc aaacaaggca tgagatggac    4500
gtacctggag acccagctcc agtactggtt ctggtctgcg gggtgaacga ggggggcagag   4560 gaaggcggag agagtgcgtc ccagtccact taagctctgt ccccggaagt ggcatctaat    4620
ctggcatttc gatatttaat ttgggaggtg ggagcacata cttcccaggg ctctgggtaa    4680
tgaccaccct ggccttcttt cgaaacatgg gtgcgatttt aggggggctcc ggaactgggg   4740 tctcttcggt ttcttcatta tcttcgtgat ggagatcata ggaaatgttt ccatattctc    4800
gtagaaatgg gaagatttca agcagaaact gacagaaatc tttgcggata ccaaaccacc    4860
ctgaaaaata agaattttttt atttcacaca cgaggctcaa ctgaccttcc tgttaacttt   4920
ctttccgtaa caagaagttt cactcctaca atgtcataac atactttatc cagactcctg    4980
agtcacaaag cctgaacagg gcttgagtac ccaaaatggg gaagaagtgc aaatgctagc    5040
tctgtggtgc ttggagtggg gttcccggac cggcagggac agcgtccacg gggcctagtt    5100
agggatgcca ttctcgggcc ccagcccaga cctccagaaa ctgagtcggg ctagggtggg    5160
ctccagcggt cccctttttcc tggccctttt gggattctgc tggatgccca aatttgagaa    5220
ctactgctcc agtgagtctc aaaatatctg tggtgcgcag actacggtgt cttccgctaa    5280
tcttctccag ccaggataaa ctcatggatg acagtgccac ccaagaacaa gatttctgtc    5340
accctctgga atccgtgagg gcggtagtca tgcacgggtt ggccaggagg gggcctgaac    5400
tcatggagcc accttaaagc cactttccca gtcccactac tcctctctgt aggctactgg    5460
agtgtcagct cggtgcaagc cctccctgct cccgggtgcg gggtagggggg cagaggcaca   5520 aacagcaagc acagcccggg ctgctgggct gcagtgaggc cctgccccca aacccactgg    5580
ctttccgaag ggcaatgctc tgggcttccg tgccatggag cccacagcct tgccaggaag    5640
gcaccctctg cagagatcgt tttggaagtg tctgcctcag caagcaggtg gaggggaata    5700
gagtgttagc aaggcaagac aggcaagact cgggtgatgg cagcaaggat atgggggagg    5760
cagagcggcc aacagggacc taggatgaat cccaggtttg ggtgggagat gtggatttttc   5820 catcaaaccc tccgggcct gggaagaatc tgtcttgatc cccatttttgc agaggaggga    5880 acgggatctc tgagaggttg cctgccgtgt ctggttctac ctcaaatggc agcgtgcact    5940
gcgagaaaag tccggtgca ggccagcaga acaccagagt tacggcatgc ccttccctta    6000
gaaggtccca gaatttcctc agccctcact ttcccacaca agcttctaaa ttggggccct    6060
cggggactca tcccttccta gacttctatc cgccacccccc caccccctgg tccccccca    6120 gacacacacc aaggacttct gaaatgctga gtacatacag tggtttcctc ccttctgtcc    6180
```

-continued

| | |
|---|---|
| aaatgtggtt gccatcagcg tgatcaacga gagccaaagg gggacaaaga tcgggatgca | 6240 |
| ggagaaggcg ttgtggccat ccagtttgtg aaccagcaga atctaaagaa agagacatag | 6300 |
| tcccggttga tgccagcacc gaaaatgggc agaggcggaa gccagacttc attaggcagt | 6360 |
| tcctccccac caccccaccc ccgcgtgagc tcccacaaga gggaacatca gcaccgccag | 6420 |
| aaaaaggcag gaaaccacct atccctgggg aaagctcgaa atgagctttt atgtccctct | 6480 |
| tcagagctcg gcaatagcct atccacttga aaagttccca gtgccagcag ttttatggca | 6540 |
| aactcctccg ggtgtttgtt ctaaggagtc aacagctccc attctagaat tctccacgtg | 6600 |
| actccaatac acaaatctga catcccactc tgctttcccc agagtggaaa ctggagccat | 6660 |
| acagaggcac catggctaaa aaggtgcact cttctccctg ccagcccac gtgctgcccc | 6720 |
| caagagaaag gaaggatgct ctcctttcac cgaagctccc tctcggagat ggctgtgttc | 6780 |
| tctcccctct cctggagtgg gctcactgtg agctcgaggg acagaggctg cctttctagg | 6840 |
| ggtgcagaat cctgtcaggg gaagcgcaag cttcaggggc tgaagaggct tcccgtggaa | 6900 |
| cgcttacctc aaatgtaaga aggggcacga cgatggtcat ccagctcagg gccatggtta | 6960 |
| tgtgtgtcct gcgctgtccg caatcacatc catagagcgc aagaacaaga cggaccacac | 7020 |
| aatgtagtag aggaccacca ggcacagaaa ggacatgaga atccacagcg ggacacacac | 7080 |
| aacctggggg tgggtgagag aacagcaaga gaagtctctt tagagcttcc aacctggcct | 7140 |
| ctgatggaag gcatctttag caccttgctg tgtctgtcca gttaaggcgg tccttcctgt | 7200 |
| gagccgaata aggaccgttc catctcccag gactgctggg agcatcgctc aggacagaaa | 7260 |
| aggtatggta tgttcactat ggggcctgct gccaccaggg gacacacacg ctcagtgagt | 7320 |
| catcagtccc tcttcctttg ggtgacagac agccctgcac ctggctccgc agcctctact | 7380 |
| cttccagagg cccactctcc cacactctct caggctcctc taggttctgc tgccatcaca | 7440 |
| gcttcccggg aaatgggaca caactgtcac cctgtgcaca cacacaagat ctcaccccaa | 7500 |
| cagactctct tcacaggcaa cattcccaca acctgctggg ggtactttgg caacacaaat | 7560 |
| gggaatgggc tccccagaaa gtctggctgc ctgggctcct aaggatccct aacctcaccc | 7620 |
| ctaccaagtt agtgaacttg gcgggttgat gctggataca ggttgatgct ggatacgtag | 7680 |
| cgctgccggg tgacc | 7695 |

<210> SEQ ID NO 14
<211> LENGTH: 9014
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 14

| | |
|---|---|
| gggcgaattg ggcccgacgt cgcatgctcc cggccgccat ggcggccgcg ggaattcgat | 60 |
| atcactagtg aattcgcggc cggcgattgg gcccgacgtc gcatgctccc ggccgccatg | 120 |
| gcggccgcgg gaattcgatt ccttaattaa gtcgactggg acccaaactt tggagtcgtt | 180 |
| gacagatgtg acaggtgaag cctgggatga catcgccaaa aatgcaacgt ctcactcatt | 240 |
| gtcactactc ccagggctca gtcgtcactg gggaaaatct ccagaaggta gcgcgggcca | 300 |
| aggtgacagg tgtctgccaa gatctgcccg ccagactccc gggcggcgcg ctccctccct | 360 |
| gcaggccttc agcccgtcag catccccttc ctcgggggcc tgctcactcc agcctccat | 420 |
| cccctgccca tctcctccgc cggtcgcgtg cggacacaag gatggggacc tcccagcgag | 480 |

-continued

```
gagcgctctg ggcggggctc cggacgcatg cgcggccctc gtacggaagc ccggaaggag    540 gggcagggggg cggtggctca ggtttctccg ggcggcggcg gcggcggcgg cggcgacggc   600
gacggcgacg gcagcgggga cggcagcagt agcgggagca gcagcgtgga cgcggctggc   660
gctggcgcca tgaacccgct gtaaggcgca ggctgtgcag cacggggtgc gggggaggag   720
gaggaggacg ccgcggtgaa gttctccgcc atgaacctga ggggcctctt ccaggacttc   780
aacccgaggt gaggcggcgt cgttggcgcc cccgggagtc cgccgctgcgg gctcgggcgc   840 gggctggtgt tcggctccgg ggaggcacgg cgggcgagat gctgcagccc gaggacccgg   900
gcgcctgccc gagcctccct gcgggtgcaa gcggtcccca ggcaaaacag tcggcctcgg   960
cgcccgcccg cttcctcctc ccgtgcccgg tgctttcagc ccctgcccgg ccacggccgg  1020
aagggcccgg ccgcgagccc cgtcctgccc caagggaacc ccattctttt ctgcttgctg  1080
tccctcattg gtgtcccaac ttcttcgtct cggttccatc ctcttctgcg ccgctgcggg  1140
ccctccattc tccgcgtcag ggccgtctca ctcgacccaa caccctacc cccacccag  1200 ctgtttcctc cagttcctcg cagtccttgg ggttttcctt gggtttatgc ccatccctct  1260
cttgtttgct tctttgttga acggatacct gaaacactgt tgaatccttg gagtcagtgt  1320
cggggtatgg caataccttta tataatgcat ttctgggtga gcctgatcat tttccatact  1380
cattttctca tcagtcttca ctacaagttt atttgcagga agtagatatt gctgtccttc  1440
ttttccagat ggggaacacc cagtggacag tgtggagaaa acactggcta agcactcaag  1500
cgcctgtcct tgcacttgcc cgactgtttt gtaactgttc tttaccccag gctgtgagct  1560
ccctgaagct gagaccatct cctgctcatc tcagtgtccc cagcgcctcc cacccaccgt  1620
atctggcaca tagtaggcac atataaaatg tttgtggaac taaactgagc ccaaagactt  1680
ggattggaga cgaggccata tgtaactggg tgattctctg cccttctttg gcccttctgt  1740
aaaatgagga gttggcctaa ctgatctctt aaatgcacta ctctccgaaa ggagtatccg  1800
tttcccttat ttgccagttg ggaagacgtg ctcagtaaat atttgtgtgc tgtaacctat  1860
gttaggtgct ttagatgctg gcggtctcag catggggtga agaagggctt gtacacttaa  1920
gatgccttac agtactgtgc agtgctgtac tgcgggggcc aactctgggg acctatgcct  1980
tggctgcttg ttgaggatga aaggaagttt taggggagta tttgtatgtt gagggtgcag  2040
tctccctagg gatggtgaca tttaacttg tgagtcattg tgactttgta tgtgcccta  2100 ttccactttg agttcatgtt ctggttagga gtgccagtgt ctctaacacg gtgcagacat  2160
tatcattgtt ggcttcgaag gcatagagga ggtaacagaa ctaactgcag tcccttcctc  2220
tgctgcatca gggggttaag attggtctgc agggtagtag ggttggtgct gtggctggac  2280
aagccctgta tgtcttctat ttggagatgg tgataagaaa gttaagtaaa aactgaattg  2340
ttttgtgccc ttgggcaact cacttatcta ttgttttatc tgtagaatga gtataatctc  2400 tcagtgggggt agggaggcca attaaggatt gattacaaag tgccttacaa atagaaagct  2460
acagtgactt gtttgcaagg tgacagagaa ttcagaagcc tcaagaaact gccttaagtg  2520
atcaaacagg ctaacggagt tgccaaagca aaatagtgct gcactgatac tacctttaac  2580
cgttttttcc tttagccctt ttccccccaa aaaattagt atatgaaatt acagtgaaat  2640
acctggtatc taagcagatt tatagtaatt ctcaacatat tcatcaatct cttaattcta  2700
cctgcattaa aatgtatttc tacctgaaaa gtttaaaggt cttttatact gtgccatttt  2760
cctgattcat tgttgccaga ggtagtgagt tccttaattt tacagatatt tcaagaggac  2820
attggccagg tattattggt aaatcagatt tgtttttta gctggtagtg tttcacctct  2880
```

```
cctgagcact cctagttttt gacagtgtgc tttagtctcc ttccatgctg aggaaggcct   2940
tctctatagg agaaagaaaa ctgaggggtg tacacaggaa gttaccttat gctgggggact  3000 caaaccttga tgctactgct ttgctccctg cctctatttt tgaaccaatt caacatctcc   3060
ctcctacccc aggaccttgt cacacactgt tctctttacc aggaatgttt ccctctcttt   3120
tcctctcctc cagacctagt gaactccttat ttatcctcac ttggcacttg ctaagggaag  3180
cattcctgac ttccctgacc agatttactg ctccctgttt ctacagttcc tgtagtattt   3240
actactcctc catcatagtg catatttgta cccttgtgtc tgtctggatg cttatttgat   3300
taatacctgc ctcccccact aaactttaag ctccatgggg tcaaggccgt gactgtgtca   3360
gtatcgtagc ctgcatactt ggaatagtac ctggctcaat aaatatttgt ggagtaaata   3420
actgaataac tctccagagc ctataagata aatctagagc tgctgctttc aatcactgct   3480
ttcctggtgg tctgtggcct ggttctcttt cttctcacac tcttcccacc ttcagagtgc   3540
agccattgct ttggagagat gggagagaac atggcactaa ggcagaatat ggctatattt   3600
actttgaaga gcatgtcttt gtcatagaaa tagtcactgt catggtttgg tgggtcccaa   3660
ggcatgggtc atggctccag atcccctttc cagccttttg gatcttggta agtctgaacc   3720
cactgctgcg ttggcaaggc tctggaaact atagtgacag agaatgattc acaagtgtca   3780
acactcagat gtacagggct gccagctgac ccactctacc tatttccatc tggcactgaa   3840
ctggttgatc atgaacttct tttcataatt gcttttagt tatgcaggtt aagacatgcc    3900
gaaacagatg taccggaccc acaaacaagt ccttccttga atgcctgagg cttcctaaca   3960
gtgaaagagc cctgttctta gagtaggcaa actgattctg aggcattgta ggtggtaggg   4020
atctggtagt aggtagcatt aggtgggctc ccggcactca ccatggagcc ttgaaatttt   4080
ctgctacttt gggggagttg ctggttcaga gaaggcccct ccaccctggt agccatgtgg   4140
cactggaagg ctgtgaaaac tctgctgggc cttcttagtc atctgttgtg agctcctgat   4200
gggagtgtgg tgtatccctc aggtgtgcta gactggaaca aaggctgaga agtgttgctc   4260
tgggggttcc aacttgtggg catggggtac tgatgagatc agtagtgttt ggagacttct   4320
gtatgctcca tcttcagaag acattctgga gtccatataa gttatcttgt ctcttgtttg   4380
aagcaggaaa aaggaatgcg attgctggta atatagttca ctaaagtcag ctacctggcc   4440
tctaacagtt atttgcaaag tatattataa cattgattcc tcaaacatct agattcctat   4500
ctcgtgccaa gtgatgtact aggtgctcta agtacaaaaa taaggaata tagtcctcct    4560 ctcaatgcgt aagcctagtg gaagaagcag aaatgaaagg gaataagaa ttcaatagag    4620 tatgaggcat tacagtgaaa gaaaccaaat gtcttagaag tacaaatggc agagctacta   4680
attctgtctc gagcaggcag ggaagagtct atagtggaaa tgactttga gctagatttt    4740 gaattgagct agtcttttga gccagacttt tgagctagaa ttgtagggtt gtcatcagac   4800
cagagagtag gaagggtacc ttgtgaggaa gagagagaga gatcagattg ttactgtgtc   4860
tatgtagaaa aggaagacat aagaaactcc attttgatct gtactaagaa aaattgtttc   4920
tgctttgaga tgctgttaac ctgtaacttt agtcccaacc ctgtgctcac agaaacctgt   4980
gctgtaatga atcaaggttt aatggattta gggctgtgca ggatgtacct tgttaacaat   5040
atgtttgcag gcagtatgct tggtaaaagt catcgccatt ctccattctc gattaaccag   5100
ggacacagtg cactgcggaa ggccgcaggg acatctgccc aagaaagcct gggtattgtc   5160
caaggtttcc ccccactgag acagcctgag atatggcctt gtgggaaagg aaagacctta   5220
ccacccccca gcccgacacc cgtaaagtgt ctgtgctgag gaggagtagt gaaagagcgg   5280
```

```
ggcctctttg cagttgagat aagaggaagg cttctgtctc ctgctcatcc ctgggaatgg    5340
aatgtctctg tgtaaagctg accattccca ttcgttctat tctgagatag gagaaaacca    5400
ccctgtggct ggaggcgaag tatgctggca gcaatactgc tctgttactc tttgctacac    5460
tgagttgttt gggtaaagag aaacataaat ctagcctgcg tgcacatcca ggcacagtac    5520
ctttccttga acttattcat gatacagatt cctttgctca cgtttccctg ctgaccttct    5580
ccccacctgt tgccctgcta cactcccctc gctaagatag taaaaataat gatcagtaaa    5640
tactgaggta actcagaggc tagcgctggt gcgggtcctc cgtatgctga gtgccggtcc    5700
cctgggccca ctgttctttc tctatacttt gtttctgtgt cttatttctt ttctcagtct    5760
cgtcccacct gacgagaaat acccacaggt gtgggggggc tggcccctt cagtatctca     5820 gaagggacaa agtacacaaa ggcatggggt catgatagtg cctggtatgt tcaggtagtg    5880
aagaggtcca tgtggtatga gcactgcaga tgatatgtgt cgtatgaatt aaaaatacat    5940
agttactgca aatagttttt acaggttatt gttttttaaga aagcagtatc taatgcacga    6000
gtgtactgtc agtactgtca atgaactact taccactcaa gtgactgctt acgcgtcgaa    6060
tcactagtga attcgcggcc gcctgcaggt cgaccatatg ggagagctcc caacgcgttg    6120
gatgcatagc ttgagtattc tatagtgtca cctaaatagc ttggcgtaat catggtcata    6180
gctgtttcct gtgtgaaatt gttatccgct cacaattcca cacaacatac gagccggaag    6240
cataaagtgt aaagcctggg gtgcctaatg agtgagctaa ctcacattaa ttgcgttgcg    6300
ctcactgccc gctttccagt cgggaaacct gtcgtgccag ctgcattaat gaatcggcca    6360
acgcgcgggg agaggcggtt tgcgtattgg gcgctcttcc gcttcctcgc tcactgactc    6420
gctgcgctcg tcgttcggc tgcggcgagc ggtatcagct cactcaaagg cggtaatacg     6480
gttatccaca gaatcagggg ataacgcagg aaagaacatg tgagcaaaag gccagcaaaa    6540
ggccaggaac cgtaaaaagg ccgcgttgct ggcgtttttc cataggctcc gcccccctga    6600
cgagcatcac aaaaatcgac gctcaagtca gaggtggcga aacccgacag gactataaag    6660
ataccaggcg tttccccctg gaagctccct cgtgcgctct cctgttccga ccctgccgct    6720
taccggatac ctgtccgcct ttctcccttc gggaagcgtg gcgctttctc atagctcacg    6780
ctgtaggtat ctcagttcgg tgtaggtcgt tcgctccaag ctgggctgtg tgcacgaacc    6840
ccccgttcag cccgaccgct cgccttatc cggtaactat cgtcttgagt ccaacccggt     6900
aagacacgac ttatcgccac tggcagcagc cactggtaac aggattagca gagcgaggta    6960
tgtaggcggt gctacagagt tcttgaagtg gtggcctaac tacggctaca ctagaagaac    7020
agtatttggt atctgcgctc tgctgaagcc agttaccttc ggaaaaagag ttggtagctc    7080
ttgatccggc aaacaaacca ccgctggtag cggtggtttt tttgtttgca agcagcagat    7140
tacgcgcaga aaaaaggat ctcaagaaga tcctttgatc ttttctacgg ggtctgacgc      7200
tcagtggaac gaaaactcac gttaagggat tttggtcatg agattatcaa aaaggatctt    7260
cacctagatc cttttaaatt aaaaatgaag ttttaaatca atctaaagta tatatgagta    7320
aacttggtct gacagttacc aatgcttaat cagtgaggca cctatctcag cgatctgtct    7380
atttcgttca tccatagttg cctgactccc cgtcgtgtag ataactacga tacgggaggg    7440
cttaccatct ggccccagtg ctgcaatgat accgcgagac ccacgctcac cggctccaga    7500
tttatcagca ataaccagc cagccggaag ggccgagcgc agaagtggtc ctgcaacttt      7560
atccgcctcc atccagtcta ttaattgttg ccgggaagct agagtaagta gttcgccagt    7620
taatagtttg cgcaacgttg ttgccattgc tacaggcatc gtggtgtcac gctcgtcgtt    7680
```

-continued

```
tggtatggct tcattcagct ccggttccca acgatcaagg cgagttacat gatccccat      7740
gttgtgcaaa aaagcggtta gctccttcgg tcctccgatc gttgtcagaa gtaagttggc      7800
cgcagtgtta tcactcatgg ttatggcagc actgcataat tctcttactg tcatgccatc      7860
cgtaagatgc ttttctgtga ctggtgagta ctcaaccaag tcattctgag aatagtgtat      7920
gcggcgaccg agttgctctt gcccggcgtc aataccggga aataccgcgc cacatagcag      7980
aactttaaaa gtgctcatca ttggaaaacg ttcttcgggg cgaaaactct caaggatctt      8040
accgctgttg agatccagtt cgatgtaacc cactcgtgca cccaactgat cttcagcatc      8100
ttttactttc accagcgttt ctgggtgagc aaaaacagga aggcaaaatg ccgcaaaaaa      8160
gggaataagg gcgacacgga aatgttgaat actcatactc ttccttttc aatattattg      8220
aagcatttat cagggttatt gtctcatgag cggatacata tttgaatgta tttagaaaaa      8280
taaacaaata ggggttccgc gcacatttcc ccgaaaagtg ccacctgatg cggtgtgaaa      8340
taccgcacag atgcgtaagg agaaaatacc gcatcaggaa attgtaagcg ttaatatttt      8400
gttaaaattc gcgttaaatt tttgttaaat cagctcattt tttaaccaat aggccgaaat      8460
cggcaaaatc ccttataaat caaaagaata accgagata gggttgagtg ttgttccagt      8520
ttggaacaag agtccactat taagaacgt ggactccaac gtcaaagggc gaaaaaccgt      8580
ctatcagggc gatggcccac tacgtgaacc atcacctaa tcaagttttt tggggtcgag      8640
gtgccgtaaa gcactaaatc ggaaccctaa agggagcccc cgatttagag cttgacgggg      8700
aaagccggcg aacgtggcga aaaggaagg gaagaaagcg aaaggagcgg gcgctagggc      8760
gctggcaagt gtagcggtca cgctgcgcgt aaccaccaca cccgccgcgc ttaatgcgcc      8820
gctacagggc gcgtccattc gccattcagg ctgcgcaact gttgggaagg gcgatcggtg      8880
cgggcctctt cgctattacg ccagctggcg aaagggggat gtgctgcaag gcgattaagt      8940
tgggtaacgc cagggttttc ccagtcacga cgttgtaaaa cgacggccag tgaattgtaa      9000
tacgactcac tata                                                        9014
```

<210> SEQ ID NO 15
<211> LENGTH: 5954
<212> TYPE: DNA
<213> ORGANISM: Homo sapiens

<400> SEQUENCE: 15

```
ggccgcggga attcgattcc ttaattaagt cgactgggac ccaaactttg gagtcgttga       60
cagatgtgac aggtgaagcc tgggatgaca tcgccaaaaa tgcaacgtct cactcattgt      120
cactactccc agggctcagt cgtcactggg gaaaatctcc agaaggtagc gcgggccaag      180
gtgacaggtg tctgccaaga tctgcccgcc agactcccgg gcggcgcgct ccctccctgc      240
aggccttcag cccgtcagca tcccccttcct cggggccctg ctcactccca gcctccatcc      300
ccctgccatc tcctccgccg gtcgcgtgcg gacacaagga tggggacctc ccagcgagga      360
gcgctctggg cggggctccg gacgcatgcg cggccctcgt acggaagccc ggaaggaggg      420
gcaggggggcg gtggctcagg tttctccggg cggcggcggc ggcggcggcg gcgacggcga      480
cggcgacggc agcggggacg gcagcagtag cgggagcagc agcgtggacg cggctggcgc      540
tggcgccatg aacccgctgt aaggcgcagg ctgtgcagca cggggtgcgg gggaggagga      600
ggaggacgcc gcggtgaagt tctccgccat gaacctgagg ggcctcttcc aggacttcaa      660
cccgaggtga ggcggcgtcg ttggcgcccc cgggagtccg cgctgcgggc tcggcgcgcg      720
gctggtgttc ggctccgggg aggcacggcg ggcgagatgc tgcagcccga ggacccgggc      780
```

```
gcctgcccga gcctccctgc gggtgcaagc ggtccccagg caaaacagtc ggcctcggcg    840
cccgcccgct tcctcctccc gtgcccggtg ctttcagccc ctgccggcc acggccggaa    900
gggcccggcc gcgagcccg tcctgcccca agggaaccc attcttttct gcttgctgtc    960
cctcattggt gtcccaactt cttcgtctcg gttccatcct cttctgcgcc gctgcgggcc   1020
ctccattctc cgcgtcaggg ccgtctcact cgacccaaca cccctacccc caccccagct   1080
gtttcctcca gttcctcgca gtccttgggg ttttccttgg gttatgccc atccctctct    1140
tgtttgcttc tttgttgaac ggatacctga aacactgttg aatccttgga gtcagtgtcg   1200
gggtatggca ataccttata taatgcattt ctgggtgagc ctgatcattt ccatactca    1260
tttctcatc agtcttcact acaagtttat ttgcaggaag tagatattgc tgtccttctt   1320
ttccagatgg ggaacaccca gtggacagtg tggagaaaac actggctaag cactcaagcg   1380
cctgtccttg cacttgcccg actgttttgt aactgttctt taccccaggc tgtgagctcc   1440
ctgaagctga gaccatctcc tgctcatctc agtgtcccca gcgcctccca cccaccgtat   1500
ctggcacata gtaggcacat ataaaatgtt tgtggaacta aactgagccc aaagacttgg   1560
attggagacg aggccatatg taactgggtg attctctgcc cttctttggc ccttctgtaa   1620
aatgaggagt tggcctaact gatctcttaa atgcactact ctccgaaagg agtatccgtt   1680
tcccttattt gccagttggg aagacgtgct cagtaaatat ttgtgtgctg taacctatgt   1740
taggtgcttt agatgctggc ggtctcagca tggggtgaag aagggcttgt acacttaaga   1800
tgccttacag tactgtgcag tgctgtactg cggggggccaa ctctggggac ctatgccttg   1860
gctgcttgtt gaggatgaaa ggaagttta ggggagtatt tgtatgttga gggtgcagtc   1920
tccctaggga tggtgacatt ttaacttgtg agtcattgtg actttgtatg tgcccttatt   1980
ccactttgag ttcatgttct ggttaggagt gccagtgtct ctaacacggt gcagacatta   2040
tcattgttgg cttcgaaggc atagaggagg taacagaact aactgcagtc ccttcctctg   2100
ctgcatcagg gggttaagat tggtctgcag ggtagtaggg ttggtgctgt ggctggacaa   2160
gccctgtatg tcttctattt ggagatggtg ataagaaagt taagtaaaaa ctgaattgtt   2220
ttgtgccctt gggcaactca cttatctatt gttttatctg tagaatgagt ataatctctc   2280
agtggggtag ggaggccaat taaggattga ttacaaagtg ccttacaaat agaaagctac   2340
agtgacttgt ttgcaaggtg acagagaatt cagaagcctc aagaaactgc cttaagtgat   2400
caaacaggct aacggagttg ccaaagcaaa atagtgctgc actgatacta cctttaaccg   2460
tttttttcctt tagccctttt ccccccaaaa aaattagtat atgaaattac agtgaaatac   2520
ctggtatcta agcagattta tagtaattct caacatattc atcaatctct taattctacc   2580
tgcattaaaa tgtatttcta cctgaaaagt ttaaaggtct tttatactgt gccattttcc   2640
tgattcattg ttgccagagg tagtgagttc cttaattta cagatatttc aagaggacat   2700
tggccaggta ttattggtaa atcagatttg ttttttttagc tggtagtgtt tcacctctcc   2760
tgagcactcc tagttttga cagtgtgctt tagtctcctt ccatgctgag gaaggccttc   2820
tctataggag aaagaaaact gaggggtgta cacaggaagt tacctttatgc tgggactca   2880
aaccttgatg ctactgcttt gctccctgcc tctattttg aaccaattca acatctccct   2940
cctaccccag gaccttgtca cacactgttc tctttaccag gaatgtttcc ctctcttttc   3000
ctctcctcca gaccctagtga actcctattt atcctcactt ggcacttgct aagggaagca   3060
ttcctgactt ccctgaccag atttactgct ccctgtttct acagttcctg tagtatttac   3120
tactcctcca tcatagtgca tatttgtacc cttgtgtctg tctggatgct tatttgatta   3180
```

```
atacctgcct cccccactaa actttaagct ccatggggtc aaggccgtga ctgtgtcagt    3240
atcgtagcct gcatacttgg aatagtacct ggctcaataa atatttgtgg agtaaataac    3300
tgaataactc tccagagcct ataagataaa tctagagctg ctgctttcaa tcactgcttt    3360
cctggtggtc tgtggcctgg ttctctttct tctcacactc ttcccacctt cagagtgcag    3420
ccattgcttt ggagagatgg gagagaacat ggcactaagg cagaatatgg ctatatttac    3480
tttgaagagc atgtctttgt catagaaata gtcactgtca tggtttggtg ggtcccaagg    3540
catgggtcat ggctccagat cccctttcca gccttttgga tcttggtaag tctgaaccca    3600
ctgctgcgtt ggcaaggctc tgaaaactat agtgacagaa atgattcac aagtgtcaac    3660 actcagatgt acagggctgc cagctgaccc actctaccta tttccatctg cactgaact    3720 ggttgatcat gaacttcttt tcataattgc ttttagtta tgcaggttaa acatgccga    3780 aacagatgta ccggacccac aaacaagtcc ttccttgaat gcctgaggct tcctaacagt    3840
gaaagagccc tgttcttaga gtaggcaaac tgattctgag gcattgtagg tggtagggat    3900
ctggtagtag gtagcattag gtgggctccc ggcactcacc atggagcctt gaaattttct    3960
gctactttgg gggagttgct ggttcagaga aggcccttcc accctggtag ccatgtggca    4020
ctggaaggct gtgaaaactc tgctgggcct tcttagtcat ctgttgtgag ctcctgatgg    4080
gagtgtggtg tatccctcag gtgtgctaga ctggaacaaa ggctgagaag tgttgctctg    4140
ggggttccaa cttgtgggca tggggtactg atgagatcag tagtgtttgg agacttctgt    4200
atgctccatc ttcagaagac attctggagt ccatataagt tatcttgtct cttgtttgaa    4260
gcaggaaaaa ggaatgcgat tgctggtaat atagttcact aaagtcagct acctggcctc    4320
taacagttat ttgcaaagta tattataaca ttgattcctc aaacatctag attcctatct    4380
cgtgccaagt gatgtactag gtgctctaag tacaaaaata aaggaatata gtcctcctct    4440
caatgcgtaa gcctagtgga agaagcagaa atgaaaggga aataagaatt caatagagta    4500
tgaggcatta cagtgaaaga aaccaaatgt cttagaagta caaatggcag agctactaat    4560
tctgtctcga gcaggcaggg aagagtctat agtggaaatg acttttgagc tagattttga    4620
attgagctag tcttttgagc cagactttg agctagaatt gtagggttgt catcagacca    4680
gagagtagga agggtacctt gtgaggaaga gagagagaga tcagattgtt actgtgtcta    4740
tgtagaaaag gaagacataa gaaactccat tttgatctgt actaagaaaa attgtttctg    4800
ctttgagatg ctgttaacct gtaactttag tcccaaccct gtgctcacag aaacctgtgc    4860
tgtaatgaat caaggtttaa tggatttagg gctgtgcagg atgtaccttg ttaacaatat    4920
gtttgcaggc agtatgcttg gtaaaagtca tcgccattct ccattctcga ttaaccaggg    4980
acacagtgca ctgcggaagg ccgcagggac atctgcccaa gaaagcctgg gtattgtcca    5040
aggtttcccc ccactgagac agcctgagat atggccttgt gggaaaggaa agaccttacc    5100
accccccagc ccgacacccg taaagtgtct gtgctgagga ggagtagtga aagagcgggg    5160
cctctttgca gttgagataa gaggaaggct tctgtctcct gctcatccct gggaatggaa    5220
tgtctctgtg taaagctgac cattcccatt cgttctattc tgagatagga gaaaccacc    5280 ctgtggctgg aggcgaagta tgctggcagc aatactgctc tgttactctt gctacactg    5340 agttgtttgg gtaaagagaa acataaatct agcctgcgtg cacatccagg cacagtacct    5400
ttccttgaac ttattcatga tacagattcc tttgctcacg tttccctgct gaccttctcc    5460
ccacctgttg ccctgctaca ctcccctcgc taagatagta aaaataatga tcagtaaata    5520
ctgaggtaac tcagaggcta gcgctggtgc gggtcctccg tatgctgagt gccggtcccc    5580
```

```
tgggcccact gttctttctc tatactttgt ttctgtgtct tatttctttt ctcagtctcg    5640
tcccacctga cgagaaatac ccacaggtgt ggaggggctg gccccttca gtatctcaga     5700 agggacaaag tacacaaagg catggggtca tgatagtgcc tggtatgttc aggtagtgaa    5760
gaggtccatg tggtatgagc actgcagatg atatgtgtcg tatgaattaa aaatacatag   5820
ttactgcaaa tagttttac aggttattgt ttttaagaaa gcagtatcta atgcacgagt    5880
gtactgtcag tactgtcaat gaactactta ccactcaagt gactgcttac gcgtcgaatc   5940
actagtgaat tcgc                                                      5954
```

<210> SEQ ID NO 16
<211> LENGTH: 30756
<212> TYPE: DNA
<213> ORGANISM: Homo sapiens
<220> FEATURE:
<221> NAME/KEY: modified_base
<222> LOCATION: (5934)
<223> OTHER INFORMATION: a, c, g, t, unknown or other

<400> SEQUENCE: 16

```
gtacggaagc ccggaaggag gggcagggg cggtggctca ggtttctccg ggcggcggcg     60
gcggcggcgg cggcgacggc gacggcgacg gcagcgggga cggcagcagt agcgggagca   120
gcagcgtgga cgcggctggc gctggcgcca tgaacccgct gtaaggcgca ggctgtgcag   180
cacggggtgc gggggaggag gaggaggacg ccgcggtgaa gttctccgcc atgaacctga   240
ggggcctctt ccaggacttc aacccgaggt gaggcggcgt cgttggcgcc cccgggagtc   300
cgcgctgcgg gctcgggcgc gggctggtgt tcggctccgg ggaggcacgg cgggcgagat   360
gctgcagccc gaggacccgg gcgcctgccc gagcctccct gcgggtgcaa gcggtcccca   420
ggcaaaacag tcggcctcgg cgcccgcccg cttcctcctc ccgtgccgg tgctttcagc    480 ccctgcccgg ccacgccgg aagggcccgg ccgcgagccc cgtcctgccc caagggaacc    540
ccattctttt ctgcttgctg tccctcattg gtgtcccaac ttcttcgtct cggttccatc    600
ctcttctgcg ccgctgcggg ccctccattc tccgcgtcag ggccgtctca ctcgacccaa    660 caccccctacc cccaccccag ctgtttcctc cagttcctcg cagtccttgg ggttttcctt    720
gggtttatgc ccatccctct cttgtttgct tctttgttga acggatacct gaaacactgt    780
tgaatccttg gagtcagtgt cggggtatgg caatacctta tataatgcat ttctgggtga    840
gcctgatcat tttccatact cattttctca tcagtcttca ctacaagttt atttgcagga    900
agtagatatt gctgtccttc tttccagat ggggaacacc cagtggacag tgtggagaaa     960
acactggcta agcactcaag cgcctgtcct tgcacttgcc cgactgtttt gtaactgttc   1020
tttaccccag gctgtgagct ccctgaagct gagaccatct cctgctcatc tcagtgtccc   1080
cagcgcctcc cacccaccgt atctggcaca tagtaggcac atataaaatg tttgtggaac   1140
taaactgagc ccaaagactt ggattggaga cgaggccata tgtaactggg tgattctctg   1200
cccttctttg gcccttctgt aaaatgagga gttggcctaa ctgatctctt aaatgcacta   1260
ctctccgaaa ggagtatccg tttcccttat ttgccagttg ggaagacgtg ctcagtaaat   1320
atttgtgtgc tgtaacctat gttaggtgct ttagatgctg gcggtctcag catggggtga   1380
agaagggctt gtacacttaa gatgcctac agtactgtgc agtgctgtac tgcgggggcc    1440
aactctgggg acctatgcct tggctgcttg ttgaggatga aggaagttt taggggagta    1500 tttgtatgtt gagggtgcag tctccctagg gatggtgaca ttttaacttg tgagtcattg   1560
tgactttgta tgtgcccctta ttccactttg agttcatgtt ctggttagga gtgccagtgt  1620
```

```
ctctaacacg gtgcagacat tatcattgtt ggcttcgaag gcatagagga ggtaacagaa    1680
ctaactgcag tcccttcctc tgctgcatca gggggttaag attggtctgc agggtagtag    1740
ggttggtgct gtggctggac aagccctgta tgtcttctat ttggagatgg tgataagaaa    1800
gttaagtaaa aactgaattg ttttgtgccc ttgggcaact cacttatcta ttgtttttatc   1860 tgtagaatga gtataatctc tcagtggggt agggaggcca attaaggatt gattacaaag    1920
tgccttacaa atagaaagct acagtgactt gtttgcaagg tgacagagaa ttcagaagcc    1980
tcaagaaact gccttaagtg atcaaacagg ctaacggagt tgccaaagca aaatagtgct    2040
gcactgatac tacctttaac cgttttttcc tttagcccctt ttcccccaa aaaaattagt    2100 atatgaaatt acagtgaaat acctggtatc taagcagatt tatagtaatt ctcaacatat    2160
tcatcaatct cttaattcta cctgcattaa aatgtatttc tacctgaaaa gtttaaaggt    2220
cttttatact gtgccatttt cctgattcat tgttgccaga ggtagtgagt tccttaattt    2280
tacagatatt tcaagaggac attggccagg tattattggt aaatcagatt tgttttttta    2340
gctggtagtg tttcacctct cctgagcact cctagttttt gacagtgtgc tttagtctcc    2400
ttccatgctg aggaaggcct tctctatagg agaaagaaaa ctgaggggtg tacacaggaa    2460
gttaccttat gctggggact caaaccttga tgctactgct ttgctccctg cctctatttt    2520
tgaaccaatt caacatctcc ctcctacccc aggaccttgt cacacactgt tctctttacc    2580
aggaatgttt ccctctcttt tcctctcctc cagaccctagt gaactcctat ttatcctcac    2640
ttggcacttg ctaagggaag cattcctgac ttccctgacc agatttactg ctccctgttt    2700
ctacagttcc tgtagtattt actactcctc catcatagtg catatttgta cccttgtgtc    2760
tgtctggatg cttatttgat taatacctgc ctcccccact aaactttaag ctccatgggg    2820
tcaaggccgt gactgtgtca gtatcgtagc ctgcatactt ggaatagtac ctggctcaat    2880
aaatatttgt ggagtaaata actgaataac tctccagagc ctataagata aatctagagc    2940
tgctgctttc aatcactgct ttcctggtgg tctgtggcct ggttctcttt cttctcacac    3000
tcttcccacc ttcagagtgc agccattgct ttggagagat gggagagaac atggcactaa    3060
ggcagaatat ggctatattt actttgaaga gcatgtcttt gtcatagaaa tagtcactgt    3120 catggttttgg tgggtcccaa ggcatgggtc atggctccag atcccctttc cagccttttg    3180
gatcttggta agtctgaacc cactgctgcg ttggcaaggc tctggaaact atagtgacag    3240
agaatgattc acaagtgtca acactcagat gtacagggct gccagctgac ccactctacc    3300
tatttccatc tggcactgaa ctggttgatc atgaacttct tttcataatt gcttttttagt    3360 tatgcaggtt aagacatgcc gaaacagatg taccggaccc acaaacaagt ccttccttga    3420
atgcctgagg cttcctaaca gtgaaagagc cctgttctta gagtaggcaa actgattctg    3480
aggcattgta ggtggtaggg atctggtagt aggtagcatt aggtgggctc ccggcactca    3540
ccatggagcc ttgaaatttt ctgctacttt ggggagttg ctggttcaga gaaggcccctt    3600 ccacccctggt agccatgtgg cactggaagg ctgtgaaaac tctgctgggc cttcttagtc    3660
atctgttgtg agctcctgat gggagtgtgg tgtatccctc aggtgtgcta gactggaaca    3720
aaggctgaga agtgttgctc tgggggttcc aacttgtggg catgggtac tgatgagatc     3780 agtagtgttt ggagacttct gtatgctcca tcttcagaag acattctgga gtccatataa    3840
gttatcttgt ctcttgtttg aagcaggaaa aaggaatgcg attgctggta atatagttca    3900
ctaaagtcag ctacctggcc tctaacagtt atttgcaaag tatattataa cattgattcc    3960
tcaaacatct agattcctat ctcgtgccaa gtgatgtact aggtgctcta agtacaaaaa    4020
```

```
taaaggaata tagtcctcct ctcaatgcgt aagcctagtg gaagaagcag aaatgaaagg    4080
gaaataagaa ttcaatagag tatgaggcat tacagtgaaa gaaaccaaat gtcttagaag    4140
tacaaatggc agagctacta attctgtctc gagcaggcag ggaagagtct atagtggaaa    4200
tgacttttga gctagatttt gaattgagct agtcttttga gccagacttt tgagctagaa    4260
ttgtagggtt gtcatcagac cagagagtag gaagggtacc ttgtgaggaa gagagagaga    4320
gatcagattg ttactgtgtc tatgtagaaa aggaagacat aagaaactcc attttgatct    4380
gtactaagaa aaattgtttc tgctttgaga tgctgttaac ctgtaacttt agtcccaacc    4440
ctgtgctcac agaaacctgt gctgtaatga atcaaggttt aatggattta gggctgtgca    4500
ggatgtacct tgttaacaat atgtttgcag gcagtatgct tggtaaaagt catcgccatt    4560
ctccattctc gattaaccag ggacacagtg cactgcggaa ggccgcaggg acatctgccc    4620
aagaaagcct gggtattgtc caaggtttcc ccccactgag acagcctgag atatggcctt    4680
gtgggaaagg aaagacctta ccaccccca gcccgacacc cgtaaagtgt ctgtgctgag    4740
gaggagtagt gaaagagcgg ggcctctttg cagttgagat aagaggaagg cttctgtctc    4800
ctgctcatcc ctgggaatgg aatgtctctg tgtaaagctg accattccca ttcgttctat    4860
tctgagatag gagaaaacca ccctgtggct ggaggcgaag tatgctggca gcaatactgc    4920
tctgttactc tttgctacac tgagttgttt gggtaaagag aaacataaat ctagcctgcg    4980
tgcacatcca ggcacagtac ctttccttga acttattcat gatacagatt cctttgctca    5040
cgtttccctg ctgaccttct ccccacctgt tgccctgcta cactcccctc gctaagatag    5100
taaaaataat gatcagtaaa tactgaggta actcagaggc tagcgctggt gcgggtcctc    5160
cgtatgctga gtgccggtcc cctgggccca ctgttctttc tctatacttt gtttctgtgt    5220
cttatttctt ttctcagtct cgtcccacct gacgagaaat acccacaggt gtggaggggc    5280
tggccccttt cagtatctca gaagggacaa agtacacaaa ggcatggggt catgatagtg    5340
cctggtatgt tcaggtagtg aagaggtcca tgtggtatga gcactgcaga tgatatgtgt    5400
cgtatgaatt aaaaatacat agttactgca aatagttttt acaggttatt gttttttaaga    5460 aagcagtatc taatgcacga gtgtactgtc agtactgtca atgaactact taccactcaa    5520
gtgactgctt acgcgtcgaa tcactagtga attcgcggcc gcctcgagtc tagaactagt    5580
ggatccccca aacgggccct ctagacgcgt tgacattgat tattgactag ttattaatag    5640
taatcaatta cggggtcatt agttcatagc ccatgatatc atatggagtt ccgcgttaca    5700
taacttacgg taaatggccc gcctggctga ccgcccaacg acccccgccc attgacgtca    5760
ataatgacgt atgttcccat agtaacgcca atagggactt tccattgacg tcaatgggtg    5820
gagtatttac ggtaaactgc ccacttggca gtacatcaag tgtatcatat gccaagtacg    5880 ccccctatt gacgtcaatg acggtaaatg gcccgcctgg cattatgccc agtncatgac    5940
cttatgggac tttcctactt ggcagacatc tacgtattag tcatcgctat taccatggtg    6000
atgcggtttt ggcagtacat caatgggcgt ggatagcggt ttgactcacg ggatttttcc    6060
aagtctccac cccattgacg tcaatgggag tttgttttgg caccaaaatc aacgggactt    6120
tccaaaatgt cgtaacaact ccgccccatt gacgcaaatg ggcggtaggc gtgtacggtg    6180
ggaggtctat ataagcagag ctctctggct aactagagaa ccctgctta ctggcttatc    6240 gagatatctg cagaattcat ctgtcgactg ctaccggcag cgcgcagcgg caagaagtgt    6300
ctgggctggg acgacagga gaggctgtcg ccatcgcgt cctgtgcccc tctgctccgg    6360
cacggccctg tcgcagtgcc cgcgcttttcc ccggcgcctg cacgcggcgc gcctgggtaa    6420
```

```
catgcttggg gtcctggtcc ttggcgcgct ggccctggcc ggcctggggt tcccgcacc     6480
cgcagagccg cagccgggtg gcagccagtg cgtcgagcac gactgcttcg cgctctaccc    6540
gggcccccgcg accttcctca atgccagtca gatctgcgac ggactgcggg gccacctaat    6600
gacagtgcgc tcctcggtgg ctgccgatgt catttccttg ctactgaacg gcgacggcgg    6660
cgttggccgc cggcgcctct ggatcggcct gcagctgcca cccggctgcg gcgaccccaa    6720
gcgcctcggg cccctgcgcg gcttccagtg ggttacggga gacaacaaca ccagctatag    6780
caggtgggca cggctcgacc tcaatggggc tcccctctgc ggcccgttgt gcgtcgctgt    6840
ctccgctgct gaggccactg tgcccagcga ccgatctgg gaggagcagc agtgcgaagt     6900
gaaggccgat ggcttcctct gcgagttcca cttcccagcc acctgcaggc cactggctgt    6960
ggagcccggc gccgcggctg ccgccgtctc gatcacctac ggcacccgt tcgcggcccg      7020
cggagcggac ttccaggcgc tgccggtggg cagctccgcc gcggtggctc ccctcggctt    7080
acagctaatg tgcaccgcgc cgcccggagc ggtccagggg cactgggcca gggaggcgcc    7140
gggcgcttgg gactgcagcg tggagaacgg cggctgcgag cacgcgtgca atgcgatccc    7200
tggggctccc cgctgccagt gcccagccgg cgccgccctg caggcagacg ggcgctcctg    7260
caccgcatcc gcgacgcagt cctgcaacga cctctgcgag cacttctgcg ttcccaaccc    7320
cgaccagccg ggctcctact cgtgcatgtg cgagaccggc taccgctgg cggccgacca     7380
acaccggtgc gaggacgtgg atgactgcat actggagccc agtccgtgtc cgcagcgctg    7440
tgtcaacaca cagggtggct tcgagtgcca ctgctaccct aactacgacc tggtggacgg    7500
cgagtgtgtg gagcccgtgg acccgtgctt cagagccaac tgcgagtacc agtgccagcc    7560
cctgaaccaa actagctacc tctgcgtctg cgccgagggc ttcgcgccca ttccccacga    7620
gccgcacagg tgccagatgt tttgcaacca gactgcctgt ccagccgact gcgacccccaa   7680
cacccaggct agctgtgagt gccctgaagg ctacatcctg gacgacggtt tcatctgcac    7740
ggacatcgac gagtgcgaaa acggcggctt ctgctccggg gtgtgccaca acctccccgg    7800
taccttcgag tgcatctgcg ggcccgactc ggcccttgcc cgccacattg gcaccgactg    7860
tgactccggc aaggtggacg gtggcgacag cggctctggc gagcccccgc ccagcccgac    7920
gcccggctcc accttgactc ctccggccgt ggggctcgtg cattcgggct tgctcatagg    7980
catctccatc gcgagcctgt gcctggtggt ggcgcttttg gcgctcctct gccacctgcg    8040
caagaagcag ggcgccgcca gggccaagat ggagtacaag tgcgcggccc cttccaagga    8100
ggtagtgctg cagcacgtgc ggaccgagcg gacgccgcag agactctgag cggcctccgt    8160
ccaggagcct ggctccgtcc aggagcctgt gcctcctcac ccccagcttt gctaccaaag    8220
caccttagct ggcattacag ctggagaaga ccctcccccgc accccccaag ctgttttctt    8280
ctattccatg gctaactggc gagggggtga ttagagggag gagaatgagc ctcggcctct    8340
tccgtgacgt cactggacca ctgggcaatg atggcaattt tgtaacgaag acacagactg    8400
cgatttgtcc caggtcctca ctaccggggcg caggagggtg agcgttattg gtcggcagcc    8460
ttctgggcag accttgacct cgtgggctag ggatgactaa atatttatt ttttttaagt      8520
atttaggttt ttgtttgttt cctttgttct tacctgtatg tctccagtat ccactttgca    8580
cagctctccg gtctctctct ctctacaaac tcccacttgt catgtgacag gtaaactatc    8640
ttggtgaatt ttttttttcct agccctctca catttatgaa gcaagcccca cttattcccc    8700
attcttccta gttttctcct cccaggaact gggccaactc acctgagtca ccctacctgt    8760
gcctgacccct acttcttttg ctcttagctg tctgctcaga cagaacccct acatgaaaca   8820
```

```
gaaacaaaaa cactaaaaat aaaaatggcc atttgctttt tcaccagatt tgctaattta   8880
tcctgaaatt tcagattccc agagcaaaat aattttaaac aaaggttgag atgtaaaagg   8940
tattaaattg atgttgctgg actgtcatag aaattacacc caaagaggta tttatcttta   9000
cttttaaaca gtgagcctga attttgttgc tgttttgatt tgtactgaaa aatggtaatt   9060
gttgctaatc ttcttatgca atttcctttt ttgttattat tacttatttt tgacagtgtt   9120
gaaaatgttc agaaggttgc tctagattga gagaagagac aaacacctcc caggagacag   9180
ttcaagaaag cttcaaactg catgattcat gccaattagc aattgactgt cactgttcct   9240
tgtcactggt agaccaaaat aaaaccagct ctactggtct tgtggaattg ggagcttggg   9300
aatggatcct ggaggatgcc caattagggc ctagccttaa tcaggtcctc agagaatttc   9360
taccatttca gagaggcctt ttggaatgtg cccctgaac aagaattgga agctgccctg    9420
cccatgggag ctggttagaa atgcagaatc ctaggctcca ccccatccag ttcatgagaa   9480
tctatattta acaagatctg caggggtgt gtctgctcag taatttgagg acaaccattc     9540
cagactgctt ccaattttct ggaatacatg aaatatagat cagttataag tagcaggcca   9600
agtcaggccc ttattttcaa gaaactgagg aattttcttt gtgtagcttt gctctttggt   9660
agaaaaggct aggtacacag ctctagacac tgccacacag ggtctgcaag gtctttggtt   9720
cagctaagct aggaatgaaa tcctgcttca gtgtatggaa ataaatgtat catagaaatg   9780
taacttttgt aagacaaagg ttttcctctt ctattttgta aactcaaaat atttgtacat   9840
agttatttat ttattggaga taatctagaa cacaggcaaa atccttgctt atgacatcac   9900
ttgtacaaaa taaacaaata acaatgtgaa aaaaaaaaa aaaaaaaaa aaaaaaaaa     9960 aaaaaaaagg tagcagtcga cagatgaatt ccaccacact ggactagtgg atccgagctc  10020
ggtaccaagc ttaagtttgg gctgcaggaa ttctgatggc tctcaaaatt cctgcctcct  10080
ttagggataa aagactttaa gactttttaa caaaaaagaa aaagaaaaaa aaattcctg   10140 cctcctggtg tacacacaca gaagggttcc ctcccttga atgtgaccag gatctgtgaa  10200
aataacggga tagccgctcc tgtgattagg ttatgtggta gactagagca agattctcct  10260
gctggttttg aagaagtcag ctgccatgtt gtgagactgt catgggctag gcatgagcc   10320 tttaaatatc tgggagcaac ccctggccag cagccagtga gaaacgggc cctcagtcct   10380 acaatcacaa ggaactaaat tctgccaaca acctgaagga actttgaaga ggatcatgag  10440
tcccttgatt cagcttgatg agcccctgag cagaggatac agctaacttg tactagggaa  10500
gtataaaaaa catgcatggg aatgatatat atcaacttta aggataattg tcatacttct  10560
gggaatgaag ggaagaaat ggggctttag ttgtattatg atctttaatt tctcaaaaaa   10620
aataagatca gaagcaaata tggcaaaatg ttaaactttt tgtgggtacg taggtattca  10680
gcatacccct ttttctgagt tcaaaatatt ttataattaa aatgaaatgc aggccaggca  10740
cagtggctca tgcctataat accagcactt tgcgaggccg aggtgggagg atggcttgag  10800
gccagaccag cctggccaac atggcaaaac cccatctcta cttaaaaaaa aaaaaactat  10860
atatatatat atgtgtgtgt gtgtgtatat atatatgt atatatattt atatatgtgt    10920
gtatatatat atgtgtatat atatttatat atgtgtgtgt atatatatat atacacacac  10980
acacatatat acatcatac atacacacac acacacacac aattagccag gcatggtggc  11040
gcacacctgt agtcccagct acttgggagg ctgagacatg agaattgctt gaacctggga  11100
ggcagagtag ttagtgagct gagatcatac cactgcactc cagccggtg acagagtgag   11160 actctgtctt aaaaaaaata aaaattaaaa ttaaatgcaa aaggtccaag tgaattgaag  11220
```

```
aggaaagggg tatcaaggaa ggttttgtgg aggtgacgtt tgagctgggt cttaaatgac   11280
ttaaacatgg gataagaagg gagggaataa ggacatttca ggtacgagaa ataaggagca   11340
aacagtggaa acaacctaac gtctgtcaac cagtgaatgg ataacaaaaa tgtaattcag   11400
atggtatcca acttacgatg gttcaacatg agattttttct gactttagga tagatttatc   11460
aaagtagtaa atccattttc aacttatgat attttcaact tcagatgggt ttatcaggac   11520
acagttgagg aacacctgtc tatccataca atttggcaat aaaaaggaaa tgagtgcaga   11580
tatactccac aacatgaatg aaccttgaaa acattaagtg agagaagcca gatacaaaag   11640
gccacatatt gtatgattct atttatacaa aatgtccaga ataggcaaat cttatagaca   11700
gcaagtaggt agatgatcag tttgctaggt gctggggaa ggggaaatgg ggagtgatgg   11760 ctaagggat tgggtttctt tgtgggcaa tgaaaatgtt ttaaaattga gcgtgataat   11820
gattgcacaa tgctgcatat atatataatc tatagattat atatatataa agagaggctg   11880
ttagacagtg ataagtgata tatatatata tacataga gagagagaga gagagagaga   11940
gaggctgtta gtgataagtg atcaggaaaa taaaagtatt gaggaggaat acgaagttga   12000
cggtgtgaaa acatgagatt ttatatagga tggccaggga aggccttaat gagaaagtga   12060
cttatgagta aaaacaaggg atcctaaacc ttagcatgca tcagaatcac tcggaaactt   12120
gttaaagcat agcttgctgg gcctcatcac agatattttg attcggtagg ttcttgtctg   12180
atattaatac ttttggtcta gggaaccaca ttttgagaac cactgagcta aaggaagtaa   12240
aggtttccct tagtttacta gctggtaaca ctggcccagg aggcctttct ggaaaaggtc   12300
ccagtcccca aaggaagctg gggactcgcg ttcacatcgt caaggtttac caagttgtgg   12360
cgggcctttc cgtcttggaa aaagcctcaa aatggcagat tagggtgtcc atggccggcg   12420
gaaagggtct ttgaagttgc agaccaggag ggaagaagat tctgggcctc ccccatgcag   12480
tgtcagctgg caacagaatg caccccggct gggttggagg ccctgggtac tggctcttcc   12540
acaccagggg cccacctacc aagggcagca ggagcatctg cacctcctgc gccaggcgcc   12600
cttcagtgct tccacttgag cacctctcca gacaccagct agggtgacag tggtacaaat   12660
accagactcc cctggcctgc tcacctcaca gggtaatgtg ctgtggagtc aggggacac   12720 agcaaccacc agatgacatg gctggcccg gggaggacga cacgcagata cggctacttg   12780
gcacctgtga tattttacac actcgagagg ggcccgcacc atcctcagcc ctctccccac   12840
attcactctt agttcatgtc acctccaccc agaggggac acaggccac agcgatggcc   12900 ccacaccctg cctgaggtcg cccacttccc aggaggcagt cctgggactt ccacccgacc   12960 aggcccaga gccaccgac ttaacccctc cagaggcttg tcgttcatta ccttattcaa   13020
gatggagacc agccttttg cggagaaaat gcgggtgaag gtcctgaaag tgcattgacg   13080
ccgttttcgg aagccataca agtttagctg gcggaagaag ctctttatcg aagttgtggc   13140
aaacactttg tgtgcgacgt ccctttggag aatctccttt tcaaagagtt tttgattgat   13200
cactctacaa gccccactgt catcccacca gatggacgaa aactggttgc tgctgaccag   13260
tctccacagt ttctgtggaa aggggaggga gaggagatta tcttctccct ggggcggac   13320 gtcaccgtca gggtgcggcc ttctgaacga agcttcctcg gccagaggtt ggaaagcgat   13380
ttcttctgtc agcagcctca agttagggct cccagtggac cccgggtcgt cccaggcagg   13440
ggaaggatct gctgggtgaa ggtaggtctc tgactgcaac tgggaggga aaggcaccct   13500 ttccaagcca tgatcctgtc ctctcgaatt tctttcttca cagcgagcca tactcaatga   13560
tcgcttgtcc tccatctggc aaacttgcta gtgcagtgtg gccagcagca ccccttggca   13620
```

```
gtcatgtaac cagccccatg acatcataaa ggggctctga ctgccggggg gtggcatctc   13680
cacccccagc aagttgtgta ataaagggcc aaggcagaca agtagctgcc catctgcatg   13740
tgcacattct ggtcctcaca gtcatttcaa tgggaaagat gacactagtg cacaagagtg   13800
ccgaggggcc ctgccacacc gtagatgcag acctggagcg gtccccttgt cctagagctc   13860
ctgagccagg cacaactaca gcaaagccct ggctcaggaa ggtcagagct caccgtctga   13920
gtcatgggcc cacagacccc agcacatgac tgacactcgg aagcacagaa caaagggtag   13980
gacggtgccc atgggtcagg ctgtagccac gccacccttt ccaccctgtc ctagccagag   14040
gcagcaatgt gctccataca gatcctccta acacacccac actgtcggtc cccagcacgc   14100
agatgcccga cagccccttta ggcaaatggc ttagctgact gccccaccac acgccgtcgc   14160
catgcagtcc agtggggagt cggaggcagc ctccttcctg cctctcctcg gcctgcacgt   14220 gtcccccccac caggcagaga cccttctaca ccccgggtgt ctgcggtcac atcgcggtgg   14280
ggcatgcagc tgttggcctt cgagcatgtt ttgttttcct tggccagtgt ctccagagaa   14340
acgcacgtgg gtttgtgtcc agcggtccat ctctgcaaca gttgttcctt tgggattgga   14400
tgctaggagt tcacgggaga ggtgtccatc caaagcagtg tctgtgtcac acactgtccc   14460
cacacacagg gccacctctg cacagactcc cccgactcga ttctgggcac agagctcagt   14520
gaccttccag agactgccac gaaccggtga tgcctccacg cttgagacat cctgaccgca   14580
gggcccaagg cgcactggct caggggggtga cagtgagggg tctgcaaaca gactgctgat   14640
gctcaacccg gccgctgccg agctgtgtga cttgggcacg tcacttaacc tctctcggcc   14700
tctgtctcct cccggggata agagtagtag cacctgcttc ccggggctgt gaggatccag   14760
tgggacgtat aggaactagc gaggcaccgg cagttgggtc agagctactg ttgtcacttc   14820
acaaggcatt ttcttcaaca gcaagtcgga aatctcatga gcctaaggca gaatccacct   14880
gtggcctctg gttacaaccc acaggactga aaatccttcc agccacagca actggtgaat   14940
ttcctggtca attgccacaa gtcatgagct gaaccccact tgagtttcag ttcaggcaga   15000
actctagaga cgactagggc aagctagaca gcgactgcag agccttttgt tgcagcgtga   15060
gcagtcctca gctgttgaca tcactgggga gcaaacgagg accaggagcg gtgaaaggac   15120
agtgtctgct gcagattgtc gtagcaccca aggaacactc cagaaagcct cctaagcagt   15180
aacaagtgtg gcaaggtgta gcccagccaa cagtggcatc tgcgaggcgt ccctccttc   15240 ctcccactac cccgtatacc ctgggacctg tgcactgaag gactcattct aaaggctgtg   15300
cccctgcagc cgccagcctc actcactggc tgcctgtgcc agctagagat ttctttcctc   15360
tgaggctggc tgagaggacc actccagttt cctggcccat ccagcaaaga agatacacat   15420
catgcacgtg taaaatgagg aaccggttta ttgaacagct taaggagagc aaaaatagtg   15480
gctttagcta catttttttac acactgagca ggaaagtcta aaccatcccg ttcccctgta   15540
ccccaaagag aacagggctt gctggaggcc agtgccaagg gcggagtcgt gctcgcagca   15600
gacttgaatt aaccccatgt aggccggcga gcagttgccc gcgtgaaaac accaccctct   15660
tctcctggct gagaagatca aagctctttt tttaccctct tttcagcaaa ggacctattt   15720
gttttcaggc aggaggatgt taaacttgca gcctctgaca cacggtggaa cctgcagtgc   15780
ttggagaaac ggcacgcaca cgtgaaaaca tcatgcctac tccaaagcct tcttgttgct   15840
ggcaggaggg aagcttgaga ctttcccacg catagtcgtg acccgcgtgg ccgtttctgc   15900
tctcagcaac attctctagt gttccggctt caagcagcgc ttgtcaggtt tgaagctagc   15960
cactattctg agaacgtcag aaaagcatgg accatctctt gcttggtgtt gccgttgtgg   16020
```

```
cagtagcagc tactacgtac ctgcacgagt tccagggcag aagtggcaat gtcccatgaa    16080
ggcgtggcac cccacggggg gggggggggga gtgtgccacg ggcgtccact tctgcagcag    16140
aaggcatgtg cctacagcac aagcttgtaa aaaatactt gaacagaata tgctgtacag     16200 aactagggt taacaccgca tatgaagatg ctaaaacatt tgtataaata ctctgtatac     16260
aagcatggag tcactcccgt agaaagggct catccgtgag gctatgaaaa actgctgtca    16320
gcatgcccaa agagaaacta cttccacagt aggaacagaa aaaggactg tgctgtgtct     16380 aaacacgtgg tgcatcagag acatagttac agttcctact gactgcccca gccacgacct    16440
gggagtgctg aggacctggg agtgctcagc gagctgcagg aggtcagccc tgtggagaaa    16500
tacatttcta aacaatactt ttgattggga tttcagcacc gtatagacag atgttccttc    16560
tgggggcctg gcaagcagcc atctcccagt gggtctgacg gggaagaggg gtacctggag    16620
cccctcccag acagacggta atcccacccc tgttctcaca ctcttcctgg catccgcatc    16680
tgctggcaca caccccgtc acctgccact tccgcgtccc gtcgtggtga gtggctgata     16740
ggcgctggat gcaaacaagg catgagatgg acgtacctgg agacccagct ccagtactgg    16800
ttctggtctg cggggtgaac gaggggggcag aggaaggcgg agagagtgcg tcccagtcca   16860
cttaagctct gtccccggaa gtggcatcta atctggcatt tcgatattta atttgggagg    16920
tgggagcaca tacttcccag ggctctgggt aatgaccacc ctggccttct ttcgaaacat    16980
gggtgcgatt ttaggggggct ccggaactgg ggtctcttcg gtttcttcat tatcttcgtg   17040
atggagatca taggaaatgt ttccatattc tcgtagaaat gggaagattt caagcagaaa    17100
ctgacagaaa tctttgcgga taccaaacca ccctgaaaaa taagaatttt ttatttcaca    17160
cacgaggctc aactgacctt cctgttaact ttctttccgt aacaagaagt ttcactccta    17220
caatgtcata acatacttta tccagactcc tgagtcacaa agcctgaaca gggcttgagt    17280
acccaaaatg gggaagaagt gcaaatgcta gctctgtggt gcttggagtg gggttcccgg    17340
accggcaggg acagcgtcca cggggcctag ttagggatgc cattctcggg ccccagccca    17400
gacctccaga aactgagtcg ggctagggtg ggctccagcg gtccccttt cctggccctt     17460 ttgggattct gctggatgcc caaatttgag aactactgct ccagtgagtc tcaaaatatc    17520
tgtggtgcgc agactacggt gtcttccgct aatcttctcc agccaggata aactcatgga    17580
tgacagtgcc acccaagaac aagatttctg tcaccctctg gaatccgtga gggcggtagt    17640
catgcacggg ttggccagga gggggcctga actcatggag ccaccttaaa gccactttcc    17700
cagtcccact actcctctct gtaggctact ggagtgtcag ctcggtgcaa gccctccctg    17760
ctcccgggtg cggggtaggg ggcagaggca caaacagcaa gcacagcccg ggctgctggg    17820
ctgcagtgag gccctgcccc caaacccact ggctttccga agggcaatgc tctgggcttc    17880
cgtgccatgg agcccacagc cttgccagga aggcaccctc tgcagagatc gttttggaag    17940
tgtctgcctc agcaagcagg tggagggaa tagagtgtta gcaaggcaag acaggcaaga    18000
ctcgggtgat ggcagcaagg atatggggga ggcagagcgg ccaacaggga cctaggatga    18060
atcccaggtt tgggtgggag atgtggattt tccatcaaac cctcccgggc ctgggaagaa    18120
tctgtcttga tccccatttt gcagaggagg gaacgggatc tctgagaggt tgcctgccgt    18180
gtctggttct acctcaaatg gcagcgtgca ctgcagaaa agtcccggtg caggccagca    18240
gaacaccaga gttacggcat gcccttccct tagaaggtcc cagaatttcc tcagccctca    18300
ctttcccaca caagcttcta aattgggggcc ctcggggact catcccttcc tagacttcta   18360
tccgccaccc cccaccccct ggtcccccccc cagacacaca ccaaggactt ctgaaatgct    18420
```

```
gagtacatac agtggtttcc tcccttctgt ccaaatgtgg ttgccatcag cgtgatcaac   18480
gagagccaaa gggggacaaa gatcgggatg caggagaagg cgttgtggcc atccagtttg   18540
tgaaccagca gaatctaaag aaagagacat agtcccggtt gatgccagca ccgaaaatgg   18600
gcagaggcgg aagccagact tcattaggca gttcctcccc accacccac ccccgcgtga    18660 gctcccacaa gagggaacat cagcaccgcc agaaaaaggc aggaaaccac ctatccctgg   18720
ggaaagctcg aaatgagctt ttatgtccct cttcagagct cggcaatagc ctatccactt   18780
gaaaagttcc cagtgccagc agttttatgg caaactcctc cgggtgtttg ttctaaggag   18840
tcaacagctc ccattctaga attctccacg tgactccaat acacaaatct gacatcccac   18900
tctgctttcc ccagagtgga aactggagcc atacagaggc accatggcta aaaaggtgca   18960
ctcttctccc tgccagcccc acgtgctgcc cccaagagaa aggaaggatg ctctcctttc   19020
accgaagctc cctctcggag atggctgtgt tctctcccct ctcctggagt gggctcactg   19080
tgagctcgag ggacagaggc tgcctttcta ggggtgcaga atcctgtcag gggaagcgca   19140
agcttcaggg gctgaagagg cttcccgtgg aacgcttacc tcaaatgtaa aaggggcac    19200 gacgatggtc atccagctca gggccatggt tatgtgtgtc ctgcgctgtc cgcaatcaca   19260
tccatagagc gcaagaacaa gacggaccac acaatgtagt agaggaccac caggcacaga   19320
aaggacatga gaatccacag cgggacacac acaacctggg ggtgggtgag agaacagcaa   19380
gagaagtctc tttagagctt ccaacctggc ctctgatgga aggcatcttt agcaccttgc   19440
tgtgtctgtc cagttaaggc ggtccttcct gtgagccgaa taaggaccgt tccatctccc   19500
aggactgctg ggagcatcgc tcaggacaga aaaggtatgg tatgttcact atggggcctg   19560
ctgccaccag gggacacaca cgctcagtga gtcatcagtc cctcttcctt tgggtgacag   19620
acagccctgc acctggctcc gcagcctcta ctcttccaga ggcccactct cccacactct   19680
ctcaggctcc tctaggttct gctgccatca cagcttcccg ggaaatggga cacaactgtc   19740
accctgtgca cacacacaag atctcacccc aacagactct cttcacaggc aacattccca   19800
caacctgctg ggggtacttt ggcaacacaa atgggaatgg gctccccaga aagtctggct   19860
gcctgggctc ctaaggatcc ctaacctcac ccctaccaag ttagtgaact tggcgggttg   19920
atgctggata caggttgatg ctggatacgt agcgctgccg ggtcgtgacc cctaaggaat   19980
tatccaaact cttgttttta gatgctttat tatatcaaac tctcctttaa acaagtggcc   20040
catctgctgg gatttggaag cctgtaatac tgaaatttc atcataatgg aaattttaaa    20100
aacagaattt gacccacctg ttttttaaaac actttcatta cttaacaaga ggtctaatct   20160
tgggcaagtc ttgaaatttc tctggcctta gtttcccatg tgttaaatga aacttgaagc   20220
agttggtctc ttatagtctc ctgactctaa cattctaaga attatatttg tacaataact   20280
caaaaatcac ataatttaat ttaccatatg gactccaaaa tatattttct cattaggcta   20340
aacttgatct gcattttctg gatgtgtcca tattcttgga ctacactaaa acatgatacc   20400
aatgcttcct ctcaccataa accctcactt cgctttctac atttaagaat tttatagctg   20460 gaaagtcct taacagaaaa taccatctaa taattacccc tcaaaatcga aaagtcctaa    20520
tctgttctta tgctagttat aagaatgagg cagcatttca cataatggtt ataaacactg   20580
ccacaagaag attcatgatg tgttgtttat ctgtagctct catcatactc tgtcatataa   20640
ctatagcatt aagatttaa tgttctatat attcttctaa acagtgtttt accagagtaa     20700
ggcacaaaag atccactggt ttgcaagaaa gattagaact tttaaatttt ttacctcacc   20760
ttgtttaatc tatatttttg tatgtatttt gtaacatata tattattatt accataaatc   20820
```

```
atatataatt taaaatgcat atattagggg taaatgctca ggaaacttttt tataaattgg    20880
gcatgcaaat acaagtttga agactcactg ttctaggtat taaaagtaaa gttataacca    20940
agtaaagctt ccaccttttc atgtctcaaa gcagtttatt gttggaggta agatctctta    21000
gaagcctaaa caggtccaag tacagaatga agtaaggcta gcccataact tgtggcaagc    21060
aattcatact atttctctca tgctgagctc tcctcagtga agcagctact atagacaact    21120
gcagccatt ggtagcctat tttacaggca ggaaaaaaat tacttttat tcaaagtgga      21180
actcaggaca tggggagaaa atgaatacaa aaaatagggt caatccaaag gcacacagca    21240
aatgagtaac acagttatgt ttttttccca tttgtatgag gtcccagtaa attctaagta    21300
aactgcaaat ttaataatac actaaaaaag ccatgcaatt gttcaaatga atcccagcat    21360
ggtacaagga gtacagacac tagagtctaa aaaacaaaag aatgccatta ttgagttttt    21420
gaattatatc aagtagttac atctctactt aataaatgag aaaaacgagg ataagaggcc    21480
atttgataaa atgaaaatag ccaagaagtg gtattagaga cttgaataca ggtattcggg    21540
tccaaagttc atctgctcaa atactaactg gggaaaagag ggaaaaatat ttatatacat    21600
atatatctgc acacaaaaat acccccaaaa gacaaaatga ggccaggcag ggtggctcac    21660
acccgtaatc ccggtacttt gggaggctga ggcaggtgga tacctgagat caggagttgg    21720
agatcagcct ggtcaacatg gtgaaaccct gtctctacta aagataaaaa aattagccag    21780
gcatggtggc gtgcgcctgt aatcccagct acttgggagt ctgaggcagg agaatcactt    21840
gaactgggaa ggggaggttg cagtgagcca agatcgtact actgcactcc agcctgggca    21900
gcagagtgag actccatcac aaaaataaat aaataaataa aatacaatga aacagaaagt    21960
tcaaataatc ccataatctt accaccaaga aataactttc actcgttata cttattgatt    22020
tttccataat aaatgtactt tactgtgact atcatgaaaa gaaagttatt ttagaaacag    22080
agaactgttt cagatcaaat ctatgtagta gaacagagcc attaggtggg aaagacgaga    22140
tcaaactaaa tctcagaagg cctaaaaggc taggtccatt ccagcactaa aaactgacca    22200
gacaagtaat ggcttcaaca gcttctaaat atggacaaag catgctgaaa gggaaggaca    22260
ggtctaacag tggtatatga aatgaacagg aggggcaaag ctcatttctc ctctgaagtt    22320
ttccaaagat gctgaggagg acattagttt gacatgaccc tgatatggga caagataatt    22380
tcacagaagt tttacatgtt aaagtttctc tatagatact cattcaagta agcaatgaac    22440
actaaaatct aaagaaagaa aagagcttta gagtcaggtc tgtattcaaa ttcaagctct    22500
accacttact ggttctgtga ctttgggcaa gtcttttaac cttattaagt cttaatttcc    22560
tgatttgtaa aatggggata tcgtctccct cacaggattg ttgtgaaact tttatgagat    22620
taatgccttt atatttggca tagtgtaagt aaacaataac tggcagcttc aaaaaaaaaa    22680
agcagtagca ttccatcatt tattattggt tactctcaaa aagtttttca atgtactaga    22740
agataaatat tcaaatacct taatatctcc attattttca ggtaaacagc atgctcctga    22800
acaaccaatg ggtcaacaaa taaattaaaa gggaaatcta aaaacatctt gatattaaac    22860
tacatggaag cacaatatac caaaaccaat ggttcacact aggagaattt taaggtacaa    22920
gaaaactctt tgagatttct taaaataata gtatgtctga atttattgag tgatttacca    22980
gaaactgttg taagagctct acttgcatta tagcacttaa tcctcttaac tctatggctg    23040
ctattatcaa cctcacccta atcacatatg ggacacagag aggttaagta acttgcccaa    23100
ggtcagagtt aggaagtact aagccatgct ttgaatcagt tgtcaggctc cggaactcac    23160
actttcagcc actacataat actgctttgc tatctttag gaaactatgt gagtctacct    23220
```

-continued

```
cacatagact cacataggtt tgttttttt ttttttttaa aggctatctt ttcccccatc   23280
aatgtttttt gaaggatccc aaattagagt cccacagagg cagacagcag tacttgacaa   23340
tatggacatt taaggttaat gttggattct actgtctttt tactacatga cctagggaac   23400
gataattaac ctagactgct tccaagggtt aaataaccca tttagttata ctatgtaaat   23460
tatctcttag tgattgattg aaagcacact gttactaatt gactcggtat gaagtgcttt   23520
tttttcttcc ctttcaagat atacccttt ccagttaaag ttgagagatc atctccacca   23580
attactttta tgtcccctgt tgactggtca ttctagttaa aaaaaaaaaa aactatatat   23640
atatatatct acacacacat atgtatatgt atatccttat gtacacacac aaacttcaaa   23700
ttaaatgaga actagaagat ttgagaagtt agctagctaa tatccatagc attatgatat   23760
tctaaatgat atgaattata agaattaggt ttcctgaaat gaatgactag aaaactttca   23820
agtagagatt agtaaaaatt aaaaagtcct aatcggccat tactgatttg atgtttttaa   23880
gagtcctaaa aaatgggtta catccatttt taagtgggta gtattataac agccacccat   23940
cttcaatcac agtgatttct gaattgtgag ggaagttatt agcatgacag gtgtctggtt   24000
ctggccctgt acgattccca tgagtcaagc aaattgtaag ggctggtcta tatcacaccc   24060
aaccccaagg atatgtccct caaaagtcta gcccaggccc cgtcatcttc agcatcatct   24120
gggaaaccag gtctgattag tagtccttta aggaatacct cttaggctcc cattttactg   24180
ctatcacaga atccaataaa acccttacag gagattcaat gggaaatgct caacacccac   24240
tgtagttggt ggtgacaatg accataattt ggctgtgctg gattcaggac agaaaatttg   24300
ggtgaaagag caggtgaaca aaagagcttc gacttgccct agcagagagc aagccatacc   24360
ataccacaaa gccacagcaa ttacaacggt gcagtaccag cacagtaaat gaacaaagta   24420
gagcccagaa acagacccag aactatatga ggatttagta tacaataaag atggtatttc   24480
gagtcagtag ggaaaagatg aattattcaa taaatgatgt ttggccaact agtaacccat   24540
ttgggaaaaa ataaaagtat ggtccctacc tcacagcata cacaaaaata aattccagac   24600
ggattaaaat ctaaatgtaa aaaataaagc cataagtgga ctggaagaaa atagagaatt   24660
tttttaaca tccgtagaaa gggtaaaaac ccaggcatga catgaaccaa aactgaagag   24720
gttctgtaac aaatacccc ttttatatat tgggctccaa caataagaac ccataggaaa   24780
atggagaatg aacacaaata gacaatttat agaagagaag gttataaggt gtaaaattat   24840
atctatctga gaaacaaaca ctaaaacaat gtgattctac tgttctccca cccatactgg   24900
caaaacttaa gcctgataat atgctgaggg gaaataagca ctcttgttgg tgagagtatt   24960
aattggcata gcttcttttg aaaatgacat agcaatacct gttaaaattg caaacatgca   25020
tgtcacttaa tccagtaatc ccacttctgg gaatcaatgc tacaaaaaca ctgacaagta   25080
tacaaagata cattcaagag tgttcactgg gccgggtgcg gtggcttcat gcctgtaatc   25140
ccagggaggc agaggcaaga cgatcgcttg accccaggag ttcaaggcca gcccgagaaa   25200
cacagcaaga ccctgtctct cttttttta tttaaaaaat aaatgttcac tgtatcagtt   25260
gttcacaaaa acaaaccaac atgtccatta acagggaacc attaaaatta atcaagttca   25320
tctacacaat gtaataccat gcaactatta aaagcacct gataatccaa agcacactga   25380
gacagaataa tgctattaaa aacaccaagt agtggaacac tgtgttgcct atgacaccat   25440
ttttattcaa catttaaaca aatttgtaac agcaattaca tgagtagtga caatggcgtt   25500
tatgagactt ttcactttta tgtgcttcta ttttgttat gcttctatat atacatccat   25560
ttattatgga gtgttacttt caaaaatcac aaatgggcca gtattatttg gtgttgcaag   25620
```

```
gtgagcatat gacttctgat atcaaccttt gcatattact tctcaattta gggaaattac   25680
agacatccct tattctaact aacttaaaac ccagcatttc aaacatacag aattgatggg   25740 gaaaaaaag aaagaagaaa gaaagaaaag gcaacaagct tcagatgaca gtgactcaca    25800
tcaaattatt tataaaatct gttaaatagt gccatcttct ggagatacct ggtattacag   25860
tccaactcca gttgatgtct ttacagagac aagaggaata aaggaaaaaa tattcaagaa   25920
ctgaaaagta tggagtcatg gaaaaattgc tgtgatccaa aggctacggt gataggacaa   25980
gaaacaagag aactccaagc agtaagacac tgctgttcta ttagcatcca aacctccata   26040
ctcctgtttg ccccaaggct ttttaaaaa atagagacag gatctcacta ttttgctcag    26100
gctggtcttg aactcctgga ctcaagctat cctcctgcct cggcctccta aagtgccgag   26160
attacaggct tgagtcacca tacctggcta tttattttt cttaactctc ttgcctggcc    26220
tatagccacc atggaagcta ataaagaata ttaatttaag agtaatggta tagttcacta   26280
cattggaata caggtataag tgcctacatt gtacatgaat ggcatacatg gatcaattac   26340
cccacctggg tggccaaagg aactgcgcga acctccctcc ttggctgtct ggaacaagct   26400
tcccactaga tccctttact gagtgcctcc ctcatcttta attatggtta agtctaggat   26460
aacaggactg gcaaaggtga ggggaaagct tcctccagag ttgctctacc ctctcctcta   26520
ccgtcctatc tcctcactcc tctcagccaa ggagtccaat ctgtcctgaa ctcagagcgt   26580
cactgtcaac tacataaaat tgccagagaa gctctttggg actacaaaca catacccta   26640 atgtctttat ttctattttg tctacctctt cagtctaggt gaaaaaatag gaaggataat   26700
agggaagaac tttgtttatg cctacttatc cgcccctagg aatttgaaa acctctaggt   26760 agcaataaga actgcagcat ggtatagaaa aagaggagga aagctgtata gaaatgcata   26820
ataaatgggc aggaaaagaa ctgcttggaa caaacaggga ggttgaacta taaggagaga   26880
aagcagagag gctaatcaac aaggctgggt tcccaagagg gcatgatgag actattacta   26940
aggtaggaat tactaagggc tccatgtccc cttagtggct tagtactatg tagcttgctt   27000
tctgcagtga acttcagacc cttcttttag gatcctagaa tggacttttt ttttttatcg   27060 gaaacagtc attctctcaa cattcaagca ggccccaagt ctaccacact caatcacatt   27120
ttctcttcat atcataatct ctcaaccatt ctctgtcctt ttaactgttt ttctataccc   27180
tgatcaaatg ccaacaaaag tgagaatgtt agaatcatgt attttagag gtagactgta    27240 tctcagataa aaaaaaggg cagatattcc attttccaaa atatgtatgc agaaaaaata    27300
agtatgaaag gacatatgct caggtaacaa gttaatttgt ttacttgtat tttatgaatt   27360
ccctaaaacc tacgtcaccc gccccgttcc cacgccccgc gccacgtcac aaactccacc   27420
ccctcattat catattggct tcaatccaaa ataaggtata ttattgatga tgttaattaa   27480
catgcatgga tccatatgcg gtgtgaaata ccgcacagat gcgtaaggag aaaataccgc   27540
atcaggcgct cttccgcttc ctcgctcact gactcgctgc gctcggtcgt tcggctgcgg   27600
cgagcggtat cagctcactc aaaggcggta atacggttat ccacagaatc aggggataac   27660
gcaggaaaga acatgtgagc aaaaggccag caaaaggcca ggaaccgtaa aaaggccgcg   27720
ttgctggcgt ttttccatag gctccgcccc cctgacgagc atcacaaaaa tcgacgctca   27780
agtcagaggt ggcgaaaccc gacaggacta taaagatacc aggcgtttcc ccctggaagc   27840
tccctcgtgc gctctcctgt tccgaccctg ccgcttaccg gatacctgtc cgcctttctc   27900
ccttcgggaa gcgtggcgct ttctcatagc tcacgctgta ggtatctcag ttcggtgtag   27960
gtcgttcgct ccaagctggg ctgtgtgcac gaaccccccg ttcagcccga ccgctgcgcc   28020
```

```
ttatccggta actatcgtct tgagtccaac ccggtaagac acgacttatc gccactggca   28080
gcagccactg gtaacaggat tagcagagcg aggtatgtag gcggtgctac agagttcttg   28140
aagtggtggc ctaactacgg ctacactaga aggacagtat ttggtatctg cgctctgctg   28200
aagccagtta ccttcggaaa aagagttggt agctcttgat ccggcaaaca aaccaccgct   28260
ggtagcggtg gttttttgt ttgcaagcag cagattacgc gcagaaaaaa aggatctcaa   28320
gaagatcctt tgatctttc tacggggtct gacgctcagt ggaacgaaaa ctcacgttaa   28380
gggattttgg tcatgagatt atcaaaaagg atcttcacct agatcctttt aaattaaaaa   28440
tgaagtttta aatcaatcta agtatatat gagtaaactt ggtctgacag ttaccaatgc   28500
ttaatcagtg aggcacctat ctcagcgatc tgtctatttc gttcatccat agttgcctga   28560
ctccccgtcg tgtagataac tacgatacgg gagggcttac catctggccc cagtgctgca   28620
atgataccgc gagacccacg ctcaccggct ccagatttat cagcaataaa ccagccagcc   28680
ggaagggccg agcgcagaag tggtcctgca actttatccg cctccatcca gtctattaat   28740
tgttgccggg aagctagagt aagtagttcg ccagttaata gtttgcgcaa cgttgttgcc   28800
attgctgcag ccatgagatt atcaaaaagg atcttcacct agatcctttt cacgtagaaa   28860
gccagtccgc agaaacggtg ctgaccccgg atgaatgtca gctactgggc tatctggaca   28920
agggaaaacg caagcgcaaa gagaaagcag gtagcttgca gtgggcttac atggcgatag   28980
ctagactggg cggttttatg gacagcaagc gaaccggaat tgccagctgg ggcgccctct   29040
ggtaaggttg ggaagccctg caaagtaaac tggatggctt tcttgccgcc aaggatctga   29100
tggcgcaggg gatcaagctc tgatcaagag acaggatgag gatcgtttcg catgattgaa   29160
caagatggat tgcacgcagg ttctccggcc gcttgggtgg agaggctatt cggctatgac   29220
tgggcacaac agacaatcgg ctgctctgat gccgccgtgt tccggctgtc agcgcagggg   29280
cgcccggttc tttttgtcaa gaccgacctg tccggtgccc tgaatgaact gcaagacgag   29340
gcagcgcggc tatcgtggct ggccacgacg ggcgttcctt gcgcagctgt gctcgacgtt   29400
gtcactgaag cggaaggga ctggctgcta ttgggcgaag tgccggggca ggatctcctg   29460
tcatctcacc ttgctcctgc cgagaaagta tccatcatgg ctgatgcaat gcggcggctg   29520
catacgcttg atccggctac ctgcccattc gaccaccaag cgaaacatcg catcgagcga   29580
gcacgtactc ggatggaagc cggtcttgtc gatcaggatg atctggacga agagcatcag   29640
gggctcgcgc cagccgaact gttcgccagg ctcaaggcga gcatgcccga cggcgaggat   29700
ctcgtcgtga cccatggcga tgcctgcttg ccgaatatca tggtggaaaa tggccgcttt   29760
tctggattca tcgactgtgg ccggctgggt gtggcggacc gctatcagga catagcgttg   29820
gctacccgtg atattgctga agagcttggc ggcgaatggg ctgaccgctt cctcgtgctt   29880
tacggtatcg ccgctcccga ttcgcagcgc atcgccttct atcgccttct tgacgagttc   29940
ttctgaattt tgttaaaatt tttgttaaat cagctcattt tttaaccaat aggccgaaat   30000
cggcaaaatc ccttataaat caaaagaata gaccgagata gggttgagtg ttgttccagt   30060
ttggaacaag agtccactat taagaacgt ggactccaac gtcaaagggc gaaaaaccgt   30120
ctatcagggc gatggcccac tacgtgaacc atcaccctaa tcaagttttt tggggtcgag   30180
gtgccgtaaa gcactaaatc ggaacccta agggagcccc cgatttagag cttgacgggg   30240
aaagccggcg aacgtggcga gaaaggaagg gaagaaagcg aaaggagcgg gcgctagggc   30300
gctggcaagt gtagcggtca cgctgcgcgt aaccaccaca cccgccgcgc ttaatgcgcc   30360
gctacagggc gcgtccattc gccattcagg atcgaattaa ttcttaatta acatcatcaa   30420
```

```
                                        -continued
taatatacct tattttggat tgaagccaat atgataatga gggggtggag tttgtgacgt    30480
ggcgcggggc gtgggaacgg ggcgggtgac gtagtagtgt ggcggaagtg tgatgttgca    30540
agtgtggcgg aacacatgta agcgacggat gtggcaaaag tgacgttttt ggtgtgcgcc    30600
ggtgtacaca ggaagtgaca attttcgcgc ggttttaggc ggatgttgta gtaaatttgg    30660
gcgtaaccga gtaagatttg gccattttcg cgggaaaact gaataagagg aagtgaaatc    30720
tgaataattt tgtgttactc atagcgcgta atactg                              30756
```